US008178336B2

(12) United States Patent
Derkx et al.

(10) Patent No.: US 8,178,336 B2
(45) Date of Patent: May 15, 2012

(54) POLYPEPTIDE

(75) Inventors: Patrick Maria Franciscus Derkx, Tikob (NL); Anja Kellet-Smith Hemmingen, Soborg (DK); Rie Mejldal, Copenhagen (DK); Bo Spange Sørensen, Skanderborg (DK); Karsten Matthias Kragh, Viby J (DK)

(73) Assignee: Danisco A/S, Copenhagen (DK)

( * ) Notice: Subject to any disclaimer, the term of this patent is extended or adjusted under 35 U.S.C. 154(b) by 315 days.

(21) Appl. No.: 12/339,718

(22) Filed: Dec. 19, 2008

(65) Prior Publication Data
US 2009/0202675 A1   Aug. 13, 2009

Related U.S. Application Data

(63) Continuation-in-part of application No. PCT/IB2007/002056, filed on Jun. 19, 2007.

(60) Provisional application No. 60/814,851, filed on Jun. 19, 2006.

(51) Int. Cl.
*C12N 9/28* (2006.01)
*C12N 9/24* (2006.01)
*C12N 9/00* (2006.01)
*C12P 21/06* (2006.01)
*C07H 21/04* (2006.01)
*A21D 2/00* (2006.01)
*A23C 9/12* (2006.01)

(52) U.S. Cl. ........ 435/202; 435/200; 435/201; 435/183; 435/69.1; 435/20; 435/61; 536/23.2

(58) Field of Classification Search .................. None
See application file for complete search history.

(56) References Cited

U.S. PATENT DOCUMENTS

| 4,683,202 | A | 7/1987 | Mullis |
| 4,946,779 | A | 8/1990 | Kameda et al. |
| 5,204,254 | A | 4/1993 | Schmid et al. |
| 5,958,749 | A | 9/1999 | Kubota et al. |
| 5,989,169 | A | 11/1999 | Svendsen et al. |
| 6,162,628 | A | 12/2000 | Cherry et al. |
| 6,242,224 | B1 | 6/2001 | Nakano et al. |
| 6,667,065 | B1 | 12/2003 | Kragh et al. |
| 7,166,453 | B2 | 1/2007 | Kragh et al. |
| 7,371,552 | B2 | 5/2008 | Kragh et al. |
| 2003/0134395 | A1 | 7/2003 | Shetty et al. |
| 2005/0059131 | A1 | 3/2005 | Bisgard-Frantzen et al. |
| 2005/0136524 | A1 | 6/2005 | Kragh et al. |
| 2005/0137111 | A1 | 6/2005 | Kragh et al. |
| 2006/0008888 | A1 | 1/2006 | Kragh et al. |
| 2006/0008890 | A1 | 1/2006 | Kragh et al. |
| 2006/0018997 | A1 | 1/2006 | Kragh et al. |
| 2006/0073583 | A1 | 4/2006 | Kragh et al. |
| 2007/0020727 | A1 | 1/2007 | Berg et al. |
| 2007/0020731 | A1 | 1/2007 | Kragh et al. |
| 2007/0072270 | A1 | 3/2007 | Kragh et al. |
| 2007/0141693 | A1 | 6/2007 | Berg et al. |
| 2008/0107773 | A1 | 5/2008 | Kragh et al. |
| 2008/0227173 | A1 | 9/2008 | Berg et al. |
| 2008/0274531 | A1 | 11/2008 | Berg et al. |
| 2008/0292747 | A1 | 11/2008 | Berg et al. |

FOREIGN PATENT DOCUMENTS

| EP | 120 693 | 3/1984 |
| EP | 0 494 233 | 1/1991 |
| EP | 0 412 607 | 2/1991 |
| EP | 0 298 645 | 6/1998 |
| JP | 6-279745 | 10/1994 |
| JP | 6-279746 | 10/1994 |
| JP | 8-205865 | 8/1996 |
| JP | 2000-245466 | 9/2000 |
| WO | WO 91/04669 | 4/1991 |
| WO | WO 99/23211 | 5/1999 |
| WO | WO 99/50399 | 10/1999 |
| WO | WO 00/58447 | 10/2000 |
| WO | WO 01/04273 | 1/2001 |
| WO | WO 02/068589 | 9/2002 |
| WO | WO 2004/091544 | 10/2004 |
| WO | WO 2004/111217 | 12/2004 |
| WO | WO 2005/003339 | 1/2005 |
| WO | WO 2005/007867 | 1/2005 |
| WO | WO 2006/003461 | 1/2006 |
| WO | PCT/US2004/021723 | 6/2007 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
U.S. Appl. No. 11/887,977, filed Oct. 5, 2007, Berg et al.
U.S. Appl. No. 12/339,718, filed Dec. 19, 2008, Derkx et al.
Yoshiyuki Takasaki, "Production of Maltohexaose by α-Amylase from *Bacillus circulans* G-6", Agric. Biol. Chem., vol. 46, No. 6, 1982, pp. 1539-1547.
Hajime Taniguchi et al., "Purification of *Baccillus circulans* F-2 Amylase and Its General Properties", Agric. Biol. Chem. vol. 47, No. 3, 1983, pp. 511-519.
Francis J. Bealin-Kelly et al., "The α-amylase of the caldoactive bacterium *Bacillus caldovelox*", Biochemical Society Transactions, vol. 18, No. 2, 1990, pp. 310-311.
William M. Fogarty et al., "A novel maltohexaose-forming α-amylase from *Bacillus caldovelox*: patterns and mechanisms of action", Appl Microbiol Biotechnol, 1991, vol. 36, pp. 184-189.
Narimasa Saito, "A Thermophilic Extracellular α-Amylase from *Baccilus licheniformis*", Archives of Biochemistry and Biophysics, vol. 155, 1973, pp. 290-298.

(Continued)

*Primary Examiner* — Anand Desai
*Assistant Examiner* — Iqbal H Chowdhury
(74) *Attorney, Agent, or Firm* — Vedder Price P.C.; Thomas J. Kowalski; Smith B. Uthaman

(57) ABSTRACT

We describe a PS4 variant polypeptide derivable from a parent polypeptide having non-maltogenic exoamylase activity, in which the PS4 variant polypeptide comprises an amino acid substitution at position 307 to lysine (K) or arginine (R), with reference to the position numbering of a *Pseudomonas saccharophilia* exoamylase sequence shown as SEQ ID NO: 1. Preferably, the PS4 variant polypeptide further comprises an amino acid substitution at position 70, preferably G70DThe amino acid at positions 272 and 303 of the sequence of the are preferably histidine (H) and glycine (G).

34 Claims, 13 Drawing Sheets

OTHER PUBLICATIONS

Bradford, 1976

Hajime Taniguchi "Matohexaose-Producing Amylase of *Bacillus circulans* F-2" National Food Research Institute, 1991, pp. 111-124.

Altschul et al., 1990, J. Mol. Biol. 403-410. "Basic Local Alignment Search Tool".

Bernfeld, *Methods Enzymol.*, (1954), 1, 149-158. "Amylase, α and β."

Beucage S.L. et al.,(1981) *Tetrahedron Letters* 22, p. 1859-1869. "Deoxynucleoside Phosphoramidites—A New Class of Key Intermediates for Deoxypolynucleotide Synthesis"., Anal. Biochem., 72, 248. "A Rapid and Senstitive Method for the Quantitation of Microgram Quantities of Protein Utilizing the Principle of Protein-Dye Binding".

Caruthers MH et al., (1980) Nuc. Acids Res. Symp. Ser. 215-23. "New Chemical Methods for Synthesizing Polynucleotides."

Devereux et al., 1984, Nuc. Acids Research 12 p. 387. "A Comprehensive set of sequence analysis programs for the VAX".

Henrissat B, Bairoch A; Biochem. J., 316,695-696 (1996)) "Updating the sequence-based classification of glycosyl hydrolases."

Higgins DG & Sharp PM (1988), Gene 73(1),237-244. "CLUSTAL: a package for performing multiple sequence alignment on a microcomputer".

Horn T. et al., 1980, Nuc. Acids Resp. Symp. Ser. 225-232. "Synthesis of Oligonucleotides on Cellulose."

Horwell DC, *Trends Biotechnol.* (1995) 13(4),132-134. "The 'peptoid' approach to the design of non-peptide, small molecule agonists and antagonists of neuropeptides."

Matthes et al., (1984) *EMBO J.* 3, p. 801-805 "Simultaneous rapid chemical synthesis of over one hundred oligonucleotides on a microscale".

Morinaga et al., (*Biotechnology* (1984) 2, p. 646-649). "Improvement of Oligonucleotide-Directed Site-Specific Mutagenesis Using Double-Stranded Plasmid DNA".

Nelson and Long, Analytical Biochemistry, 1989, 180, p. 147-151. "A General Method of Site-Specific Mutagenesis Using a Modification of the Thermus aquaticus Polymerase Chain Reaction".

Saiki R K et al. (*Science* (1988) 239, pp. 487-491. "Primer-Directed Enzymatic Amplification of DNA with a Thermostable DNA polymerase".

Sarkar and Sommer (*Biotechniques* (1990), 8, p. 404-407. "The "Megaprimer" Method of Site-Directed Mutagenesis".

Yoshiyuki Sakano et al., "Purification and Properties of an exo-α-Amylase from *Pseudomonas stutzer*", Agric. Biol. Chem., vol. 46, No. 3, 1982, pp. 639-646.

Yoshiyuki Takasaki et al., "Maltotetraose-producing Amylase from *Bacillus* sp. MG-4", Agric. Biol. Chem., vol. 55, No. 7, 1991, pp. 1715-1720.

A.K. Chandra et al., "Production of Extracellular Thermostable α-Amylase by *Bacillus licheniformis*", J. Ferment. Technol. vol. 58, No. 1, 1980, pp. 1-10.

R.A.K. Srivastava et al., "Culture Conditions for Production of Thermostable Amylase by *Bacillus stearothermophilus*", Applied and Environmental Microbiology, Jul. 1986, pp. 179-184.

Veronique Planchot et al.., "Purification and characterization of extracellular alpha-amylase from *Aspergillus fumigatus*", Carbohydrate Research, vol. 272, 1995, pp. 97-109.

Ohnishi et al., "General Consideration for Conditions and Methods of Amylase Assay", Handbook of Amylases and Related Enzymes, The Amylase Research Society of Japan, 1988, pp. 10-14.

Kim L. Larsen et al., "Purification and characterization of cyclodextrin glycosyltransferase from *Paenibacillus* sp. F8", Carbohydrate Research, vol. 310, 1998, pp. 211-219.

Helmut Blum et al., "Improved silver staining of plant proteins, RNA and DNA in polyacrylamide gels", Electrophoresis, 1987, vol. 8, pp. 93-99.

Hidetsugu Fuwa, "A New Method for Microdetemiination of Amylase Activity by the Use of Amylose as the Substrate", The Journal of Biochemistry, vol. 41, No. 5, 1954, pp. 583-603.

Akira Tsukamoto et al., "Nucleotide Sequence of the Maltohexaose-Producing Amylase Gene from an Alkalophilic *Bacillus* sp. #707 and Structural Similarity to Liquefying Type α-Amylase", Biochemical and Biophysical Research Communications, vol. 151, No. 1, Feb. 29, 1988, pp. 25-31.

Y.C. Lee, "Carbohydrate analyses with high-performance anion-exchange chromatography", Journal of Chromatography A., vol. 720, 1996, pp. 137-149.

Robert N. Ammeraal et al., "High-performance anion-exchange chromatography with pulsed amperometric detection of linear and branched glucose oligosaccharides", Carbohydrate Research, vol. 215, 1991, pp. 179-192.

Greg Winter et al., "Man-made antibodies", Nature, vol. 349, 1991, pp. 293-299.

Rosario Orlandi et al.., "Cloning immunoglobulin variable domains for expression by the polymerase chain reaction", Proc. Natl. Acad. Sci. USA, vol. 86, May 1989, pp. 3833-3837.

Shun-ichi Takeda et al., "Construction of chimaeric processed immunoglobulin genes containing mouse variable and human constant region sequences", Nature, vol. 314, Apr. 1985, 452-454.

Michael S. Neuberger, et al., "Recombinant antibodies possessing novel effector functions", Nature, vol. 312, Dec. 13, 1984, pp. 604-608.

Sherie L. Morrison et al., "Chimeric human antibody molecules: Mouse antigen-binding domains with human constant region domains", Proc. Natl. Acad. Sci. USA, vol. 81, Nov. 1984, pp. 6851-6855.

J. F. Kennedy et al., "Characteristics of alpha-Amylase K, a Novel Amylase from a Strain of *Bacillus subtilis*", Starch/Starke, vol. 31, No. 3, 1979, pp. 93-99.

Sambrook, J., E. F. Fritsch, and T. Maniatis, 1989, "Molecular Cloning: A Laboratory Manual", Second Edition, Books 1-3.

S.P.C. Cole et al., "The EBV-Hybridoma Technique and Its Application to Human Lung Cancer", Monoclonal Antibodies and Cancer Therapy, 1985, pp. 77-96.

Richard J. Cote, et al., "Generation of human monoclonal antibodies reactive with cellular antigens", Proc. Natl. Acad. Sci. USA, vol. 80, Apr. 1983, pp. 2026-2030.

Danuta Kozbor et al., "The production of monoclonal antibodies from human lymphocytes", Immunology Today, vol. 4, No. 3, 1983.

Kohler et al., Nature, vol. 256, 1975, pp. 495-497 "Continuous cultures of fused cells secreting antibody of predefined specificity."

M. Antoinette Mc Tigue et al., The alkaline amylase of the alkalophilic *Bacillus* sp. IMD 370, Department of Industrial Microbiology, vol. 17, 1995, pp. 570-573.

Takaya Hayashi et al., "Properties of new alkaline maltohexaose-forming amylases", Appl Microbiol Biotechnol, vol. 28, 1988, pp. 281-285.

Tae Un Kim et al., "Purification and Characterization of a Maltotetraose-Forming Alkaline α-Amylase from an Alkalophilic *Bacillus* Strain, GM8901", Applied and Environmental Microbiology, Aug. 1995, pp. 3105-3112.

Keiji Kainuma et al., "Isolation and Action Pattern of Maltohexaose Producing Amylase From *Aerobacter aerogenes*", FEBS Letters, vol. 26, No. 1, Oct. 1972, pp. 281-285.

Claus Christophersen et al., "Enzymatic Characterizatoin of Novamyl a Thermostable α-Amylase", 1998, Starch/Starke, vol. 50, No. I, pp. 39-45.

Byoung-Cheol Min et al., "Cloning of Novel Maltooligosaccharide-Producing Amylases as Antistaling Agents for Bread", J. Agric. Food Chem, 1998, vol. 46, pp. 779-782.

Tadeusz Jakubezyk et al., "Scientific Transactions of the Academy of Agriculture in Warsaw", Agricultural and Food Technology, vol. 8, 1973, pp. 223-235.

Jianhua Zhou et al., "Properties of the enzyme expressed by the *Pseudomonas saccharophila* maltotetraohydrolase gene (mta) in *Escherichia coli*", Carbohydrate Research, vol. 223, 1992, pp. 255-261.

Mitsuru Monma et al. "Formation and Hydrolysis of Maltohexaose by an Extracellular Exo-maltohexaohydrolase", Agric. Biol. Chem., vol. 47, No. 8, 1983, pp. 1769-1774.

William M. Fogarty et al., "Extracellular Maltotetraose-Forming Amylase of *Pseudomonas* Sp". IMD 353, Biotechnology Letters, vol. 16, No. 5, May 1994, pp. 473-478.

Katsuo Wako et al., "Purification and Some Properties of a Maltotriose-producing Amylase", J. Jap. Soc. Starch Sci., vol. 26, No. 3, 1979, pp. 175-181.

Yoshiyuki Takasaki, "An Amylase Producing Maltotriose from *Bacillus subtilis*", Agric. Biol. Chem., vol. 49, No. 4, 1985, pp. 1091-1097.

E. Ann MacGregor, "Relationship of Sequence and Structure to Specificity in the α-amylase family of Enzymes", Biochimica et Biphysica Acta 1546 (2001) p. 1-20.

Simon RJ et al. *PNAS* (1992) 89(20), 9367-9371. "Peptoids: A Modular approach to drug discovery".

Smith et al., 1988, Gene 70, 351-361. "Characterization of signal-sequence-coding regions selected from the *Bacillus subtilis* chromosome".

Tatusova, T. FEMS Microbiol Lett 1999 174(2): 247-50. "BLAST 2 sequences, a new tool for comparing protein and nucleotide sequences".

Tatusova, T. FEMS Microbiol Lett 1999 177(1): 187-188. Erratum to "BLAST 2 Sequences, a new tool for comparing protein and nucleotide sequences".

Taylor W.R. (1986) "The classification of amino acid conservation" *J. Theor.Biol.* 119; 205-218.

Fujita et al. "Cloning and Nucleotide Sequence of the Gene (amyP) for Maltotetraose-Forming Amylase from *Pseudomonas stutzeri* MO-19," *J. Bactrol.* 1989, 171, 1333-1339.

Van der Maarel et al., "Properties and applications of starch-converting enzymes of the beta-amylase family," *J. of Biotechnology*, 94 (2002) pp. 137-155.

Ausubel et al., 1999, "Short Protocols in Molecular Biology", pp. 7-58 to 7-60.

Ausubel, F. M. et al. Cold Spring Harbor Laboratory Press; (1995 and periodic supplements).

Ed Harlow and David Lane "Antibodies, A Laboratory Manual", Cold Spring Harbor Laboratory Press, ISBN 0-87969-314-2, 1988.

Roskams, Jane and Linda Rodgers, "Lab Ref: A Handboook of Recipes, Reagents, and Other Reference Tools for Use at the Bench", Cold Spring Harbor Laboratory, ISBN 0-87969-630-3, 2002.

Larsson, Lars-Inge "Immunocytochemistry: Theory and Practice", CRC Press inc., Baca Raton, Florida, 1988, ISBN 0-8493-6078-1.

Seethala, Ramakrishna; Prabhavathi B. Femandes, "Handbook of Drug Screening" vol. 114, Marcel Dekker, 2001, New York, NY, ISBN 0-8247-0562-9.

Lane, David; Ed Harlow, "Using Antibodies: A Laboratory Manual: Portable Protocol No. I" (1998, Cold Spring Harbor Laboratory Press, ISBN 0-87969-544-7).

Gait, M.J., (ed), 1984, "Oligonucleotide Synthesis: A Practical Approach", IRL Press.

Polak, J. M. and James O'D. McGee, 1990, "In Situ Hybridization: Principles and Practice".

Pound John D. (ed); "Immunochemical Protocols, vol. 80", in the series: "Methods in Molecular Biology", Humana Press, Totowa, New Jersey, 1998.

Roe, B., Crabtree, J., and A. Kahn, "Current Protocols in Molecular Biology", ch. 9, 13, and 16, John Wiley & Sons, New York, N. Y., 1996.

Hisashi Okemoto et al., "Isolation and cultivation of a novel microorganism producing a maltopentaose-forming enzyme", Appl Microbiol Biotechnol, 1986, vol. 25, pp. 137-142.

Jianhua Thou et al., "Nucleotide sequence of the maltotetraohydrolase gene from *Pseudomonas saccharophila*", FEBS Letters, vol. 255, No. 1, 1989, 3741, pp. 37-41.

William M. Fogarty, Department of Industrial Microbiology, University College, Dublin, Ireland, "Microbial Amylases", 1983, W.M Fogarty (Ed.) Microbial Enzymes and biotechnology, Applied Science, London, pp. 1-92.

William M. Fogarty et al., "Starch-Degrading Enzymes of Microbial Origin", Progress in Industrial Microbiology, vol. 15, M.J. Bull (Ed), Elsevier Scientific, 1979, pp. 87-150.

Keiji Kainurna et al., "Purification and some properties of a novel Maltohexaose-Producing Exo-Amylase From *Aerobacter aerogenes*", Biochimica et Biophysics Acta, 410 (1975) 333-346.

Osamu Shida et al., "Cloning and Nucleotide Sequence of the Maltopentaose-forming Amylase Gene from *Pseudomonas* sp. KO-8940", Biosci. Biotech. Biochern. vol. 56, No. 1, pp. 76-80, 1992.

E. Ann MacGregor, Relationship of Sequence and Structure to Specificity in the α-Amylase Family of Enzymes, Biochimica et Biphysica Acta 1546 (2001) p. 1-20.

Geneseq Database Accession No. ADW75733, A. Gernot, et al., Saccharophilia Variant Maltotetrahydrolase Protein Seq ID 5, Apr. 7, 2005.

Geneseq Database Accession No. ADW75735, A. Gernot, et al., Stutzeri Maltotetrahydrolase Mature Protein Seq ID 7, Apr. 7, 2005.

Geneseq Database Accession No. ADW73063. C.T. Berg, et al., Stutzeri Maltotetrahydrolase Gene Seq ID 12, Apr. 7, 2005.

GenomeNet 1GCY, Aug. 14, 2000, High Resolution Crystal Structure of Maltotetraose-Forming Exo-Amylase.

Damien Devos, et al., Practical Limits of Function Prediction, Proteins: Structure, Function, and Genetics (2000) vol. 41, p. 98-107.

S. Sen, et al., Developments in Directed Evolution for Improving Enzyme Functions, Applied Biochemistry and Biotechnology (2007) vol. 143, p. 212-223.

James C. Whisstock, et al., Prediction of Protein Function From Protein Sequence and Structure, Quarterly Reviews of Biophysics (2003) vol. 36, No. 3, p. 307-340.

UniProt database Accession No. P22963, Glucan 1,4-alpha-maltotetrahydrolase, Aug. 1, 1991.

* cited by examiner

POLYPEPTIDE

This application is a continuation-in-part of PCT/IB2007/002056 filed Jun. 19, 2007 and published as WO 2007/148224 on Dec. 27, 2007, which claims priority from U.S. Provisional Application No. 60/814,851 filed Jun. 19, 2006.

Reference is made to U.S. provisional application Ser. Nos. 60/485,413, 60/485,539 and 60/485,616 filed Jul. 7, 2003. Reference is also made to international applications PCT/US2004/021723 and PCT/US2004/021739 filed Jul. 7, 2004 and designating the US (applicant: Genencor International, Inc). Reference is also made to U.S. utility application Ser. Nos. 10/886,905 and 10/866,903 all of which were also filed Jul. 7, 2004.

Reference is also made to U.S. provisional application Ser. No. 60/608,919 (filed as U.S. utility application Ser. No. 10/887,056 on Jul. 7, 2004 but converted to a provisional application on Sep. 15, 2004). Reference is also made to U.S. provisional application Ser. No. 60/612,407 which was filed Sep. 22, 2004.

Reference is additionally made to U.S. application Ser. No. 60/485,539 filed Jul. 7, 2003. Reference is also made to international application PCT/IB2004/002487 filed Jul. 7, 2004 and designating the US (applicant: Danisco A/S). Reference is also made to U.S. utility application Ser. No. 10/886,023 filed Jul. 7, 2004.

Reference is also made to U.S. utility application Ser. Nos. 10/886,505, 10/886,527 and 10/886,504, all of which were filed Jul. 7, 2004. Reference is also made to U.S. utility application Ser. No. 10/947,612 filed Sep. 22, 2004.

Reference is also made to International Patent Application serial number PCT/GB2005/002675 filed Jul. 7, 2005 and designating the US (applicants: Danisco A/S and Genencor International, Inc, D Young & Co). Reference is also made to U.S. provisional application Ser. No. 60/697,302 filed Jul. 7, 2005.

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

SEQUENCE LISTING

The instant application contains a Sequence Listing which has been submitted in ASCII format via EFS-Web and is hereby incorporated by reference in its entirety. Said ASCII copy, created on May 5, 2011, is named 43049287.txt and is 120,189 bytes in size.

FIELD

This invention relates to polypeptides, specifically amylase polypeptides and nucleic acids encoding these, and their uses as non-maltogenic exoamylases in producing food products.

The amylases of the present invention have been engineered to have more beneficial qualities. Specifically, the amylases of the current invention show an altered exospecifity and/or altered thermostability. In particular, the polypeptides are derived from polypeptides having non-maltogenic exoamylase activity, in particular, glucan 1,4-alpha-maltotetrahydrolase (EC 3.2.1.60) activity.

BACKGROUND

Improved amylases can ameliorate problems inherent in certain processes, such as baking. Crystallisation of amylopectin takes place in starch granules days after baking, which leads to increased firmness of bread and causes bread staling. When bread stales, bread loses crumb softness and crumb moisture. As a result, crumbs become less elastic, and bread develops a leathery crust.

Enzymatic hydrolysis (by amylases, for example) of amylopectin side chains can reduce crystallization and increase anti-staling. Crystallization depends upon the length of amylopectin side chains: the longer the side chains, the greater the crystallization. Most starch granules are composed of a mixture of two polymers: amylopectin and amylose, of which about 75% is amylopectin. Amylopectin is a very large, branched molecule consisting of chains of α-D-glucopyranosyl units joined by (1-4) linkages, where the chains are attached by α-D-(1-6) linkages to form branches. Amylose is a linear chain of (1-4) linked α-D-glucopyranosyl units having few α-D-(1-6) branches.

Baking of farinaceous bread products such as white bread, bread made from bolted rye flour and wheat flour and rolls is accomplished by baking the bread dough at oven temperatures in the range of from 180 to 250° C. for about 15 to 60 minutes. During the baking process a steep temperature gradient (200→120° C.) prevails over the outer dough layers where the crust of the baked product is developed. However, due to steam, the temperature in the crumb is only about 100° C. at the end of the baking process. Above temperatures of about 85° C., enzyme inactivation can take place and the enzyme will have no anti-staling properties. Only thermostable amylases, thus, are able to modify starch efficiently during baking.

Endoamylase activity can negatively affect the quality of the final bread product by producing a sticky or gummy crumb due to the accumulation of branched dextrins. Exoamylase activity is preferred, because it accomplishes the desired modification of starch that leads to retardation of staling, with fewer of the negative effects associated with endo-amylase activity. Reduction of endoamylase activity can lead to greater exospecifity, which can reduce branched dextrins and produce a higher quality bread.

SUMMARY

We provide, according to the invention, a PS4 variant polypeptide as set out in the claims. We further provide for the use of such a PS4 variant polypeptide, including in and as food additives, food products, bakery products, improver compositions, feed products including animal feeds, etc as set out in the claims. We provide for nucleic acids which encode and which relate to PS4 variant polypeptides, as set out in the claims. Methods for producing such PS4 variant polypeptides, as well as other aspects of the invention, are also set out in the claims.

SEQUENCE LISTINGS

Figure 1:
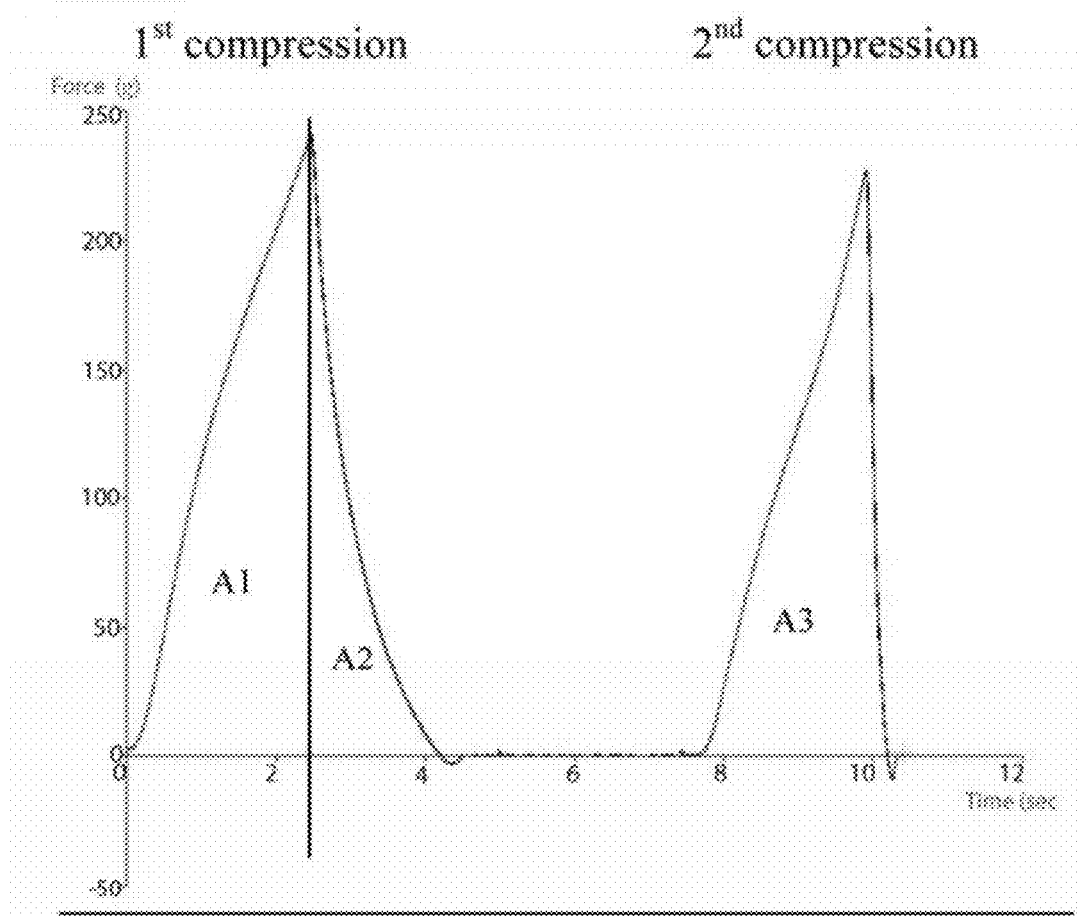
FIG. 1 shows an example of a curve from a Texture Analyser.

SEQ ID NO: 1 shows a PS4 reference sequence, derived from *Pseudomonas saccharophila* maltotetrahydrolase amino acid sequence. SEQ ID NO: 2 shows a pSac-D34 sequence; *Pseudomonas saccharophila* maltotetrahydrolase amino acid sequence with 11 substitutions and deletion of the starch binding domain. SEQ ID NO: 3 shows a pSac-D20 sequence; *Pseudomonas saccharophila* maltotetrahydrolase amino acid sequence with 13 substitutions and deletion of the starch binding domain. SEQ ID NO: 4 shows a pSac-D14 sequence; *Pseudomonas saccharophila* maltotetrahydrolase amino acid sequence with 14 substitutions and deletion of the starch binding domain. SEQ ID NO: 5 shows a *Pseudomonas saccharophila* Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase). SWISS-PROT accession number P22963. SEQ ID NO: 6 shows a *P. saccharophila* mta gene encoding maltotetraohydrolase (EC number=3.2.1.60). GenBank accession number X16732. SEQ ID NO:7 shows a PS4 reference sequence, derived from *Pseudomonas stutzeri* maltotetrahydrolase amino acid sequence. SEQ ID NO: 8 shows a PStu-D34 sequence; *Pseudomonas stutzeri* maltotetrahydrolase amino acid sequence with 9 substitutions. SEQ ID NO: 9 shows a PStu-D20 sequence; *Pseudomonas stutzeri* maltotetrahydrolase amino acid sequence with 11 substitutions. SEQ ID NO: 10 shows a PStu-D14 sequence; *Pseudomonas stutzeri* maltotetrahydrolase amino acid sequence with 12 substitutions. SEQ ID NO: 11 shows a *Pseudomonas stutzeri* (*Pseudomonas perfectomarina*). Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P13507. SEQ ID NO: 12 shows a *P. stutzeri* maltotetraose-forming amylase (amyp) gene, complete cds. GenBank accession number M24516.

SEQ ID NO: 13 shows a pSac-pMD229 amino acid sequence having mutations 33Y, 34N, 121F, 134R, 141P, 146G, 157L, 161A, 178F, 179T, 223E, 229P, 272Q, 303E, 307L, 309P and 334P. SEQ ID NO: 14 shows a pSac-pMD229 nucleic acid sequence. SEQ ID NO: 15 shows a pSac-pMD248 amino acid sequence having mutations 33Y, 34N, 121F, 134R,141P, 145D, 146G, 157L, 178F, 179T, 223E, 229P, 272Q, 303E, 307L and 334P. SEQ ID NO: 16 shows a pSac-pMD248 nucleic acid sequence. SEQ ID NO: 17 shows a pSac-pMD253 amino acid sequence having mutations 33Y, 34N, 121D, 134R, 141P, 146G, 157L, 178F, 179T, 223E, 229P, 272Q, 303E, 307L, 309P and 334P. SEQ ID NO: 18 shows a pSac-pMD253 nucleic acid sequence. SEQ ID NO: 19 shows a pSac-pMD271 amino acid sequence having mutations 3S, 33Y, 34N, 70D, 121D, 134R,141P, 146G, 157L, 178F, 179T, 223E, 229P, 272Q, 303E, 307L, 309P and 334P. SEQ ID NO: 20 shows a pSac-pMD271 nucleic acid sequence.

SEQ ID NO: 21 shows a pSac-pMS382 amino acid sequence having mutations 33Y, 34N, 70D, 121F, 134R,141P, 146G, 157L, 161A, 178F, 179T, 223E, 229P, 307K, 309P and 334P. SEQ ID NO: 22 shows a pSac-pMS382 nucleotide sequence sequence. SEQ ID NO: 23 shows a pSac-pMS382R amino acid sequence having mutations 33Y, 34N, 70D, 121F, 134R,141P, 146G, 157L, 161A, 178F, 179T, 223E, 229P, 307R, 309P and 334P. SEQ ID NO: 24 shows a pSac-pMS382R nucleotide sequence sequence. SEQ ID NO: 25 shows a pSac-pMS382H amino acid sequence having mutations 33Y, 34N, 70D, 121F, 134R,141P, 146G, 157L, 161A, 178F, 179T, 223E, 229P, 309P and 334P. SEQ ID NO: 26 shows a pSac-pMS382H nucleotide sequence.

SEQ ID NO: 27 shows a SSM471 B10 amino acid sequence having mutations 33Y, 34N, 121F, 134R,141P, 146G, 157L, 161A, 178F, 179T, 223E, 229P, 272Q, 303E, 307R, 309P and 334P. SEQ ID NO: 28 shows a SSM471 B10 nucleic acid sequence. SEQ ID NO: 29 shows a SSM471 C04 amino acid sequence having mutations 33Y, 34N, 121F, 134R,141P, 146G, 157L, 161A, 178F, 179T, 223E, 229P, 272Q, 303E, 307K, 309P and 334P. SEQ ID NO: 30 shows a SSM471 C04 nucleic acid sequence. SEQ ID NO: 31 shows a PMS 370 amino acid sequence having mutations 33Y, 34N, 121F, 134R, 141P, 146G, 157L, 161A, 178F, 179T, 223E, 229P, 272Q, 303E, 309P and 334P. SEQ ID NO: 32 shows a PMS 370 nucleic acid sequence.

DETAILED DESCRIPTION

In the following description and examples, unless the context dictates otherwise, dosages of PS4 variant polypeptides are given in parts per million (micrograms per gram) of flour. For example, "1 D34" indicates 1 part per million of pSac-D34 based on weight per weight. Preferably, enzyme quantities or amounts are determined based on activity assays as equivalents of pure enzyme protein measured with bovine serum albumin (BSA) as a standard, using the assay described in Bradford (1976, A rapid and sensitive method for the quantification of microgram quantities of protein utilizing the principle of protein-dye binding. Anal. Biochem. 72:248-254).

In describing the different PS4 variant polypeptide variants produced or which are contemplated to be encompassed by this document, the following nomenclature will be adopted for ease of reference:
  (i) where the substitution includes a number and a letter, e.g., 141P, then this refers to [position according to the numbering system/substituted amino acid]. Accordingly, for example, the substitution of an amino acid to proline in position 141 is designated as 141P;
  (ii) where the substitution includes a letter, a number and a letter, e.g., A141P, then this refers to [original amino acid/position according to the numbering system/substituted amino acid]. Accordingly, for example, the substitution of alanine with proline in position 141 is designated as A141P.

Where two or more possible substituents are possible at a particular position, this will be designated by contiguous letters, which may optionally be separated by slash marks "/", e.g., G303ED or G303E/D. Where the relevant amino acid at a position can be substituted by any amino acid, this is designated by [position according to the numbering system/X], e.g., 121X.

Multiple mutations may be designated by being separated by slash marks "/", e.g. A141P/G223A or commas ",", A141P, G223A representing mutations in position 141 and 223 substituting alanine with proline and glycine with alanine respectively.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, New York (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols*, vol 80", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

All patents and publications, including all sequences disclosed within such patents and publications, referred to herein are expressly incorporated by reference.

PS4 Variant Polypeptides

We provide a polypeptide having a substitution at one or more positions which effect an altered property, which may be any combination of altered exospecificity or altered thermostability, or an altered handling property, relative to the parent enzyme. Such variant polypeptides are referred to in this document for convenience as "PS4 variant polypeptides".

The PS4 variant polypeptides preferably exhibit enzyme activity. More preferably, the PS4 variant polypeptides comprise amylase activity, preferably exoamylase activity. In highly preferred embodiments, the PS4 variant polypeptides exhibit non-maltogenic exoamylase activity.

We further provide for compositions, including food additives, food products, bakery products, improver compositions, feed products including animal feeds, etc comprising such altered PS4 variant polypeptides, preferably those which have non-maltogenic exoamylase activity, as well as methods of making and using such polypeptides and the compositions.

As noted above, the PS4 variant polypeptides may comprise one or more improved handling properties, preferably improved baking properties. Thus, the PS4 variant polypeptides are such that the food products so treated have one or more of (preferably all of) a lower firmness, a higher resilience, a higher cohesiveness, a lower crumbliness or a higher foldability. Such improved handling or baking properties exhibited by the PS4 variant polypeptides are described in further detail below.

We provide for the treatment of food products, particularly doughs and bakery products with such polypeptides, and such that the food products exhibit the desired qualities set out above.

We provide for other uses of such compositions such as in the preparation of detergents, as sweeteners, syrups, etc. The compositions include the polypeptide together with at least one other component. In particular, we provide for food or feed additives comprising the polypeptides.

Such polypeptides and nucleic acids vary from their parent sequences by including a number of mutations. In other words, the sequence of the PS4 variant polypeptide or nucleic acid is different from that of its parent at a number of positions or residues. In preferred embodiments, the mutations comprise amino acid substitutions, that is, a change of one amino acid residue for another. Thus, the PS4 variant polypeptides comprise a number of changes in the nature of the amino acid residue at one or more positions of the parent sequence.

As used herein, the term "variant" should be taken to mean a molecule being derivable from a parent molecule. Variants include polypeptides as well as nucleic acids. Variants include deletions, insertions and substitutions at the amino acid level and transversions, transitions and inversions at the nucleic acid level among other things, at one or more locations. Variants also include truncations. Variants include homologous and functional derivatives of parent molecules. Variants include sequences that are complementary to sequences that are capable of hybridising to the nucleotide sequences presented herein.

Position 307 Basic Residue Mutants

We provide for PS4 variant polypeptides with sequence alterations comprising amino acid substitutions in a amylase sequence, preferably an exoamylase activity, more preferably a non-maltogenic exoamylase sequence.

Specifically, we provide for a PS4 variant polypeptide derivable from a parent polypeptide having non-maltogenic exoamylase activity comprising an amino acid mutation at position 307 with reference to the position numbering of a *Pseudomonas saccharophilia* exoamylase sequence shown as SEQ ID NO: 1. The position 307 substitution is preferably a substitution to a basic or positively charged amino acid, preferably lysine (K) or arginine (R).

In one embodiment, we provide a PS4 variant polypeptide in which the amino acid substitution at position 307 is a substitution to lysine (307K), preferably H307K. In another embodiment, we provide a PS4 variant polypeptide according to claim 1 or 2, in which the amino acid substitution at position 307 is a substitution to arginine (307R), preferably H307R.

The PS4 variant polypeptide may further comprise a mutation at position 70 to aspartic acid (D), preferably 70D. In preferred embodiments, the substitution is G70D. Accordingly, in some embodiments, we provide for a PS4 variant polypeptide comprising substitutions G70D, H307K or G70D, H307R relative to a *Pseudomonas saccharophilia* exoamylase sequence shown as SEQ ID NO: 1.

The residues at positions 272 and 303 may be "wild type", or they may be mutated. In preferred embodiments, the residue at position 272 is a wild type residue, i.e., histidine (H) Preferably, the residue at position 303 is also a wild type residue, i.e., glycine (G). We therefore provide for a PS4 variant polypeptide comprising substitutions G70D and H307K with the residue at position 272 being H and the residue at position 303 being G, or G70D and H307R with the residue at position 272 being H and the residue at position 303 being G relative to a *Pseudomonas saccharophilia* exoamylase sequence shown as SEQ ID NO: 1.

Such variant polypeptides, and others as described in this document, are referred to in this document as "PS4 variant polypeptides". Nucleic acids encoding such variant polypeptides are also disclosed and will be referred to for convenience as "PS4 variant nucleic acids". PS4 variant polypeptides and nucleic acids will be described in further detail below.

The "parent" sequences, i.e., the sequences on which the PS4 variant polypeptides and nucleic acids are based, preferably are polypeptides having non-maltogenic exoamylase activity. The terms "parent enzymes" and "parent polypeptides" should be interpreted accordingly, and taken to mean the enzymes and polypeptides on which the PS4 variant polypeptides are based. They are described in further detail below.

The mutations and amino acid changes may be made on any suitable polypeptide backbone or background, wild type or mutated, as described in further detail below.

In particularly preferred embodiments, the parent sequences are non-maltogenic exoamylase enzymes, preferably bacterial non-maltogenic exoamylase enzymes. In highly preferred embodiments, the parent sequence comprises a glucan 1,4-alpha-maltotetrahydrolase (EC 3.2.1.60). Preferably, the parent sequence is derivable from *Pseudomonas* species, for example *Pseudomonas saccharophilia* or *Pseudomonas stutzeri*.

In some embodiments, the parent polypeptide comprises, or is homologous to, a wild type non-maltogenic exoamylase sequence, e.g., from *Pseudomonas* spp.

Thus, the parent polypeptide may comprise a *Pseudomonas saccharophilia* non-maltogenic exoamylase having a sequence shown as SEQ ID NO: 1. In other preferred embodiments, the parent polypeptide comprises a non-maltogenic exoamylase from *Pseudomonas stutzeri* having a sequence shown as SEQ ID NO: 11, or a *Pseudomonas stutzeri* non-maltogenic exoamylase having SWISS-PROT accession number P13507.

On the other hand, the parent polypeptide may be a variant of any of the wild type sequences, that is to say, the parent polypeptide may itself be engineered, or comprise a PS4 variant polypeptide.

In preferred embodiments, the mutations and changes are made on a PS4 sequence which is already mutated, preferably pMD 229 (SEQ ID NO: 13 or 14).

However, it will be clear to the skilled reader that although the PS4 variant polypeptides may be derivable by mutating already mutated sequences, it is possible to construct such variant polypeptides by starting from a wild type sequence (or indeed any suitable sequence), identifying the differences between the starting sequence and the desired variant, and introducing the required mutations into the starting sequence in order to achieve the desired variant.

Proteins and nucleic acids related to, preferably having sequence or functional homology with *Pseudomonas saccharophilia* non-maltogenic exoamylase sequence shown as SEQ ID NO: 1 or a *Pseudomonas stutzeri* non-maltogenic exoamylase having a sequence shown as SEQ ID NO: 11 are referred to in this document as members of the "PS4 family". Examples of "PS4 family" non-maltogenic exoamylase enzymes suitable for use in generating the PS4 variant polypeptides and nucleic acids are disclosed in further detail below.

The PS4 variant polypeptides described in this document preferably retain the features of the parent polypeptides, and additionally preferably have additional beneficial properties, for example, enhanced activity or thermostability, or pH resistance, or any combination (preferably all). This is described in further detail below.

The PS4 substitution mutants described here may be used for any suitable purpose. They may preferably be used for purposes for which the parent enzyme is suitable. In particular, they may be used in any application for which exo-maltotetraohydrolase is used. In highly preferred embodiments, they have the added advantage of higher thermostability, or higher exoamylase activity or higher pH stability, or any combination. Examples of suitable uses for the PS4 variant polypeptides and nucleic acids include food production, in particular baking, as well as production of foodstuffs; further examples are set out in detail below.

The PS4 variant polypeptides may comprise one or more further mutations in addition to those positions set out above. There may be one, two, three, four, five, six, seven or more mutations preferably substitutions in addition to those already set out. Other mutations, such as deletions, insertions and substitutions at the amino acid level and transversions, transitions and inversions at the nucleic acid level, at one or more other locations, may also be included, as described below. In addition, the PS4 variants need not have all the substitutions at the positions listed. Indeed, they may have one, two, three, four, or five substitutions missing, i.e., the wild type amino acid residue is present at such positions.

Further Mutations

Positions 33, 34, 70, 121, 134, 141, 146, 157, 161, 178, 179, 223, 229, 309 and/or 334

In preferred embodiments, the PS4 variant polypeptide may comprise one or more further mutations at other sites or positions in its sequence.

For example, the PS4 variant polypeptide may further comprise one or more mutations selected from the group consisting of positions: 33, 34, 70, 121, 134, 141, 146, 157, 161, 178, 179, 223, 229, 309 or 334. The residues at these positions may preferably comprise 33Y, 34N, 70D, 121F, 134R, 141P, 146G, 157L, 161A, 178F, 179T, 223E, 229P, 307K, 309P or 334P.

The PS4 variant polypeptide may therefore comprise, in addition to 307K/R/H, 1, 2, 3, 4, 5, 6, 7, 8, 9, 10, 11, 12, 13, 14 or all 15 mutations at positions 33, 34, 70, 121, 134, 141, 146, 157, 161, 178, 179, 223, 229, 309 or 334. The position 307 residue in such embodiments may comprise histidine (H), particularly where such further mutations are present.

The PS4 variant polypeptide may therefore comprise, in addition to 307K/R/H, 1 further mutation at any of positions 33, 34, 70, 121, 134, 141, 146, 157, 161, 178, 179, 223, 229, 309 or 334, as shown in "Annex A: 1 Mutation", i.e., 33Y; 34N; 70D; 121F; 134R; 141P; 146G; 157L; 161A; 178F; 179T; 223E; 229P; 309P; or 334P.

In other words, the PS4 variant polypeptide may comprise any of the following: 33Y, 307K/R/H; 34N, 307K/R/H; 70D, 307K/R/H; 121F, 307K/R/H; 134R, 307K/R/H; 141P, 307K/R/H; 146G, 307K/R/H; 157L, 307K/R/H; 161A, 307K/R/H; 178F, 307K/R/H; 179T, 307K/R/H; 223E, 307K/R/H; 229P, 307K/R/H; 309P, 307K/R/H; or 334P, 307K/R/H.

The PS4 variant polypeptide may alternatively comprise, in addition to 307K/R/H, 2 further mutations at any of positions 33, 34, 70, 121, 134, 141, 146, 157, 161, 178, 179, 223, 229, 309 or 334, as shown in "Annex A: 2 Mutations", i.e., 33Y,34N; 33Y,70D; 33Y,121F; 33Y,134R; 33Y,141P; 33Y,146G; 33Y,157L; 33Y,161A; 33Y,178F; 33Y,179T; 33Y,223E; 33Y,229P; 33Y,309P; 33Y,334P; 34N,70D; 34N,121F; 34N,134R; 34N,141P; 34N,146G; 34N,157L; 34N,161A; 34N,178F; 34N,179T; 34N,223E; 34N,229P; 34N,309P; 34N,334P; 70D,121F; 70D,134R; 70D,141P; 70D,146G; 70D,157L; 70D,161A; 70D,178F; 70D,179T; 70D,223E; 70D,229P; 70D,309P; 70D,334P; 121F,134R; 121F,141P; 121F,146G; 121F,157L; 121F,161A; 121F,178F; 121F,179T; 121F,223E; 121F,229P; 121F,309P; 121F,334P; 134R,141P; 134R,146G; 134R,157L; 134R,161A; 134R,178F; 134R,179T; 134R,223E; 134R,229P; 134R,309P; 134R,334P; 141P,146G; 141P,157L; 141P,161A; 141P,178F; 141P,179T; 141P,223E; 141P,229P; 141P,309P; 141P,334P; 146G,157L; 146G,161A; 146G,178F; 146G,179T; 146G,223E; 146G,229P; 146G,309P; 146G,334P; 157L,161A; 157L,178F; 157L,179T; 157L,223E; 157L,229P; 157L,309P; 157L,334P; 161A,178F; 161A,179T; 161A,223E; 161A,229P; 161A,309P; 161A,334P; 178F,179T; 178F,223E; 178F,229P; 178F,309P; 178F,334P; 179T,223E; 179T,229P; 179T,309P; 179T,334P; 223E,229P; 223E,309P; 223E,334P; 229P,309P; 229P,334P; or,309P,334P.

In other words, the PS4 variant polypeptide may comprise any of the following: 33Y,34N,307K/R/H; 33Y,70D,307K/R/H; 33Y,121F,307K/R/H; 33Y,134R,307K/R/H; 33Y,141P, 307K/R/H; 33Y,146G,307K/R/H; 33Y,157L,307K/R/H; 33Y,161A,307K/R/H; 33Y,178F,307K/R/H; 33Y,179T, 307K/R/H; 33Y,223E,307K/R/H; 33Y,229P,307K/R/H; 33Y, 309P,307K/R/H; 33Y,334P,307K/R/H; 34N,70D,307K/R/H; 34N,121F,307K/R/H; 34N,134R,307K/R/H; 34N,141P, 307K/R/H; 34N,146G,307K/R/H; 34N,157L,307K/R/H; 34N,161A,307K/R/H; 34N,178F,307K/R/H; 34N,179T, 307K/R/H; 34N,223E,307K/R/H; 34N,229P,307K/R/H; 34N,309P,307K/R/H; 34N,334P,307K/R/H; 70D,121F, 307K/R/H; 70D,134R,307K/R/H; 70D,141P,307K/R/H; 70D,146G,307K/R/H; 70D,157L,307K/R/H; 70D,161A, 307K/R/H; 70D,178F,307K/R/H; 70D,179T,307K/R/H; 70D,223E,307K/R/H; 70D,229P,307K/R/H; 70D,309P, 307K/R/H; 70D,334P,307K/R/H; 121F,134R,307K/R/H; 121F,141P,307K/R/H; 121F,146G,307K/R/H; 121F,157L, 307K/R/H; 121F,161A,307K/R/H; 121F,178F,307K/R/H; 121F,179T,307K/R/H; 121F,223E,307K/R/H; 121F,229P, 307K/R/H; 121F,309P,307K/R/H; 121F,334P,307K/R/H; 134R,141P,307K/R/H; 134R,146G,307K/R/H; 134R,157L, 307K/R/H; 134R,161A,307K/R/H; 134R,178F,307K/R/H; 134R,179T,307K/R/H; 134R,223E,307K/R/H; 134R,229P, 307K/R/H; 134R,309P,307K/R/H; 134R,334P,307K/R/H; 141P,146G,307K/R/H; 141P,157L,307K/R/H; 141P,161A, 307K/R/H; 141P,178F,307K/R/H; 141P,179T,307K/R/H; 141P,223E,307K/R/H; 141P,229P,307K/R/H; 141P,309P, 307K/R/H; 141P,334P,307K/R/H; 146G,157L,307K/R/H; 146G,161A,307K/R/H; 146G,178F,307K/R/H; 146G,179T, 307K/R/H; 146G,223E,307K/R/H; 146G,229P,307K/R/H; 146G,309P,307K/R/H; 146G,334P,307K/R/H; 157L,161A, 307K/R/H; 157L,178F,307K/R/H; 157L,179T,307K/R/H; 157L,223E,307K/R/H; 157L,229P,307K/R/H; 157L,309P, 307K/R/H; 157L,334P,307K/R/H; 161A,178F,307K/R/H; 161A,179T,307K/R/H; 161A,223E,307K/R/H; 161A,229P, 307K/R/H; 161A,309P,307K/R/H; 161A,334P,307K/R/H; 178F,179T,307K/R/H; 178F,223E,307K/R/H; 178F,229P, 307K/R/H; 178F,309P,307K/R/H; 178F,334P,307K/R/H; 179T,223E,307K/R/H; 179T,229P,307K/R/H; 179T,309P, 307K/R/H; 179T,334P,307K/R/H; 223E,229P,307K/R/H; 223E,309P,307K/R/H; 223E,334P,307K/R/H; 229P,309P, 307K/R/H; 229P,334P,307K/R/H; 309P,334P,307K/R/H.

The PS4 variant polypeptide may alternatively comprise, in addition to 307K/R/H, 3 further mutations at any of positions 33, 34, 70, 121, 134, 141, 146, 157, 161, 178, 179, 223, 229, 309 or 334, as shown in "Annex A: 3 Mutations".

The PS4 variant polypeptide may alternatively comprise, in addition to 307K/R/H, 4 further mutations at any of positions 33, 34, 70, 121, 134, 141, 146, 157, 161, 178, 179, 223, 229, 309 or 334, as shown in "Annex A: 4 Mutations".

The PS4 variant polypeptide may alternatively comprise, in addition to 307K/R/H, 5 further mutations at any of positions 33, 34, 70, 121, 134, 141, 146, 157, 161, 178, 179, 223, 229, 309 or 334, as shown in "Annex A: 5 Mutations".

The PS4 variant polypeptide may alternatively comprise, in addition to 307K/R/H, 6 further mutations at any of positions 33, 34, 70, 121, 134, 141, 146, 157, 161, 178, 179, 223, 229, 309 or 334, as shown in "Annex A: 6 Mutations".

The PS4 variant polypeptide may alternatively comprise, in addition to 307K/R/H, 7 further mutations at any of positions 33, 34, 70, 121, 134, 141, 146, 157, 161, 178, 179, 223, 229, 309 or 334, as shown in "Annex A: 7 Mutations".

The PS4 variant polypeptide may comprise, a sequence with 9 mutations, viz each of the following residues 33Y, 34N, 70D, 121F, 134R, 141P, 146G, 157L, 161A, 178F, 179T, 223E, 229P, 307K/R/H, 309P, 334P, but not including the septets of residues shown in "Annex A: 7 Mutations".

The PS4 variant polypeptide may comprise, a sequence with 10 mutations, viz each of the following residues 33Y, 34N, 70D, 121F, 134R, 141P, 146G, 157L, 161A, 178F, 179T, 223E, 229P, 307K/R/H, 309P, 334P, but not including the sextets of residues shown in "Annex A: 6 Mutations".

The PS4 variant polypeptide may comprise, a sequence with 11 mutations, viz each of the following residues 33Y, 34N, 70D, 121F, 134R, 141P, 146G, 157L, 161A, 178F, 179T, 223E, 229P, 307K/R/H, 309P, 334P, but not including the quintets of residues shown in "Annex A: 5 Mutations".

The PS4 variant polypeptide may comprise, a sequence with 12 mutations, viz each of the following residues 33Y, 34N, 70D, 121F, 134R, 141P, 146G, 157L, 161A, 178F, 179T, 223E, 229P, 307K/R/H, 309P, 334P, but not including the quadruplets of residues shown in "Annex A: 4 Mutations".

The PS4 variant polypeptide may comprise, a sequence with 13 mutations, viz each of the following residues 33Y, 34N, 70D, 121F, 134R, 141P, 146G, 157L, 161A, 178F, 179T, 223E, 229P, 307K/R/H, 309P, 334P, but not including the triplets of residues shown in "Annex A: 3 Mutations".

The PS4 variant polypeptide may comprise, a sequence with 14 mutations, viz each of the following residues 33Y, 34N, 70D, 121F, 134R, 141P, 146G, 157L, 161A, 178F, 179T, 223E, 229P, 307K/R/H, 309P, 334P, but not including the pairs of residues shown in "Annex A: 2 Mutations".

The PS4 variant polypeptide may comprise, a sequence with 15 mutations, viz each of the following residues 33Y, 34N, 70D, 121F, 134R, 141P, 146G, 157L, 161A, 178F, 179T, 223E, 229P, 307K/R/H, 309P, 334P, but not including the single residues shown in "Annex A: 1 Mutations".

Preferred PS4 Variant Polypeptide Sequences

Preferably, however, the PS4 variant polypeptide further comprises mutations at each of these positions.

We specifically provide for a PS4 variant polypeptide derivable from a parent polypeptide having non-maltogenic exoamylase activity, in which the PS4 variant polypeptide comprises a mutation at each of the following positions 33, 34, 70, 121, 134, 141, 146, 157, 161, 178, 179, 223, 229, 307, 309, 334, with reference to the position numbering of a *Pseudomonas saccharophilia* exoamylase sequence shown as SEQ ID NO: 1.

In preferred embodiments, the position 307 mutation comprises a basic or positively charged residue. In some embodiments, the position 307 mutation comprises 307K or 307R. In another preferred embodiment, the position 307 residue is H. We therefore provide for a PS4 variant polypeptide derivable from a parent polypeptide having non-maltogenic exoamylase activity, in which the PS4 variant polypeptide comprises a mutation at position 307 to K or R, or in which the position 307 residue is H, together with mutations at each of position 33, 34, 70, 121, 134, 141, 146, 157, 161, 178, 179, 223, 229, 307, 309, 334.

Preferably, the position 33 residue may comprise Y, preferably 33Y, more preferably N33Y. Preferably, the position 34 residue may comprise N, preferably 34N, more preferably D34N. Preferably, the position 70 residue may comprise D, preferably 70D, more preferably G70D. Preferably, the position 121 residue may comprise F, preferably 121F, more preferably G121F. Preferably, the position 134 residue may comprise R, preferably 134R, more preferably G134R. Preferably, the position 141 residue may comprise P, preferably 141P, more preferably A141P. Preferably, the position 146 residue may comprise G, preferably 146G, more preferably Y146G. Preferably, the position 157 residue may comprise L, preferably 157L, more preferablyI 157L. Preferably, the position 161 residue may comprise A, preferably 161A, more preferably S161A. Preferably, the position 178 residue may comprise F, preferably 178F, more preferably L178F. Preferably, the position 179 residue may comprise T, preferably 179T, more preferably A179T. Preferably, the position 223 residue may comprise E, preferably 223E, more preferably G223E. Preferably, the position 229 residue may comprise P, preferably 229P, more preferably S229P. Preferably, the position 307 residue may comprise K, preferably 307K, more preferably H307K. Preferably, the position 309 residue may comprise P, preferably 309P, more preferably A309P. Preferably, the position 334 residue may comprise P, preferably 334P, more preferably S334P.

As noted above, in preferred embodiments the position 70 mutation is 70D, preferably G70D. We therefore provide for a PS4 variant polypeptide derivable from a parent polypeptide having non-maltogenic exoamylase activity, in which the PS4 variant polypeptide comprises a mutation at position 307 to K or R, or in which the position 307 residue is H, and a mutation at position 70 to 70D, together with mutations at each of position 33, 34, 121, 134, 141, 146, 157, 161, 178, 179, 223, 229, 307, 309, 334.

In preferred embodiments, the residue at position 272 is "wild type", i.e., unmutated. The position 272 residue is therefore preferably histidine (H). We therefore provide for a PS4 variant polypeptide derivable from a parent polypeptide having non-maltogenic exoamylase activity, in which the PS4 variant polypeptide comprises a mutation at position 307 to K or R, or in which the position 307 residue is H, and a mutation at position 70 to 70D, in which the position 272 residue is H, together with mutations at each of position 33, 34, 121, 134, 141, 146, 157, 161, 178, 179, 223, 229, 307, 309, 334.

Similarly, the residue at position 303 is "wild type" or unmutated, and is preferably glycine (G) in other preferred embodiments. We therefore provide for a PS4 variant polypeptide derivable from a parent polypeptide having non-maltogenic exoamylase activity, in which the PS4 variant polypeptide comprises a mutation at position 307 to K or R, or in which the position 307 residue is H, and a mutation at position 70 to 70D, in which the position 303 residue is G, together with mutations at each of position 33, 34, 121, 134, 141, 146, 157, 161, 178, 179, 223, 229, 307, 309, 334.

In preferred embodiments, in each of the above embodiments of the PS4 variant polypeptide which comprise further mutations at positions 33, 34, 70, 121, 134, 141, 146, 157, 161, 178, 179, 223, 229, 309, 334, the position 33 residue is preferably Y, the position 34 residue is preferably N, the position 70 residue is preferably D, the position 121 residue is preferably F, the position 134 residue is preferably R, the position 141 residue is preferably P, the position 146 residue is preferably G, the position 157 residue is preferably L, the position 161 residue is preferably A, the position 178 residue is preferably F, the position 179 residue is preferably T, the position 223 residue is preferably E, the position 229 residue is preferably P, the position 309 residue is preferably P, and the position 334 residue is preferably P.

In highly preferred embodiments, we provide a PS4 variant polypeptide which comprises the following residues 33Y, 34N, 70D, 121F, 134R,141P, 146G, 157L, 161A, 178F,179T, 223E, 229P, 307K/R/H, 309P, 334P. The PS4 variant polypeptide may comprise each of the following mutations N33Y, D34N, G70D, G121F, G134R, A141P, Y146G, I157L, S161A, L178F, A179T, G223E, S229P, H307K/R, A309P and S334P.

We specifically provide for a PS4 variant polypeptide which comprises the following substitutions 33Y, 34N, 70D, 121F, 134R, 141P, 146G, 157L, 161A, 178F, 179T, 223E, 229P, 307K, 309P, 334P, preferably N33Y, D34N, G70D, G121F, G134R, A141P, Y146G, I157L, S161A, L178F, A179T, G223E, S229P, H307K, A309P, S334P relative to a *Pseudomonas saccharophilia* exoamylase sequence shown as SEQ ID NO: 1. In such an embodiment, the PS4 variant polypeptide may comprise a sequence SEQ ID NO: 21.

We further provide for a PS4 variant polypeptide which comprises the following substitutions 33Y, 34N, 70D, 121F, 134R, 141P, 146G, 157L, 161A, 178F, 179T, 223E, 229P, 307R, 309P, 334P, preferably N33Y, D34N, G70D, G121F, G134R, A141P, Y146G, I157L, S161A, L178F, A179T, G223E, S229P, H307R, A309P, S334P relative to a *Pseudomonas saccharophilia* exoamylase sequence shown as SEQ ID NO: 1. In such an embodiment, the PS4 variant polypeptide may comprise a sequence SEQ ID NO: 23.

We further provide for a PS4 variant polypeptide derivable from a parent polypeptide having non-maltogenic exoamylase activity, in which the PS4 variant polypeptide comprises the following substitutions 33Y, 34N, 70D, 121F, 134R, 141P, 146G, 157L, 161A, 178F, 179T, 223E, 229P, 309P, 334P, preferably N33Y, D34N, G70D, G121F, G134R, A141P, Y146G, I157L, S161A, L178F, A179T, G223E, S229P, A309P, S334P relative to a *Pseudomonas saccharophilia* exoamylase sequence shown as SEQ ID NO: 1. In such an embodiment, the PS4 variant polypeptide may comprise a sequence SEQ ID NO: 25.

Further Substitutions

One or more other mutations as set out in the table below may further be present in the PS4 variant polypeptide described here.

| Position | Mutation | Substitution |
|---|---|---|
| 3 | 3S | A3S |
| 26 | 26E, 26D | N26E, N26D |
| 34 | 34N, 34G, 34A, 34S or 34T | D34N, D34G, D34A, D34S or D34T |
| 46 | 46G | I46G |
| 87 | 87S | G87S |
| 121 | 121F, 121Y, 121W, 121H, 121A, 121M, 121S, 121T, 121D, 121E, 121L, 121K, 121V | G121F, G121Y, G121W, G121H, G121A, G121M, G121G, G121S, G121T, G121D, G121E, G121L, G121K, G121V |
| 145 | 145D | N145D |
| 146 | 146M, 146G | Y146M, Y146G |
| 157 | 157L, 157M, 157V, 157N, 157L | I157L, I157M, I157V, I157N, I157L |
| 158 | 158T, 158A, 158S | G158T, G158A, G158S |
| 160 | 160D | L160D |
| 179 | 179T, 179V | A179T, A179V |
| 188 | 188, 188S, 188T or 188H | G188, G188S, G188T, G188H |
| 198 | 198W, 198F | Y198W, Y198F |
| 179 | 179T | A179T |
| 223 | 223A, 223E, 223K, 223L, 223I, 223S, 223T, 223V, 223R, 223P, 223D | G223A, G223E, G223K, G223L, G223I, G223S, G223T, G223V, G223R, G223P, G223D |
| 272 | 272Q | H272Q |
| 303 | 303E, 303D | G303E, G303D |
| 306 | 306T, 306G, 306T, 306G | H306T, H306G, H306T, H306G |
| 316 | 316S, 316P, 316K, 316Q | R316S, R316P, R316K, R316Q |
| 339 | 339A, 339E | W339A, W339E |
| 353 | 353T | R353T |

PS4 Variant Nucleic Acids

We also describe PS4 nucleic acids having sequences which correspond to or encode the alterations in the PS4 variant polypeptide sequences, for use in producing such polypeptides for the purposes described here. Thus, we provide nucleic acids capable of encoding any polypeptide sequence set out in this document.

The skilled person will be aware of the relationship between nucleic acid sequence and polypeptide sequence, in particular, the genetic code and the degeneracy of this code, and will be able to construct such PS4 nucleic acids without difficulty. For example, he will be aware that for each amino acid substitution in the PS4 variant polypeptide sequence, there may be one or more codons which encode the substitute amino acid. Accordingly, it will be evident that, depending on the degeneracy of the genetic code with respect to that particular amino acid residue, one or more PS4 nucleic acid sequences may be generated corresponding to that PS4 variant polypeptide sequence. Furthermore, where the PS4 variant polypeptide comprises more than one substitution, for example H307K/G70D, the corresponding PS4 nucleic acids may comprise pairwise combinations of the codons which encode respectively the two amino acid changes.

The PS4 variant nucleic acid sequences may be derivable from parent nucleic acids which encode any of the parent polypeptides described above. In particular, parent nucleic acids may comprise wild type sequences, e.g., SEQ ID NO: 6 or SEQ ID NO: 12. The PS4 variant nucleic acids may therefore comprise nucleic acids encoding wild type non-maltogenic exoamylases, but which encode another amino acid at the relevant position instead of the wild type amino acid residue. The PS4 variant nucleic acid sequences may also comprise wild type sequences with one or more mutations, e.g., which encode parent polypeptides described above under "Combinations".

It will be understood that nucleic acid sequences which are not identical to the particular PS4 variant nucleic acid sequences, but are related to these, will also be useful for the methods and compositions described here, such as a variant, homologue, derivative or fragment of a PS4 variant nucleic acid sequence, or a complement or a sequence capable of hybridising thereof. Unless the context dictates otherwise, the term "PS4 variant nucleic acid" should be taken to include each of these entities listed above.

Mutations in amino acid sequence and nucleic acid sequence may be made by any of a number of techniques, as known in the art. Variant sequences may easily be made using any of the known mutagenesis techniques, for example, site directed mutagenesis using PCR with appropriate oligonucleotide primers, 5' add-on mutagenesis, mismatched primer mutagenesis, etc. Alternatively, or in addition, the PS4 variant nucleic acid sequences may be made de novo.

In particularly preferred embodiments, the mutations are introduced into parent sequences by means of PCR (polymerase chain reaction) using appropriate primers, as illustrated in the Examples. It is therefore possible to alter the sequence of a polypeptide by introducing any desired amino acid substitutions into a parent polypeptide, preferably having non-maltogenic exoamylase activity, such as into a *Pseudomonas saccharophilia* or a *Pseudomonas stutzeri* exoamylase sequence at amino acid or nucleic acid level, as described. We describe a method in which the sequence of a non-maltogenic exoamylase is altered by altering the sequence of a nucleic acid which encodes the non-maltogenic exoamylase.

However, it will of course be appreciated that the PS4 variant polypeptide does not need in fact to be actually derived from a wild type polypeptide or nucleic acid sequence by, for example, step by step mutation. Rather, once the sequence of the PS4 variant polypeptide is established, the skilled person can easily make that sequence from the wild type with all the mutations, via means known in the art, for example, using appropriate oligonucleotide primers and PCR. In fact, the PS4 variant polypeptide can be made de novo with all its mutations, through, for example, peptide synthesis methodology.

In general, however, the PS4 variant polypeptides and/or nucleic acids are derived or derivable from a "precursor" sequence. The term "precursor" as used herein means an enzyme that precedes the enzyme which is modified according to the methods and compositions described here. A precursor therefore includes an enzyme used to produce a modified enzyme. Thus, the precursor may be an enzyme that is modified by mutagenesis as described elsewhere in this document. Likewise, the precursor may be a wild type enzyme, a variant wild type enzyme or an already mutated enzyme.

The PS4 variant polypeptides and nucleic acids may be produced by any means known in the art. Specifically, they may be expressed from expression systems, which may be in vitro or in vivo in nature. Specifically, we describe plasmids and expression vectors comprising PS4 nucleic acid sequences, preferably capable of expressing PS4 variant polypeptides. Cells and host cells which comprise and are preferably transformed with such PS4 nucleic acids, plasmids and vectors are also disclosed, and it should be made clear that these are also encompassed in this document.

The PS4 variant polypeptides may for example be made using site directed mutagenesis using PCR with appropriate oligonucleotide primers, 5' add-on mutagenesis, mismatched primer mutagenesis, etc as described Example 4A. In order to produce PS4 variant polypeptides with mutations at positions 307, for example, a nucleic acid sequence corresponding to a pSac-pMD229 sequence; *Pseudomonas saccharophila* maltotetrahydrolase nucleotide sequence with 17 substitutions and deletion of the starch binding domain (SEQ ID NO: 14) may be made and the relevant changes introduced. The skilled reader will be aware, however, that any suitable starting sequence can be used, and indeed that it is possible to start from a wild type exoamylase sequence to get to the desired variant polypeptide either in a single step, or via other intermediate sequences.

In preferred embodiments, the PS4 variant polypeptide sequence is used as a food additive in an isolated form. The term "isolated" means that the sequence is at least substantially free from at least one other component with which the sequence is naturally associated in nature and as found in nature. In one aspect, preferably the sequence is in a purified form. The term "purified" means that the sequence is in a relatively pure state—e.g. at least about 90% pure, or at least about 95% pure or at least about 98% pure.

In highly preferred embodiments, the nucleic acid sequence comprises the sequences shown in SEQ ID NO: 22, 24 or 26.

Position Numbering

All positions referred to in the present document by numbering refer to the numbering of a *Pseudomonas saccharophilia* exoamylase reference sequence shown below (SEQ ID NO: 1):

```
  1 DQAGKSPAGV RYHGGDEIIL QGFHWNVVRE APNDWYNILR QQASTIAADG FSAIWMPVPW

61 RDFSSWTD GG KSGGGEGYFW HDFNKNGRYG SDAQLRQAAG ALGGAGVKVL YDVVPNHMNR

121 GYPDKEINLP AGQGFWRNDC ADPGNYPNDC DDGDRFIGGE SDLNTGHPQI YGMFRDELAN

181 LRSGYGAGGF RFDFVRGYAP ERVDSWMSDS ADSSFCVGEL WK GPSEYPSW DWRNTASWQQ

241 IIKDWSDRAK CPVFDFALKE RMQNGSV ADW KHGLNGNPDP RWREVAVTFV DNHDTGYSPG

301 QNGGQHHWAL QD GLIRQAYA YILTSPGTPV VYWSHMYDWG YGDFIRQLIQ VRRTAGVRAD

361 SAISFHSGYS GLVATVSGSQ QTLVVALNSD LANPGQVA SG SFSEAVNASN GQVRVWRSGS

421 GDGGGNDGGE GGLVNVNFRC DNGVTQMGDS VYAVGNVSQL GNWSPASAVR LTDTSSYPTW

481 KGSIALPDGQ NVEWKCLIRN EADATLVRQW QSGGNNQVQA AAGASTSGSF
```

The reference sequence is derived from the *Pseudomonas saccharophila* sequence having SWISS-PROT accession number P22963, but without the signal sequence MSHILRAAVLAAVLLPFPALA (SEQ ID NO: 33).

The C-terminal starch binding domain EGGLVNVNFR CDNGVTQMGD SVYAVGNVSQ LGNWSPASAV RLTDTSSYPT WKGSIALPDG QNVEWKCLIR NEADATLVRQ WQSGGNNQVQ AAAGASTSGS F (SEQ ID NO: 34) may optionally be deleted or disregarded. Alternatively, it may be included in the PS4 variant polypeptide sequence.

In the context of the present description a specific numbering of amino acid residue positions in PS4 exoamylase enzymes is employed. In this respect, by alignment of the amino acid sequences of various known exoamylases it is possible to unambiguously allot a exoamylase amino acid position number to any amino acid residue position in any exoamylase enzyme, the amino acid sequence of which is known. Using this numbering system originating from for example the amino acid sequence of the exoamylase obtained from *Pseudomonas saccharophilia*, aligned with amino acid sequences of a number of other known exoamylase, it is possible to indicate the position of an amino acid residue in a exoamylase unambiguously.

Therefore, the numbering system, even though it may use a specific sequence as a base reference point, is also applicable to all relevant homologous sequences. For example, the position numbering may be applied to homologous sequences from other *Pseudomonas* species, or homologous sequences from other bacteria. Preferably, such homologues have 60% or greater homology, for example 70% or more, 80% or more, 90% or more or 95% or more homology, with the reference sequence SEQ ID NO: 1 above, or the sequences having SWISS-PROT accession numbers P22963 or P13507, preferably with all these sequences. Sequence homology between proteins may be ascertained using well known alignment programs and hybridisation techniques described herein. Such homologous sequences, as well as the functional equivalents described below, will be referred to in this document as the "PS4 Family".

Furthermore, and as noted above, the numbering system used in this document makes reference to a reference sequence SEQ ID NO: 1, which is derived from the *Pseudomonas saccharophila* sequence having SWISS-PROT accession number P22963, but without the signal sequence MSHILRAAVLAAVLLPFPALA (SEQ ID NO: 33). This signal sequence is located N terminal of the reference sequence and consists of 21 amino acid residues. Accordingly, it will be trivial to identify the particular residues to be mutated or substituted in corresponding sequences comprising the signal sequence, or indeed, corresponding sequences comprising any other N- or C-terminal extensions or deletions. In relation to N-terminal additions or deletions, all that is required is to offset the position numbering by the number of residues inserted or deleted. For example, position 1 in SEQ ID NO: 1 corresponds to position 22 in a sequence with the signal sequence.

Parent Enzyme/Polypeptide

The PS4 variant polypeptides are derived from, or are variants of, another sequence, known as a "parent enzyme", a "parent polypeptide" or a "parent sequence".

The term "parent enzyme" as used in this document means the enzyme that has a close, preferably the closest, chemical structure to the resultant variant, i.e., the PS4 variant polypeptide or nucleic acid. The parent enzyme may be a precursor enzyme (i.e. the enzyme that is actually mutated) or it may be prepared de novo. The parent enzyme may be a wild type enzyme, or it may be a wild type enzyme comprising one or more mutations.

The term "precursor" as used herein means an enzyme that precedes the enzyme which is modified to produce the enzyme. Thus, the precursor may be an enzyme that is modified by mutagenesis. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally and contrasting with the phenotype of a mutant. Thus, in the present context, the wild type enzyme is a form of the enzyme naturally found in most members of the relevant species.

Generally, the relevant wild type enzyme in relation to the variant polypeptides described here is the most closely related corresponding wild type enzyme in terms of sequence homology. However, where a particular wild type sequence has been used as the basis for producing a variant PS4 polypeptide as described here, this will be the corresponding wild type sequence regardless of the existence of another wild type sequence that is more closely related in terms of amino acid sequence homology.

The parent enzyme or polypeptide can be any suitable starting polypeptide. It may preferably have some enzymatic activity. Preferably, this enzymatic activity is an amylase activity. More preferably, the parent polypeptide comprises exoamylase activity.

The parent enzyme is preferably a polypeptide which preferably exhibits non-maltogenic exoamylase activity. Preferably, the parent enzyme is a non-maltogenic exoamylase itself. For example, the parent enzyme may be a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507.

Other members of the PS4 family may be used as parent enzymes; such "PS4 family members" will generally be similar to, homologous to, or functionally equivalent to either of these two enzymes, and may be identified by standard methods, such as hybridisation screening of a suitable library using probes, or by genome sequence analysis.

In particular, functional equivalents of either of these two enzymes, as well as other members of the "PS4 family" may also be used as starting points or parent polypeptides for the generation of PS4 variant polypeptides as described here.

A "functional equivalent" of a protein means something that shares one or more, preferably substantially all, of the functions of that protein. Preferably, such functions are biological functions, preferably enzymatic functions, such as amylase activity, preferably non-maltogenic exoamylase activity. Such functions may include any property of the protein, including exo-specificity, thermostability, and improved handling such as firmness, resilience, cohesiveness, crumbliness and foldability (as described below).

In relation to a parent enzyme, the term "functional equivalent" preferably means a molecule having similar or identical function to a parent molecule. The parent molecule may be a *Pseudomonas saccharophila* non-maltogenic exoamylase or a *Pseudomonas stutzeri* non-maltogenic exoamylase or a polypeptide obtained from other sources.

The term "functional equivalent" in relation to a parent enzyme being a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507 means that the functional equivalent could be obtained from other sources. The functionally equivalent enzyme may have a different amino acid sequence but will have non-maltogenic exoamylase activity. Examples of assays to determine functionality are described herein and are known to one skilled in the art.

In highly preferred embodiments, the functional equivalent will have sequence homology to either of the *Pseudomonas saccharophila* and *Pseudomonas stutzeri* non-maltogenic exoamylases mentioned above, preferably both. The functional equivalent may also have sequence homology with any of the sequences set out as SEQ ID NOs: 1 to 14, preferably SEQ ID NO: 1 or SEQ ID NO: 7 or both. Sequence homology between such sequences is preferably at least 60%, preferably 65% or more, preferably 75% or more, preferably 80% or more, preferably 85% or more, preferably 90% or more, preferably 95% or more. Such sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

In other embodiments, the functional equivalents will be capable of specifically hybridising to any of the sequences set out above. Methods of determining whether one sequence is capable of hybridising to another are known in the art, and are for example described in Sambrook, et al (supra) and Ausubel, F. M. et al. (supra). In highly preferred embodiments, the functional equivalents will be capable of hybridising under stringent conditions, e.g. 65° C. and 0.1×SSC {1×SSC=0.15 M NaCl, 0.015 M Na$_3$ Citrate pH 7.0}.

For example, functional equivalents which have sequence homology to *Pseudomonas saccharophila* and *Pseudomonas stutzeri* non-maltogenic exoamylases are suitable for use as parent enzymes. Such sequences may differ from the *Pseudomonas saccharophila* sequence at any one or more positions. Furthermore, non-maltogenic exoamylases from other strains of *Pseudomonas* spp, such as ATCC17686, may also be used as a parent polypeptide. The PS4 variant polypeptide residues may be inserted into any of these parent sequences to generate the variant PS4 polypeptide sequences.

It will be understood that where it is desired for PS4 variant polypeptides to additionally comprise one or more mutations, as set out above, corresponding mutations may be made in the nucleic acid sequences of the functional equivalents of *Pseudomonas* spp non-maltogenic exoamylase, as well as other members of the "PS4 family", in order that they may be used as starting points or parent polypeptides for the generation of PS4 variant polypeptides as described here.

Specifically included within the term "PS4 variant polypeptides" are the polypeptides disclosed in: U.S. 60/485,413, 60/485,539 and 60/485,616; PCT/US2004/021723 and PCT/US2004/021739; U.S. Ser. No. 10/886,905 and 10/866,903; U.S. 60/608,919; U.S. 60/612,407; U.S. 60/485,539; PCT/IB2004/002487; U.S. Ser. No. 10/886,023; 10/886,505, 10/886,527 and 10/886,504; 10/947,612. These documents however are not admitted to be prior art.

Such polypeptides are suitable for use in the applications described herein, in particular, as food additives, to treat starch as described, to prepare a food product, to make a bakery product, for the formulation of improver compositions, for the formulation of combinations, etc.

Modification of Parent Sequences

The parent enzymes may be modified at the amino acid level or the nucleic acid level to generate the PS4 variant sequences described here. Therefore, we provide for the generation of PS4 variant polypeptides by introducing one or more corresponding codon changes in the nucleotide sequence encoding a non-maltogenic exoamylase polypeptide.

The nucleic acid numbering should preferably be with reference to the position numbering of a *Pseudomonas saccharophilia* exoamylase nucleotide sequence shown as SEQ ID NO: 6. Alternatively, or in addition, reference may be made to the sequence with GenBank accession number X16732. In preferred embodiments, the nucleic acid numbering should be with reference to the nucleotide sequence shown as SEQ ID NO: 6. However, as with amino acid residue numbering, the residue numbering of this sequence is to be used only for reference purposes only. In particular, it will be appreciated that the above codon changes can be made in any PS4 family nucleic acid sequence. For example, sequence changes can be made to a *Pseudomonas saccharophila* or a *Pseudomonas stutzeri* non-maltogenic exoamylase nucleic acid sequence (e.g., X16732, SEQ ID NO: 6 or M24516, SEQ ID NO: 12).

The parent enzyme may comprise the "complete" enzyme, i.e., in its entire length as it occurs in nature (or as mutated), or it may comprise a truncated form thereof. The PS4 variant derived from such may accordingly be so truncated, or be "full-length". The truncation may be at the N-terminal end, or the C-terminal end, preferably the C-terminal end. The parent enzyme or PS4 variant may lack one or more portions, such as sub-sequences, signal sequences, domains or moieties, whether active or not etc. For example, the parent enzyme or the PS4 variant polypeptide may lack a signal sequence, as described above. Alternatively, or in addition, the parent enzyme or the PS4 variant may lack one or more catalytic or binding domains.

In highly preferred embodiments, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophilia* non-maltogenic exoamylase shown as SEQ ID NO: 1. It is to be noted that this is the case for the PS4 variants pSac-pMS382, pSac-pMS382R and pSac-pMS382H.

In other embodiments, the parent enzyme or PS4 variant may comprise a e "complete" enzyme, i.e., in its entire length as it occurs in nature (or as mutated), together with one or more additional amino acid sequences at the N terminus or C terminus. For example, the parent enzyme or PS4 variant polypeptide may comprise a single extra amino acid residue at the C terminus or N terminus, e.g., M, A, G, etc. Preferably, the additional amino acid residue is present at the N terminus. Where one or more additional residues is included, the position numbering will be offset by the length of the addition.

Amylase

The PS4 variant polypeptides generally comprise amylase activity.

The term "amylase" is used in its normal sense—e.g. an enzyme that is inter alia capable of catalysing the degradation of starch. In particular they are hydrolases which are capable of cleaving α-D-(1→4) O-glycosidic linkages in starch.

Amylases are starch-degrading enzymes, classified as hydrolases, which cleave α-D-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (E.C. 3.2.1.2, α-D-(1→4)-glucan maltohydrolase), and some product-specific amylases like maltogenic alpha-amylase (E.C. 3.2.1.133) cleave the starch molecule from the non-reducing end of the substrate. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce malto-oligosaccharides of a specific length from starch.

Non-Maltogenic Exoamylase

The PS4 variant polypeptides described in this document are derived from (or variants of) polypeptides which preferably exhibit non-maltogenic exoamylase activity. Preferably, these parent enzymes are non-maltogenic exoamylases themselves. The PS4 variant polypeptides themselves in highly preferred embodiments also exhibit non-maltogenic exoamylase activity.

In highly preferred embodiments, the term "non-maltogenic exoamylase enzyme" as used in this document should be taken to mean that the enzyme does not initially degrade starch to substantial amounts of maltose as analysed in accordance with the product determination procedure as described in this document.

In highly preferred embodiments, the non-maltogenic exoamylase comprises an exo-maltotetraohydrolase. Exo-maltotetraohydrolase (E.C.3.2.1.60) is more formally known as glucan 1,4-alpha-maltotetrahydrolase. This enzyme hydrolyses 1,4-alpha-D-glucosidic linkages in amylaceous polysaccharides so as to remove successive maltotetraose residues from the non-reducing chain ends.

Non-maltogenic exoamylases are described in detail in U.S. Pat. No. 6,667,065, hereby incorporated by reference.

Assays for Non-Maltogenic Exoamylase Activity

The following system is used to characterize polypeptides having non-maltogenic exoamylase activity which are suitable for use according to the methods and compositions described here. This system may for example be used to characterise the PS4 parent or variant polypeptides described here.

By way of initial background information, waxy maize amylopectin (obtainable as WAXILYS 200 from Roquette, France) is a starch with a very high amylopectin content (above 90%). 20 mg/ml of waxy maize starch is boiled for 3 min. in a buffer of 50 mM MES (2-(N-morpholino)ethanesulfonic acid), 2 mM calcium chloride, pH 6.0 and subsequently incubated at 50° C. and used within half an hour.

One unit of the non-maltogenic exoamylase is defined as the amount of enzyme which releases hydrolysis products equivalent to 1 µmol of reducing sugar per min. when incubated at 50 degrees C. in a test tube with 4 ml of 10 mg/ml waxy maize starch in 50 mM MES, 2 mM calcium chloride, pH 6.0 prepared as described above. Reducing sugars are measured using maltose as standard and using the dinitrosalicylic acid method of Bernfeld,*Methods Enzymol.*, (1954), 1, 149-158 or another method known in the art for quantifying reducing sugars.

The hydrolysis product pattern of the non-maltogenic exoamylase is determined by incubating 0.7 units of non-maltogenic exoamylase for 15 or 300 min. at 50° C. in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligosaccharides of from glucose to maltoheptaose as standards. The response factor used for maltooctaose to maltodecaose is the response factor found for maltoheptaose.

Preferably, the PS4 variant polypeptides have non-maltogenic exoamylase activity such that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-morpholino) ethane sulfonic acid and 2 mM calcium chloride then the enzyme would yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis products would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50C at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "Waxy Maize Starch Incubation Test".

Thus, alternatively expressed, preferred PS4 variant polypeptides which are non-maltogenic exoamylases are characterised as having the ability in the waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

The hydrolysis products in the waxy maize starch incubation test may include one or more linear malto-oligosaccharides of from two to ten D-glucopyranosyl units and optionally glucose. The hydrolysis products in the waxy maize starch incubation test may also include other hydrolytic products. Nevertheless, the % weight amounts of linear maltooligosaccharides of from three to ten D-glucopyranosyl units are based on the amount of the hydrolysis product that consists of one or more linear malto-oligosaccharides of from two to ten D-glucopyranosyl units and optionally glucose. In other words, the % weight amounts of linear maltooligosaccharides of from three to ten D-glucopyranosyl units are not based on the amount of hydrolysis products other than one or more linear malto-oligosaccharides of from two to ten D-glucopyranosyl units and glucose.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

For ease of reference, and for the present purposes, the feature of analysing the hydrolysis product(s) using anion exchange HPLC using a Dionex PA 100 column with pulsed amperometric detection and with known linear maltooligosaccharides of from glucose to maltoheptaose used as standards, can be referred to as "analysing by anion exchange". Of course, and as just indicated, other analytical techniques would suffice, as well as other specific anion exchange techniques.

Thus, alternatively expressed, a preferred PS4 variant polypeptide is one which has non-maltogenic exoamylase such that it has the ability in a waxy maize starch incubation test to yield hydrolysis product(s) that would consist of one or more linear malto-oligosaccharides of from two to ten D-glucopyranosyl units and optionally glucose, said hydrolysis products being capable of being analysed by anion exchange; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

As used herein, the term "linear malto-oligosaccharide" is used in the normal sense as meaning 2-10 units of α-D-glucopyranose linked by an α-(1→4) bond.

In highly preferred embodiments, the PS4 polypeptides described here have improved exoamylase activity, preferably non-maltogenic exoamylase activity, when compared to the parent polypeptide, preferably when tested under the same conditions. In particular, in highly preferred embodiments, the PS4 variant polypeptides have 10% or more, preferably 20% or more, preferably 50% or more, exoamylase activity compared to their parents, preferably when measured in a waxy maize starch test.

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

As used herein, the term "linear malto-oligosaccharide" is used in the normal sense as meaning 2-20 units of α-D-glucopyranose linked by an α-(1→4) bond.

Improved Handling Properties

The PS4 variants described here preferably have improved properties when compared to their parent enzymes, such as any one or more of improved thermostability, improved pH stability, or improved exo-specificity. The PS4 variants described here preferably also have improved handling properties, such that a food product treated with a the PS4 variant polypeptide has any one or all of lower firmness, higher resilience, higher cohesiveness, lower crumbliness, or higher foldability compared to a food product which has been treated with a parent polypeptide or a wild type polypeptide.

Without wishing to be bound by any particular theory, we believe that the mutations at the particular positions have individual and cumulative effects on the properties of a polypeptide comprising such mutations.

Thermostability and pH Stability

Preferably, the PS4 variant polypeptide is thermostable; preferably, it has higher thermostability than its parent enzyme.

In wheat and other cereals the external side chains in amylopectin are in the range of DP 12-19. Thus, enzymatic hydrolysis of the amylopectin side chains, for example, by PS4 variant polypeptides as described having non-maltogenic exoamylase activity, can markedly reduce their crystallisation tendencies.

Starch in wheat and other cereals used for baking purposes is present in the form of starch granules which generally are resistant to enzymatic attack by amylases. Thus starch modification is mainly limited to damaged starch and is progressing very slowly during dough processing and initial baking until gelatinisation starts at about 60 C. As a consequence hereof only amylases with a high degree of thermostability are able to modify starch efficiently during baking. And generally the efficiency of amylases is increased with increasing thermostability. That is because the more thermostable the enzyme is the longer time it can be active during baking and thus the more antistaling effect it will provide.

Accordingly, the use of PS4 variant polypeptides as described here when added to the starch at any stage of its processing into a food product, e.g., before during or after baking into bread can retard or impede or slow down the retrogradation. Such use is described in further detail below.

As used herein the term "thermostable" relates to the ability of the enzyme to retain activity after exposure to elevated temperatures. Preferably, the PS4 variant polypeptide is capable of degrading starch at temperatures of from about 55° C. to about 80° C. or more. Suitably, the enzyme retains its activity after exposure to temperatures of up to about 95° C.

The thermostability of an enzyme such as a non-maltogenic exoamylase is measured by its half life. Thus, the PS4 variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C.

As used here, the half life (t½) is the time (in minutes) during which half the enzyme activity is inactivated under defined heat conditions. In preferred embodiments, the half life is assayed at 80 degrees C. Preferably, the sample is heated for 1-10 minutes at 80° C. or higher. The half life value is then calculated by measuring the residual amylase activity, by any of the methods described here. Preferably, a half life assay is conducted as described in more detail in the Examples.

Preferably, the PS4 variants described here are active during baking and hydrolyse starch during and after the gelatinization of the starch granules which starts at tempera-tures of about 55° C. The more thermostable the non-maltogenic exoamylase is the longer time it can be active and thus the more antistaling effect it will provide. However, during baking above temperatures of about 85° C., enzyme inactivation can take place. If this happens, the non-maltogenic exoamylase may be gradually inactivated so that there is substantially no activity after the baking process in the final bread. Therefore preferentially the non-maltogenic exoamylases suitable for use as described have an optimum temperature above 50° C. and below 98° C.

The thermostability of the PS4 variants described here can be improved by using protein engineering to become more thermostable and thus better suited for the uses described here; we therefore encompass the use of PS4 variants modified to become more thermostable by protein engineering.

Preferably, the PS4 variant polypeptide is pH stable; more preferably, it has a higher pH stability than its cognate parent polypeptide. As used herein the term "pH stable" relates to the ability of the enzyme to retain activity over a wide range of pHs. Preferably, the PS4 variant polypeptide is capable of degrading starch at a pH of from about 5 to about 10.5. In one embodiment, the degree of pH stability may be assayed by measuring the half life of the enzyme in specific pH conditions. In another embodiment, the degree of pH stability may be assayed by measuring the activity or specific activity of the enzyme in specific pH conditions. The specific pH conditions may be any pH from pH5 to pH10.5.

Thus, the PS4 variant polypeptide may have a longer half life, or a higher activity (depending on the assay) when compared to the parent polypeptide under identical conditions. The PS4 variant polypeptides may have 10%, 20%, 30%, 40%, 50%, 60%, 70%, 80%, 90%, 100%, 200% or longer half life when compared to their parent polypeptides under identical pH conditions. Alternatively, or in addition, they may have such higher activity when compared to the parent polypeptide under identical pH conditions.

Exo-Specificity

It is known that some non-maltogenic exoamylases can have some degree of endoamylase activity. In some cases, this type of activity may need to be reduced or eliminated since endoamylase activity can possibly negatively effect the quality of the final bread product by producing a sticky or gummy crumb due to the accumulation of branched dextrins.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exoamylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more. In highly preferred embodiments, the exo-specificity index is 150 or more, 200 or more, 300 or more, 400 or more, 500 or more or 600 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay (described in the Examples) are referred to in this document as "Phadebas units".

In a highly preferred embodiment, therefore, the exo-specificity index is expressed in terms of Betamyl Units/Phadebas Units, also referred to as "B/Phad".

Exo-specificity may also be assayed according to the methods described in the prior art, for example, in our International Patent Publication Number WO99/50399. This measures exo-specificity by way of a ratio between the endoamylase activity to the exoamylase activity. Thus, in a preferred aspect, the PS4 variants described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

The PS4 variants described here will preferably have exospecificity, for example measured by exo-specificity indices, as described above, consistent with their being exoamylases. Moreoever, they preferably have higher or increased exospecificity when compared to the parent enzymes or polypeptides from which they are derived. Thus, for example, the PS4 variant polypeptides may have 10%, 20%, 30%, 40%, 50%, 60%, 70%, 80%, 90%, 100%, 200% or higher exo-specificity index when compared to their parent polypeptides, preferably under identical conditions. They may have 1.5× or higher, 2× or higher, 5× or higher, 10× or higher, 50× or higher, 100× or higher, when compared to their parent polypeptides, preferably under identical conditions.

Improved Handling Properties

The PS4 variants described here preferably comprise one or more improved handling properties compared to a parent polypeptide or a wild type polypeptide. The improved handling properties may in preferred embodiments comprise improved baking properties.

Thus, the PS4 variants are such that a food product treated with the PS4 variant polypeptide an improved handling or preferably baking property compared to a food product which has been treated with a parent polypeptide or a wild type polypeptide. The handling or baking property may be selected from the group consisting of: firmness, resilience, cohesiveness, crumbliness and foldability.

These handling properties may be tested by any means known in the art. For example, firmness, resilience and cohesiveness may be determined by analysing bread slices by Texture Profile Analysis using for example a Texture Analyser, as described in the Examples.

Firmness

The PS4 variants described here are preferably such that a food product treated with the PS4 variant polypeptide lower firmness compared to a food product which has been treated with a parent polypeptide or a wild type polypeptide.

The firmness is in preferred embodiments inversely correlated with the softness of the food product; thus, a higher softness may reflect a lower firmness, and vice versa.

Firmness is preferably measured by the "Firmness Evaluation Protocol" set out in Example 13.

Thus, the PS4 variants described here are preferably such that a food product treated with the PS4 variant polypeptide has a 10%, 20%, 30%, 40%, 50%, 60%, 70%, 80%, 90%, 100%, 200% or more lower firmness compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more lower firmness compared to a food product which has been treated with a parent polypeptide or a wild type polypeptide.

Resilience

The PS4 variants described here are preferably such that a food product treated with the PS4 variant polypeptide higher resilience compared to a food product which has been treated with a parent polypeptide or a wild type polypeptide.

Resilience is preferably measured by the "Resilience Evaluation Protocol" set out in Example 14.

Thus, the PS4 variants described here are preferably such that a food product treated with the PS4 variant polypeptide has a 10%, 20%, 30%, 40%, 50%, 60%, 70%, 80%, 90%, 100%, 200% or more higher resilience compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more higher resilience compared to a food product which has been treated with a parent polypeptide or a wild type polypeptide.

Cohesiveness

The PS4 variants described here are preferably such that a food product treated with the PS4 variant polypeptide higher cohesiveness compared to a food product which has been treated with a parent polypeptide or a wild type polypeptide.

Cohesiveness is preferably measured by the "Cohesiveness Evaluation Protocol" set out in Example 15.

Thus, the PS4 variants described here are preferably such that a food product treated with the PS4 variant polypeptide has a 10%, 20%, 30%, 40%, 50%, 60%, 70%, 80%, 90%, 100%, 200% or more higher cohesiveness compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more higher cohesiveness compared to a food product which has been treated with a parent polypeptide or a wild type polypeptide.

Crumbliness

The PS4 variants described here are preferably such that a food product treated with the PS4 variant polypeptide lower crumbliness compared to a food product which has been treated with a parent polypeptide or a wild type polypeptide.

Crumbliness is preferably measured by the "Crumbliness Evaluation Protocol" set out in Example 16.

Thus, the PS4 variants described here are preferably such that a food product treated with the PS4 variant polypeptide has a 10%, 20%, 30%, 40%, 50%, 60%, 70%, 80%, 90%, 100%, 200% or more lower crumbliness compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more lower crumbliness compared to a food product which has been treated with a parent polypeptide or a wild type polypeptide.

Foldability

The PS4 variants described here are preferably such that a food product treated with the PS4 variant polypeptide higher foldability compared to a food product which has been treated with a parent polypeptide or a wild type polypeptide.

Foldability is preferably measured by the "Foldability Evaluation Protocol" set out in Example 17.

Thus, the PS4 variants described here are preferably such that a food product treated with the PS4 variant polypeptide has a 10%, 20%, 30%, 40%, 50%, 60%, 70%, 80%, 90%, 100%, 200% or more higher foldability compared to a food product which has been treated with a parent polypeptide or a wild type polypeptide. A food product treated with the PS4 variant polypeptide may have a 1.1×, 1.5×, 2×, 3×, 4×, 5×, 6×, 7×, 8×, 9×, 10× or more higher foldability compared to a food product which has been treated with a parent polypeptide or a wild type polypeptide.

We specifically describe the use of the PS4 variant polypeptides described here in combination with a xylanase for improviing fodability.

Uses of PS4 Variant Polypeptides and Nucleic Acids

ThePS4 variant polypeptides, nucleic acids, host cells, expression vectors, etc, may be used in any application for which an amylase may be used. In particular, they may be used to substitute for any non-maltogenic exoamylase. They may be used to supplement amylase or non-maltogenic exoamylase activity, whether alone or in combination with other known amylases or non-maltogenic exoamylases.

The PS4 variant sequences described here may be used in various applications in the food industry—such as in bakery and drink products, they may also be used in other applications such as a pharmaceutical composition, or even in the chemical industry. In particular, the PS4 variant polypeptides and nucleic acids are useful for various industrial applications including baking (as disclosed in WO 99/50399) and flour standardisation (volume enhancement or improvement). They may be used to produce maltotetraose from starch and other substrates.

We therefore describe a method for preparing a food product, the method comprising: (a) obtaining a non-maltogenic exoamylase; (b) introducing a mutation at any one or more of the positions of the non-maltogenic exoamylase as set out in this document; (c) admixing the resulting polypeptide with a food ingredient.

The PS4 variant polypeptides may be used to enhance the volume of bakery products such as bread. While not wishing to be bound by any particular theory, we believe that this results from the reduction in viscosity of the dough during heating (such as baking) as a result of the exoamylase shortening amylose molecules. This enables the carbon dioxide generated by fermentation to increase the size of the bread with less hindrance.

Thus, food products comprising or treated with PS4 variant polypeptides are expanded in volume when compared to products which have not been so treated, or treated with parent polypeptides. In other words, the food products have a larger volume of air per volume of food product. Alternatively, or in addition, the food products treated with PS4 variant polypeptides have a lower density, or weight (or mass) per volume ratio. In particularly preferred embodiments, the PS4 variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of PS4 variant polypeptides enhances the volume by 10%, 20%, 30% 40%, 50% or more.

The use of PS4 variant polypeptides to increase the volume of foods is described in detail in the Examples.

Food Uses

The PS4 variant polypeptides and nucleic acids described here may be used as—or in the preparation of—a food. In particular, they may be added to a food, i.e., as a food additive. The term "food" is intended to include both prepared food, as well as an ingredient for a food, such as a flour. In a preferred aspect, the food is for human consumption. The food may be in the from of a solution or as a solid—depending on the use and/or the mode of application and/or the mode of administration.

The PS4 variant polypeptides and nucleic acids may be used as a food ingredient. As used herein the term "food ingredient" includes a formulation, which is or can be added to functional foods or foodstuffs and includes formulations which can be used at low levels in a wide variety of products that require, for example, acidifying or emulsifying. The food ingredient may be in the from of a solution or as a solid—depending on the use and/or the mode of application and/or the mode of administration.

The PS4 variant polypeptides and nucleic acids disclosed here may be—or may be added to—food supplements. The PS4 variant polypeptides and nucleic acids disclosed here may be—or may be added to—functional foods. As used herein, the term "functional food" means food which is capable of providing not only a nutritional effect and/or a taste satisfaction, but is also capable of delivering a further beneficial effect to consumer. Although there is no legal definition of a functional food, most of the parties with an interest in this area agree that they are foods marketed as having specific health effects.

The PS4 variant polypeptides may also be used in the manufacture of a food product or a foodstuff. Typical foodstuffs include dairy products, meat products, poultry products, fish products and dough products. The dough product may be any processed dough product, including fried, deep fried, roasted, baked, steamed and boiled doughs, such as steamed bread and rice cakes. In highly preferred embodiments, the food product is a bakery product.

Preferably, the foodstuff is a bakery product. Typical bakery (baked) products include bread—such as loaves, rolls, buns, pizza bases etc. pastry, pretzels, tortillas, cakes, cookies, biscuits, krackers etc.

The food products preferably benefit from one or more of the improved handling or baking properties of the PS4 variant polypeptides described here. The improved handling or baking property may be selected from the group consisting of:

improved firmness, improved resilience, improved cohesiveness, improved crumbliness and improved foldability.

We therefore describe a method of modifying a food additive comprising a non-maltogenic exoamylase, the method comprising introducing a mutation at any one or more of the positions of the non-maltogenic exoamylase as set out in this document. The same method can be used to modify a food ingredient, or a food supplement, a food product, or a foodstuff.

Retrogradation/Staling

We describe the use of PS4 variant proteins that are capable of retarding the staling of starch media, such as starch gels. The PS4 variant polypeptides are especially capable of retarding the detrimental retrogradation of starch.

Most starch granules are composed of a mixture of two polymers: an essentially linear amylose and a highly branched amylopectin. Amylopectin is a very large, branched molecule consisting of chains of α-D-glucopyranosyl units joined by (1-4) linkages, wherein said chains are attached by α-D-(1-6) linkages to form branches. Amylopectin is present in all natural starches, constituting about 75% of most common starches. Amylose is essentially a linear chain of (1-4) linked α-D-glucopyranosyl units having few α-D-(1-6) branches. Most starches contain about 25% amylose.

Starch granules heated in the presence of water undergo an order-disorder phase transition called gelatinization, where liquid is taken up by the swelling granules. Gelatinization temperatures vary for different starches. Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bread crumb. This reinforcement is one of the main causes of bread staling.

It is known that the quality of baked products gradually deteriorates during storage As a consequence of starch recystallisation (also called retrogradation), the water-holding capacity of the crumb is changed with important implications on the organoleptic and dietary properties. The crumb loses softness and elasticity and becomes firm and crumbly. The increase in crumb firmness is often used as a measure of the staling process of bread.

The rate of detrimental retrogradation of amylopectin depends on the length of the side chains of amylopectin. Thus, enzymatic hydrolysis of the amylopectin side chains, for example, by PS4 variant polypeptides having non-maltogenic exoamylase activity, can markedly reduce their crystallisation tendencies.

Accordingly, the use of PS4 variant polypeptides as described here when added to the starch at any stage of its processing into a food product, e.g., before during or after baking into bread can retard or impede or slow down the retrogradation. Such use is described in further detail below.

We therefore describe a method of improving the ability of a non-maltogenic exoamylase to prevent staling, preferably detrimental retrogradation, of a dough product, the method comprising introducing a mutation at any one or more of the positions of the non-maltogenic exoamylase as set out in this document.

Assays for Measurement of Retrogradation (Inc. Staling)

For evaluation of the antistaling effect of the PS4 variant polypeptides having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a PS4 variant polypeptide having non-maltogenic exoamylase activity is based on DSC (differential scanning calorimetry). Here, the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10-20 mg of crumb are weighed and transferred into Mettler-Toledo aluminium pans which then are hermetically sealed.

The model system doughs used in the described examples contain standard wheat flour and optimal amounts of water or buffer with or without the non-maltogenic PS4 variant exoamylase. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

In preferred embodiments, the PS4 variants described here have a reduced melting enthalpy, compared to the control. In highly preferred embodiments, the PS4 variants have a 10% or more reduced melting enthalpy. Preferably, they have a 20% or more, 30%, 40%, 50%, 60%, 70%, 80%, 90% or more reduced melting enthalpy when compared to the control.

Preparation of Starch Products

We provide the use of PS4 variant polypeptides in the preparation of food products, in particular, starch products. The method comprises forming the starch product by adding a non-maltogenic exoamylase enzyme such as a PS4 variant polypeptide, to a starch medium. If the starch medium is a dough, then the dough is prepared by mixing together flour, water, the non-maltogenic exoamylase which is a PS4 variant polypeptide and optionally other possible ingredients and additives.

The term "starch" should be taken to mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour. The term "flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example from rice, maize, barley, and durra are also contemplated. Preferably, the starch product is a bakery product. More preferably, the starch product is a bread product. Even more preferably, the starch product is a baked farinaceous bread product. The term "baked farinaceous bread product" refers to any baked product based on a dough obtainable by mixing flour, water, and a leavening agent under dough forming conditions. Further components can of course be added to the dough mixture.

Thus, if the starch product is a baked farinaceous bread product, then the process comprises mixing—in any suitable order—flour, water, and a leavening agent under dough forming conditions and further adding a PS4 variant polypeptide, optionally in the form of a premix. The leavening agent may be a chemical leavening agent such as sodium bicarbonate or any strain of *Saccharomyces cerevisiae* (Baker's Yeast).

The PS4 variant non-maltogenic exoamylase can be added together with any dough ingredient including the water or dough ingredient mixture or with any additive or additive mixture. The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200→120° C.) is prevailing in the outer dough layers where the characteristic crust of the baked product is developed. However, owing to heat consumption due to steam generation, the temperature in the crumb is only close to 100° C. at the end of the baking process.

We therefore describe a process for making a bread product comprising: (a) providing a starch medium; (b) adding to the starch medium a PS4 variant polypeptide as described in this document; and (c) applying heat to the starch medium during or after step (b) to produce a bread product. We also describe a process for making a bread product comprising adding to a starch medium a PS4 variant polypeptide as described.

The non-maltogenic exoamylase PS4 variant polypeptide can be added as a liquid preparation or as a dry pulverulent composition either comprising the enzyme as the sole active component or in admixture with one or more additional dough ingredient or dough additive.

Improving Composition

We describe improver compositions, which include bread improving compositions and dough improving compositions. These comprise a PS4 variant polypeptide, optionally together with a further ingredient, or a further enzyme, or both.

We also provide for the use of such a bread and dough improving compositions in baking. In a further aspect, we provide a baked product or dough obtained from the bread improving composition or dough improving composition. In another aspect, we describe a baked product or dough obtained from the use of a bread improving composition or a dough improving composition.

Dough Preparation

A dough may be prepared by admixing flour, water, a dough improving composition comprising PS4 variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the PS4 variant polypeptide non-maltogenic exoamylase that is added is normally in an amount which results in the presence in the finished dough of 50 to 100,000 units per kg of flour, preferably 100 to 50,000 units per kg of flour. Preferably, the amount is in the range of 200 to 20,000 units per kg of flour. Alternatively, the PS4 variant polypeptide non-maltogenic exoamylase is added in an amount which results in the presence in the finished dough of 0.02-50 ppm of enzyme based on flour (0.02-50 mg enzyme per kg of flour), preferably 0.2-10 ppm.

In the present context, 1 unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

We also describe a pre-mix comprising flour together with the combination as described herein. The pre-mix may contain other dough-improving and/or bread-improving additives, e.g. any of the additives, including enzymes, mentioned herein.

Further Dough Additives or Ingredients

In order to improve further the properties of the baked product and impart distinctive qualities to the baked product further dough ingredients and/or dough additives may be incorporated into the dough. Typically, such further added components may include dough ingredients such as salt, grains, fats and oils, sugar or sweeteber, dietary fibres, protein sources such as milk powder, gluten soy or eggs and dough additives such as emulsifiers, other enzymes, hydrocolloids, flavouring agents, oxidising agents, minerals and vitamins The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

Suitable emulsifiers include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

Further Enzyme

One or more further enzymes may be used in combination with the PS4 variant polypeptides. Such combinations may for example added to the food, dough preparation, foodstuff or starch composition.

The further enzymes may be selected from, for example, any combination of the following: (a) Novamyl, or a variant, homologue, or mutants thereof which have maltogenic alpha-amylase activity; (b) a xylanase such as GRINDAMYL™ POWERBake 900 (Danisco A/S); (c) a bacterial α-amylase such as Max-Life U4 (Danisco A/S); and (d) a lipase such as GRINDAMYL™ POWERBake 4050 (Danisco A/S).

In one embodiment a PS4 variant polypeptide according to the invention is used in combination with at least one enzyme selected from the list consisting of oxidoreductases, hydrolases, lipases, esterases, glycosidases, amylases, pullulanases, xylanases, cellulases, hemicellulases, starch degrading enzymes, proteases and lipoxygenases. In a preferred embodiment, the composition comprises at least one PS4 variant and a maltogenic amylase from Bacillus, as disclosed in WO91/04669. A preferred embodiment comprises a PS4 variant and flour.

Further enzymes that may be added to the dough include oxidoreductases, hydrolases, such as lipases and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb firmness and bread volume. Lipases are useful as dough strengtheners and crumb softeners and α-amylases and other amylolytic enzymes may be incorporated into the dough to control bread volume and further reduce crumb firmness.

Further enzymes that may be used may be selected from the group consisting of a cellulase, a hemicellulase, a starch degrading enzyme, a protease, a lipoxygenase.

Examples of useful oxidoreductases include oxidises such as maltose oxidising enzyme, a glucose oxidase (EC 1.1.3.4), carbohydrate oxidase, glycerol oxidase, pyranose oxidase, galactose oxidase (EC 1.1.3.10) and hexose oxidase (EC 1.1.3.5). These enzymes can be used for dough strengthening and control of volume of the baked products.

Among starch degrading enzymes, amylases are particularly useful as dough improving additives. α-amylase breaks downs starch into dextrins which are further broken down by β-amylase to maltose. Examples of suitable amylases include maltogenic alpha-amylase also called glucan 1,4-α-maltohydrolase (EC 3.2.1.133) from Bacillus stearothermophilus (such as Novamyl™ (Novozymes)), α-amylase (EC 3.2.1.1) from Bacillus amyloliqufaciens (such as Max Life U4 (Danisco A/S)), B. flavothermus amylase (US 20050048611A1), Fungal amylase variants with insertions of alpha-amylase (EC 3.2.1.133) from Bacillus stearothermophilus (WO2005019443), hybrids of amylase as described in US20060147581A1, and variants, homologues and derivatives thereof which have maltogenic alpha-amylase activity. In a preferred embodiment, a PS4 variant polypeptide may be combined with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration. Other useful starch degrading enzymes which may be added to a dough composition include glucoamylases and pullulanases.

Preferably, the further enzyme is at least a xylanase and/or at least an amylase. The term "xylanase" as used herein refers to xylanases (EC 3.2.1.32) which hydrolyse xylosidic linkages. A lipase may also be added. Examples of suitable xylanases include bakery xylanases (EC 3.2.1.8) from e.g. Bacillus sp., Aspergillus sp., Thermomyces sp. or Trichoderma sp. (such as GRINDAMYL™ POWERBake 900 (Danisco A/S)) and xylanases pertaining to Family 10 or 11 e.g. from Thermomyces lanoginosus (previously called Humicola insolens), Aspergillus aculeatus (WO 94/21785), Bacillus halodurans (WO 2005/059084), Bacillus sp (EP 0 720 649 B1), B. agadeherens (U.S. Pat. No. 5,770,424), and variants, homologues and derivatives thereof.

The term "amylase" as used herein refers to amylases such as α-amylases (EC 3.2.1.1), β-amylases (EC 3.2.1.2) and γ-amylases (EC 3.2.1.3).

The further enzyme can be added together with any dough ingredient including the flour, water or optional other ingredients or additives, or the dough improving composition. The further enzyme can be added before the flour, water, and optionally other ingredients and additives or the dough improving composition. The further enzyme can be added after the flour, water, and optionally other ingredients and additives or the dough improving composition. The further enzyme may conveniently be a liquid preparation. However, the composition may be conveniently in the form of a dry composition.

Some enzymes of the dough improving composition are capable of interacting with each other under the dough conditions to an extent where the effect on improvement of the rheological and/or machineability properties of a flour dough and/or the quality of the product made from dough by the enzymes is not only additive, but the effect is synergistic.

In relation to improvement of the product made from dough (finished product), it may be found that the combination results in a substantial synergistic effect in respect to crumb structore. Also, with respect to the specific volume of baked product a synergistic effect may be found.

The further enzyme may be a lipase (EC 3.1.1) capable of hydrolysing carboxylic ester bonds to release carboxylate. Examples of lipases include but are not limited to triacylglycerol lipase (EC 3.1.1.3), galactolipase (EC 3.1.1.26), phospholipase A1 (EC 3.1.1.32, phospholipase A2 (EC 3.1.1.4) and lipoprotein lipase A2 (EC 3.1.1.34). More specifically, suitable lipases include lipases from *Mucor miehei, F. venenatum, H. lanuginosa, Rhizomucor miehei candida antarctica, F. oxysporum*, glycolipase from *Fusarium heterosporum* (such as GRINDAMYL™ POWERBake 4050 (Danisco A/S)) and variants, homologues and derivatives thereof Other Uses The PS4 variants are suitable for the production of maltose and high maltose syrups. Such products are of considerable interest in the production of certain confectioneries because of the low hygroscoposity, low viscosity, good heat stability and mild, not too sweet taste of maltose. The industrial process of producing maltose syrups comprises liquefying starch, then saccharification with a maltose producing enzyme, and optionally with an enzyme cleaving the 1.6-branching points in amylopectin, for instance an .alpha.-1.6-amyloglucosidase.

The PS4 variants described here may be added to and thus become a component of a detergent composition. The detergent composition may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, we describe a detergent additive comprising the PS4 variant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase. In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

The PS4 variant may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The PS4 variants may especially be useful in a process for producing a papermaking pulp from starch-coated printed paper. The process may be performed as described in WO 95/14807, comprising the following steps: a) disintegrating the paper to produce a pulp, b) treating with a starch-degrading enzyme before, during or after step a), and c) separating ink particles from the pulp after steps a) and b). The PS4 variant may also be very useful in modifying starch where enzymatically modified starch is used in papermaking together with alkaline fillers such as calcium carbonate, kaolin and clays. With the PS4 variants described here it becomes possible to modify the starch in the presence of the filler thus allowing for a simpler integrated process. A PS4 variant may also be very useful in textile desizing. In the textile processing industry, amylases are traditionally used as auxiliaries in the desizing process to facilitate the removal of starch-containing size which has served as a protective coating on weft yarns during weaving. Complete removal of the size coating after weaving is import-ant to ensure optimum results in the subsequent processes, in which the fabric is scoured, bleached and dyed. Enzymatic starch break-down is preferred because it does not involve any harmful effect on the fiber material. The PS4 variant may be used alone or in combination with a cellulase when desizing cellulose-containing fabric or textile.

The PS4 variant may also be an amylase of choice for production of sweeteners from starch A "traditional" process for conversion of starch to fructose syrups normally consists of three consecutive enzymatic processes, viz., a liquefaction process followed by a saccharification process and an isomerization process. During the liquefaction process, starch is degraded to dextrins by an amylase at pH values between 5.5 and 6.2 and at temperatures of 95-160° C. for a period of approx. 2 hours. In order to ensure an optimal enzyme stability under these conditions, 1 mM of calcium is added (40 ppm free calcium ions). After the liquefaction process the dextrins are converted into dextrose by addition of a glucoamylase and a debranching enzyme, such as an isoamylase or a pullulanase. Before this step the pH is reduced to a value below 4.5, maintaining the high temperature (above 95° C.), and the liquefying amylase activity is denatured. The temperature is lowered to 60° C., and glucoamylase and debranching enzyme are added. The saccharification process proceeds for 24-72 hours.

Laundry Detergent Compositions and Use

The $\alpha$-amylase variants discussed herein can be formulated in detergent compositions for use in cleaning dishes or other cleaning compositions, for example. These can be gels, powders or liquids. The compositions can comprise the $\alpha$-amylase variant alone, other amylolytic enzymes, other cleaning enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

In the detergent applications, $\alpha$-amylase variants are usually used in a liquid composition containing propylene glycol. The $\alpha$-amylase variant can be solubilized in propylene glycol, for example, by circulating in a 25% volume/volume propylene glycol solution containing 10% calcium chloride.

The dishwashing detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Suitable activator materials include tetraacetylethylenediamine (TAED) and glycerol triacetate. Enzymatic bleach activation systems may also be present, such as perborate or percarbonate, glycerol triacetate and perhydrolase, as disclosed in WO 2005/056783, for example.

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester). The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescent agents, thickeners, and perfumes.

Finally, the α-amylase variants may be used in conventional dishwashing detergents, e.g., in any of the detergents described in the following patent publications, with the consideration that the α-amylase variants disclosed herein are used instead of, or in addition to, any α-amylase disclosed in the listed patents and published applications: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, and U.S. Pat. Nos. 5,112,518; 5,141,664; and 5,240,632.

According to the embodiment, one or more α-amylase variants may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products; (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in U.S. Pat. No. 5,879,920 (Genencor International, Inc.) or EP 238216, for example. Polyols have long been recognized as stabilizers of proteins as well as for improving the solubility of proteins. See, e.g., Kaushik et al., "Why is trehalose an exceptional protein stabilizer? An analysis of the thermal stability of proteins in the presence of the compatible osmolyte trehalose" *J. Biol. Chem.* 278: 26458-65 (2003) and references cited therein; and M. Conti et al., "Capillary isoelectric focusing: the problem of protein solubility," *J. Chromatography* 757: 237-245 (1997).

The detergent composition may be in any convenient form, e.g., as gels, powders, granules, pastes, or liquids. A liquid detergent may be aqueous, typically containing up to about 70% of water, and 0% to about 30% of organic solvent, it may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide, as described in WO 92/06154, for example.

The detergent composition may additionally comprise one or more other enzymes, such as lipase, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder. Enzymes may be used in any composition compatible with the stability of the enzyme. Enzymes can be protected against generally deleterious components by known forms of encapsulation, as by granulation or sequestration in hydro gels, for example. Enzymes and specifically α-amylases either with or without the starch binding domains are not limited to laundry and dishwashing applications, but may bind use in surface cleaners and ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate optionally combined with a peracid-forming bleach activator, such as TAED or nonanoyloxybenzenesulfonate (NOBS). Alternatively, the bleaching system may comprise peroxy acids of the amide, imide, or sulfone type, for example. The bleaching system can also be an enzymatic bleaching system where a perhydrolase activates peroxide, such as that described in WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative, such as an aromatic borate ester; and the composition may be formulated as described in WO 92/19709 and WO 92/19708, for example.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0.

The α-amylase variant may be incorporated in concentrations conventionally employed in detergents. It is at present contemplated that, in the detergent composition, the α-amylase variant may be added in an amount corresponding to 0.00001-1.0 mg (calculated as pure enzyme protein) of α-amylase variant per liter of wash liquor. Particular forms of detergent compositions comprising the α-amylase variants can be formulated to include:

(1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate, about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3.H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

(2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate, about 1% to about 4%; zeolite (e.g., NaAlSiO$_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

(3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate, about 3% to about 9%; zeolite (as NaAlSiO$_4$) about 23% to about 33%; sodium sulfate (e.g., $Na_2SO_4$) 0% to about 4%; sodium perborate (e.g., $NaBO_3.H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

(4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate, about 1% to about 5%; zeolite (e.g., NaAlSiO$_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

(5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

(6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as NaAlSiO$_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%;glycerol 0% to about 5%; enzymes (calculated as pure enzyme protein) 0.0001-0.1%; and minor ingredients (e.g., dispersants, suds suppressors, perfume, optical brighteners) 0-5%.

(7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; soluble silicate, about 1% to about 4%; zeolite (e.g., NaAlSiO$_4$) about 20% to about 40%; sodium sulfate (e.g., $Na_2SO_4$) about 2% to about 8%; sodium perborate (e.g., $NaBO_3.H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

(8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate, about 1% to about 4%; zeolite (e.g., NaAlSiO$_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%;

enzymes (calculated as pure enzyme protein) 0.0001-0.1%; and minor ingredients (e.g., suds suppressors, perfume) 0-5%.

(9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3.H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

(10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

(11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

(12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates, about 5% to about 15%; sodium sulfate (e.g., $Na_2SO_4$) 0% to about 5%; zeolite ($NaAlSiO_4$) about 15% to about 28%; sodium perborate (e.g., $NaBO_3.H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

(13) Detergent compositions as described in compositions 1)-12) supra, wherein all or part of the linear alkylbenzenesulfonate is replaced by ($C_{12}$-$C_{18}$) alkyl sulfate.

(14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate, 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

(15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate, 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

(16) Detergent formulations as described in 1)-15) supra, which contain a stabilized or encapsulated peracid, either as an additional component or as a substitute for already specified bleach systems.

(17) Detergent compositions as described supra in 1), 3), 7), 9), and 12), wherein perborate is replaced by percarbonate.

(18) Detergent compositions as described supra in 1), 3), 7), 9), 12), 14), and 15), which additionally contains a manganese catalyst.

(19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

In another embodiment, the 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the detergent composition can comprise 2,6-β-D-fructan hydrolase, one or more α-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include Alcalase®, Savinase®, Esperase®, and Kannase™ (Novozymes, formerly Novo Nordisk A/S); Maxatase®, Maxacal™, Maxapem™, Properase™, Purafect®, Purafect OxP™, FN2™, and FN3™ (Genencor International, Inc.).

Lipases: suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens, Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. *Biochemica Biophysica Acta,* 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase® Ultra (Novozymes, formerly Novo Nordisk A/S).

Polyesterases: Suitable polyesterases include, but are not limited to, those described in WO 01/34899 (Genencor International, Inc.) and WO 01/14629 (Genencor International, Inc.), and can be included in any combination with other enzymes discussed herein.

Amylases: The compositions can be combined with other α-amylases, such as a non-variant α-amylase. These can include commercially available amylases, such as but not limited to Duramyl®, Termamyl™, Fungamyl® and BAN™ (Novozymes, formerly Novo Nordisk A/S), Rapidase®, and Purastar® (Genencor International, Inc.).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP 531 372; WO 99/25846 (Genencor International, Inc.), WO 96/34108 (Genencor International, Inc.), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include Celluzyme® and Carezyme® (Novozymes, formerly Novo Nordisk A/S); Clazinase™ and Puradax® HA (Genencor International, Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive, i.e., a separate additive or a combined additive, can be formulated as a granulate, liquid, slurry, etc. Suitable granulate detergent additive formulations include non-dusting granulates.

Non-dusting granulates may be produced, e.g., as disclosed in U.S. Pat. Nos. 4,106,991 and 4,661,452 and optionally may be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591, for example. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition may be in any convenient form, e.g., a bar, tablet, gel, powder, granule, paste, or liquid. A liquid detergent may be aqueous, typically containing up to about 70% water, and 0% to about 30% organic solvent. Compact detergent gels containing 30% or less water are also contemplated. The detergent composition comprises one or more surfactants, which may be non-ionic, including semi-polar, anionic, cationic, or zwitterionic, or any combination thereof. The surfactants are typically present at a level of from 0.1% to 60% by weight.

When included therein the detergent typically will contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose (CMC), poly(vinylpyrrolidone) (PVP), poly(ethylene glycol) (PEG), poly (vinyl alcohol) (PVA), poly(vinylpyridine-N-oxide), poly(vinylimidazole), polycarboxylates, e.g., polyacrylates, maleic/acrylic acid copolymers), and lauryl methacrylate/acrylic acid copolymers.

The detergent may contain a bleaching system that may comprise a source of $H_2O_2$, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g., the amide-, imide-, or sulfone-type peroxyacids). The bleaching system can also be an enzymatic bleaching system.

The enzyme(s) of the detergent composition may be stabilized using conventional stabilizing agents, e.g., polyol (e.g., propylene glycol or glycerol), a sugar or sugar alcohol, lactic acid, boric acid, a boric acid derivative (e.g., an aromatic borate ester), or a phenyl boronic acid derivative (e.g., 4-formylphenyl boronic acid). The composition may be formulated as described in WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is contemplated that in the detergent compositions, the enzyme variants may be added in an amount corresponding to about 0.01 to about 100 mg of enzyme protein per liter of wash liquor, particularly about 0.05 to about 5.0 mg of enzyme protein per liter of wash liquor, or even more particularly in 0.1 to about 1.0 mg of enzyme protein per liter of wash liquor.

Starch Processing Compositions and Use

In another aspect, compositions with the disclosed α-amylase variants can be utilized for starch liquefaction and/or saccharification. Starch processing is useful for producing sweetener, producing alcohol for fuel or drinking (i.e., potable alcohol), producing a beverage, processing cane sugar, or producing desired organic compounds, e.g., citric acid, itaconic acid, lactic acid, gluconic acid, ketones, amino acids, antibiotics, enzymes, vitamins, and hormones. Conversion of starch to fructose syrups normally consists of three consecutive enzymatic processes: a liquefaction process, a saccharification process, and an isomerization process. During the liquefaction process, a variant α-amylase degrades starch to dextrins by at pH between about 5.5 and about 6.2 and at temperatures of about 95° C. to about 160° C. for a period of approximately 2 hours. About 1 mM of calcium (40 ppm free calcium ions) typically is added to optimize enzyme stability under these conditions. Other α-amylase variants may require different conditions.

After the liquefaction process, the dextrins can be converted into dextrose by addition of a glucoamylase (e.g., AMG™) and optionally a debranching enzyme, such as an isoamylase or a pullulanase (e.g., Promozyme®). Before this step, the pH is reduced to a value below about 4.5, maintaining the high temperature (above 95° C.), and the liquefying α-amylase variant activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0, e.g., pH 7.5, and the calcium is removed by ion exchange. The dextrose syrup is then converted into high fructose syrup using an immobilized glucose isomerase (such as Sweetzyme®), for example.

The α-amylase variant may provide at least one improved enzymatic property for conducting the process of liquefaction. For example, the variant α-amylase may have a higher activity, or it may have a reduced requirement for calcium. Addition of free calcium is required to ensure adequately high stability of the α-amylase; however, free calcium strongly inhibits the activity of the glucose isomerase. Accordingly, the calcium should be removed prior to the isomerization step, by means of an expensive unit operation, to an extent that reduces the level of free calcium to below 3-5 ppm. Cost savings can be obtained if such an operation could be avoided, and the liquefaction process could be performed without addition of free calcium ions. Thus, α-amylase variants that do not require calcium ions or that have a reduced requirement for calcium are particularly advantageous. For example, a less calcium-dependent α-amylase variant, which is stable and highly active at low concentrations of free calcium (<40 ppm) can be utilized in the composition and procedures. Such an α-amylase variant should have a pH optimum in the range of about 4.5 to about 6.5, e.g., about pH 4.5 to about pH 5.5. The α-amylase variants can be used alone to provide specific hydrolysis or can be combined with other amylases to provide a "cocktail" with a broad spectrum of activity.

The starch to be processed may be a highly refined starch quality, for instance, at least 90%, at least 95%, at least 97%, or at least 99.5% pure. Alternatively, the starch can be a more crude starch containing material comprising milled whole grain, including non-starch fractions such as germ residues and fibers. The raw material, such as whole grain, is milled to open up the structure and allow further processing. Two milling processes are suitable: wet and dry milling. Also, corn grits, and milled corn grits may be applied. Dry milled grain will comprise significant amounts of non-starch carbohydrate compounds, in addition to starch. When such a heterogeneous material is processed by jet cooking, often only a partial gelatinization of the starch is achieved. Accordingly, α-amylase variants having a high activity towards ungelatinized starch are advantageously applied in a process comprising liquefaction and/or saccharification jet cooked dry milled starch.

A variant α-amylase having a superior hydrolysis activity during the liquefaction process advantageously increases the efficiency of the saccharification step (see WO 98/22613) and the need for glucoamylase during the saccharification step. The glucoamylase advantageously is present in an amount of no more than, or even less than, 0.5 glucoamylase activity unit (AGU)/g DS (i.e., glucoamylase activity units per gram of dry solids). The glucoamylase may be derived from a strain within *Aspergillus* sp., *Talaromyces* sp., *Pachykytospora* sp., or *Trametes* sp., with exemplary examples being *Aspergillus niger*, *Talaromyces emersonii*, *Trametes cingulata*, or *Pachykytospora papyracea*. In one embodiment, the process also comprises the use of a carbohydrate-binding domain of the type disclosed in WO 98/22613.

In yet another aspect, the process may comprise hydrolysis of a slurry of gelatinized or granular starch, in particular hydrolysis of granular starch into a soluble starch hydrolysate at a temperature below the initial gelatinization temperature of the granular starch. In addition to being contacted with an α-amylase variant, the starch may be contacted with one or more enzyme selected from the group consisting of a fungal α-amylase (EC 3.2.1.1), a β-amylase (EC 3.2.1.2), and a glucoamylase (EC 3.2.1.3). In an embodiment further another amylolytic enzyme or a debranching enzyme, such as an isoamylase (EC 3.2.1.68), or a pullulanases (EC 3.2.1.41) may be added to the α-amylase variant.

In one embodiment, the process is conducted at a temperature below the initial gelatinization temperature. Such processes are often conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, from about 3.5 to about 6.0, or from about 4.0 to about 5.0. One aspect contemplates a process comprising fermentation with a yeast, for example, to produce ethanol at a temperature around 32° C., such as from 30° C. to 35° C. In another aspect, the process comprises simultaneous saccharification and fermentation with a yeast to produce ethanol or with another suitable fermentation organism to produce a desired organic compound, for example, at a temperature from 30° C. to 35° C., e.g., at around 32° C. In the above fermentation processes, the ethanol content reaches at least about 7%, at least about 8%, at least about 9%, at least about 10%, at least about 11%, at least about 12%, at least about 13%, at least about 14%, at least about 15%, or at least about 16% ethanol.

The starch slurry to be used in any of the above aspects may have about 20% to about 55% dry solids granular starch, about 25% to about 40% dry solids granular starch, or about 30% to about 35% dry solids granular starch. The enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, the α-amylase variant is used in a process for liquefaction or saccharification of a gelatinized starch, including, but not limited to, gelatinization by jet cooking. The process may comprise fermentation to produce a fermentation product, e.g., ethanol. Such a process for producing ethanol from starch-containing material by fermentation comprises: (i) liquefying the starch-containing material with an α-amylase variant; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation (SSF) process. During the fermentation, the ethanol content reaches at least about 7%, at least about 8%, at least about 9%, at least about 10% such as at least about 11%, at least about 12%, at least about 13%, at least about 14%, at least about 15%, or at least about 16% ethanol.

The starch to be processed in the above aspects may be obtained from tubers, roots, stems, legumes, cereals or whole grain. More specifically, the granular starch may be obtained from corns, cobs, wheat, barley, rye, milo, sago, cassaya, tapioca, sorghum, rice, peas, bean, banana, or potatoes. Specially contemplated are both waxy and non-waxy types of corn and barley.

As used herein, the term "liquefaction" or "liquefy" means a process by which starch is converted to less viscous and shorter chain dextrins. Generally, this process involves gelatinization of starch simultaneously with or followed by the addition of an α-amylase variant. Additional liquefaction-inducing enzymes optionally may be added. As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from about 90-150° C., e.g., 100-110° C. Subsequent to application to a heat exchange or jet temperature, the slurry is held for a period of 3-10 minutes at that temperature. This step of holding the slurry at 90-150° C. is termed primary liquefaction.

As used herein, the term "secondary liquefaction" refers the liquefaction step subsequent to primary liquefaction (heating to 90-150° C.), when the slurry is allowed to cool to room temperature. This cooling step can be 30 minutes to 180 minutes, e.g. 90 minutes to 120 minutes. As used herein, the term "minutes of secondary liquefaction" refers to the time that has elapsed from the start of secondary liquefaction to the time that the Dextrose Equivalent (DE) is measured.

Another aspect contemplates the additional use of a β-amylase in the composition comprising the α-amylase variant. β-amylases (EC 3.2.1.2) are exo-acting maltogenic amylases, which catalyze the hydrolysis of 1,4-α-glucosidic linkages into amylose, amylopectin, and related glucose polymers, thereby releasing maltose. β-amylases have been isolated from various plants and microorganisms (Fogarty et al., PROGRESS IN INDUSTRIAL MICROBIOLOGY, Vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Genencor International, Inc.); and Novozym™ WBA (Novozymes A/S).

Another enzyme contemplated for use in the composition is a glucoamylase (EC 3.2.1.3). Glucoamylases are derived from a microorganism or a plant. For example, glucoamylases can be of fungal or bacterial origin. Exemplary bacterial glucoamylases are *Aspergillus* glucoamylases, in particular *A. niger* G1 or G2 glucoamylase (Boel et al. (1984), *EMBO J.* 3(5): 1097-1102), or variants thereof, such as disclosed in WO 92/00381 and WO 00/04136; *A. awamori* glucoamylase (WO 84/02921); *A. oryzae* glucoamylase (*Agric. Biol. Chem.* (1991), 55(4): 941-949), or variants or fragments thereof.

Other contemplated *Aspergillus* glucoamylase variants include variants to enhance the thermal stability: G137A and G139A (Chen et al. (1996), *Prot. Eng.* 9: 499-505); D257E and D293E/Q (Chen et al. (1995), *Prot. Eng.* 8: 575-582); N182 (Chen et al. (1994), *Biochem. J.* 301: 275-281); disulphide bonds, A246C (Fierobe et al. (1996), *Biochemistry,* 35: 8698-8704); and introduction of Pro residues in positions A435 and S436 (Li et al. (1997) *Protein Eng.* 10: 1199-1204). Other contemplated glucoamylases include Talaromyces glucoamylases, in particular derived from *T. emersonii* (WO 99/28448), *T. leycettanus* (U.S. Pat. No. RE 32,153), *T. duponti*, or *T. thermophilus* (U.S. Pat. No. 4,587,215). Contemplated bacterial glucoamylases include glucoamylases from the genus *Clostridium*, in particular *C. thermoamylolyticum* (EP 135138) and *C. thermohydrosulfuricum* (WO 86/01831). Suitable glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO:2 in WO 00/04136. Also suitable are commercial glucoamylases, such as AMG 200L; AMG 300 L; SAN™ SUPER and AMG™ E (Novozymes); OPTIDEX® 300 (Genencor International, Inc.); AMIGASE™ and AMIGASE™ PLUS (from DSM); G-ZYMEL® G900 (Enzyme Bio-Systems); and G-ZYME® G990 ZR (*A. niger* glucoamylase and low protease content). Glucoamylases may be added in an amount of 0.02-2.0 AGU/g DS or 0.1-1.0 AGU/g DS, e.g., 0.2 AGU/g DS.

Additional enzyme variants can be included in the composition. Two or more α-amylase variants can be used alone or in combination with other enzymes discussed herein. For example, a third enzyme may be another α-amylase, e.g., a yeast α-amylase, or another α-amylase variant. These can be *Bacillus* α-amylases or non-*Bacillus* α-amylases.

Another enzyme that can optionally be added is a debranching enzyme, such as an isoamylase (EC 3.2.1.68) or a pullulanases (EC 3.2.1.41). Isoamylase hydrolyses α-1,6-

D-glucosidic branch linkages in amylopectin and β-limit dextrins and can be distinguished from pullulanases by the inability of isoamylase to attack pullulan and by the limited action of isoamylase on α-limit dextrins. Debranching enzymes may be added in effective amounts well known to the person skilled in the art.

The exact composition of the products of the process depends on the combination of enzymes applied, as well as the type of granular starch processed. The soluble hydrolysate may be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5%, at least about 99.0% or at least about 99.5%. Alternatively, the soluble starch hydrolysate is glucose, or the starch hydrolysate has a DE (glucose percent of total solubilized dry solids) of at least 94.5%, at least 95.0%, at least 95.5%, at least 96.0%, at least 96.5%, at least 97.0%, at least 97.5%, at least 98.0%, at least 98.5%, at least 99.0% or at least 99.5%. In one embodiment, a process of manufacturing ice creams, cakes, candies, canned fruit uses a specialty syrup containing a mixture of glucose, maltose, DP3 and DPn.

Two milling processes are suitable: wet milling and dry milling. In dry milling, the whole kernel is milled and used. Wet milling gives a good separation of germ and meal (starch granules and protein) and is usually used when the starch hydrolysate is used in production of syrups. Both dry and wet milling are well known in the art of starch processing and also are contemplated for use with the compositions and methods disclosed. The process may be conducted in an ultrafiltration system where the retentate is held under recirculation in presence of enzymes, raw starch and water, where the permeate is the soluble starch hydrolysate. Another method is the process conducted in a continuous membrane reactor with ultrafiltration membranes, where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

In one regard, the soluble starch hydrolysate of the process is subjected to conversion into high fructose starch-based syrup (HFSS), such as high fructose corn syrup (HFCS). This conversion can be achieved using a glucose isomerase, particularly a glucose isomerase immobilized on a solid support. Contemplated isomerases included the commercial products Sweetzyme®, IT (Novozymes A/S); G-zyme® IMGI, and G-zyme® G993, Ketomax®, G-zyme® G993, G-zyme® G993 liquid, and GenSweet® IGI.

In another aspect, the soluble starch hydrolysate of produced yields production of fuel or potable ethanol. In the process of the third aspect the fermentation may be carried out simultaneously or separately/sequential to the hydrolysis of the granular starch slurry. When the fermentation is performed simultaneously with the hydrolysis, the temperature can be between 30° C. and 35° C., particularly between 31° C. and 34° C. The process may be conducted in an ultrafiltration system where the retentate is held under recirculation in presence of enzymes, raw starch, yeast, yeast nutrients and water and where the permeate is an ethanol containing liquid. Also contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta-lactone, or sodium erythorbate.

The amylolytic activity of the α-amylase variant may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

Ethanol Production

The PS4 variant polypeptide may in general be used to convert starch into sugars that can then be processed into ethanol or other value-added products such as high fructose corn sweetener. Thus, we disclose the use of PS4 variant polypeptides in the production of ethanol and specifically bioethanol, which in this document should be regarded as any ethanol produced by biomass fermentation.

The ethanol so produced may be used as a fuel or beverage or may be used in a fermentation process for producing organic compounds, such as citric acid, ascorbic acid, lysine, glutamic acid. These are described in further detail below.

Ethanol (or ethyl alcohol) is best known as being the basis of alcoholic beverages like spirits, beer and wine. In addition, ethanol has many uses in the production of industrial chemicals, pharmaceuticals and as a transportation fuel.

Ethanol can be produced from almost any raw material containing sugar or carbohydrates. As such, ethanol can be made from a wide variety of biological material. The 3 major types of biomass feedstocks used to produce ethanol include sugar crops, such as sugar cane; starch crops, including wheat and corn, and cellulosic materials, such as crop residues (straw, etc.), and forestry waste. Ethanol production from readily available sources of cellulose provides a stable, renewable fuel source.

The processing technology most frequently used is dry grain milling. In this process, the grain is first milled to a grain meal consistency. The meal is then mixed with water and amylase and passed through cookers where the starch in the grain is liquefied. Under the addition of gluco-amylase the liquefied starch is converted into fermentable sugars. Yeast is then added to the mash to ferment the sugars to ethanol. After fermentation, the mash goes through a distillation and dehydration process where the alcohol is removed from the solids and the water. In practice about two thirds of each tonne of grain is converted to fuel ethanol. The remaining by-products—thin stillage and wet distillers grain—are a high protein livestock feed which is particularly well suited for animals such as cattle or sheep.

Ethanol may also be made from cellulose containing sources, such as wood pulp. Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol, by treatment with a suitable enzyme such as cellulase.

Once ethanol leaves the processing plant, it can theoretically be used as an automotive fuel by itself or it can be mixed with gasoline at a ratio of 85 to 15 to form what is called "neat ethanol fuel". However, most commonly, ethanol is blended with gasoline at concentrations of 7 to 10% by volume. The ethanol may be used as an octane enhancer. Ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Brewery Applications

Ethanol (or ethyl alcohol) is best known as being the basis of alcoholic beverages like spirits, beer and wine. Thus, the PS4 variant polypeptides described here may be used for brewing, in particular, brewing beer. All beers are brewed using a process based on a simple formula.

The brewery process involves the use of malted grain, which depending on the region may traditionally be barley, wheat or sometimes rye. Malt is made by allowing a grain to germinate, after which it is then dried in a kiln and sometimes roasted. The germination process creates a number of enzymes, notably α-amylase and β-amylase, which will be used to convert the starch in the grain into sugar. Depending on the amount of roasting, the malt will take on dark colour and strongly influence the colour and flavour of the beer.

The malt is crushed to break apart the grain kernels, increase their surface area, and separate the smaller pieces from the husks. The resulting grist is mixed with heated water in a vat called a "mash tun" for a process known as "mashing". During this process, natural enzymes within the malt break down much of the starch into sugars which play a vital part in the fermentation process. Mashing usually takes 1 to 2 hours, and during this time various temperature rests (waiting periods) activate different enzymes depending upon the type of malt being used, its modification level, and the desires of the brewmaster. The activity of these enzymes convert the starches of the grains to dextrines and then to fermentable sugars such as maltose. The mash tun generally contains a slotted "false bottom" or other form of manifold which acts as a strainer allowing for the separation of the liquid from the grain.

A mash rest from 120° F. to 130° F. (49° C. to 55° C.) activates various proteinases, which break down proteins that might otherwise cause the beer to be hazy. But care is of the essence since the head on beer is also composed primarily of proteins, so too aggressive a protein rest can result in a beer that cannot hold a head. This rest is generally used only with undermodified (i.e. undermalted) malts which are decreasingly popular in Germany and the Czech Republic, or non-malted grains such as corn and rice, which are widely used in North American beers. A mash rest at 60° C. or 140° F. activates beta-glucanase, which breaks down gummy beta-glucans in the mash, making the sugars flow out more freely later in the process. In the modern mashing process commercial fungal based beta-glucanase may be added as a supplement. Finally, a mash rest temperature of 149 to 160° F. (65 to 71° C.) is used to convert the starches in the malt to sugar, which is then usable by the yeast later in the brewing process. Doing the latter rest at the lower end of the range produces more low-order sugars which are more fermentable by the yeast. This in turn creates a beer lower in body and higher in alcohol. A rest closer to the higher end of the range creates more higher-order sugars which are less fermentable by the yeast, so a fuller-bodied beer with less alcohol is the result.

After the mashing, the resulting liquid is strained from the grains in a process known as lautering. Prior to lautering, the mash temperature may be raised to 165° F. to 170° F. (about 75° C.) (known as a mashout) to deactivate enzymes. Additional water may be sprinkled on the grains to extract additional sugars (a process known as sparging).

At this point the liquid is known as wort. The wort is moved into a large tank known as a "copper" or kettle where it is boiled with hops and sometimes other ingredients such as herbs or sugars. The boiling process serves to terminate enzymatic processes, precipitate proteins, isomerize hop resins, concentrate and sterilize the wort. Hops add flavour, aroma and bitterness to the beer. At the end of the boil, the hopped wort settles to clarify it in a vessel called a "whirl-pool" and the clarified wort is then cooled.

The wort is then moved into a "fermentation vessel" where yeast is added or "pitched" with it. The yeast converts the sugars from the malt into alcohol, carbon dioxide and other components through a process called Glycolysis. After a week to three weeks, the fresh (or "green") beer is run off into conditioning tanks. After conditioning for a week to several months, the beer is often filtered to remove yeast and particulates. The "bright beer" is then ready for serving or packaging.

One or more of the PS4 variant polypeptides described here may therefore be added at any stage of the brewing process to supplement or the amylase activity generated naturally.

Feed Applications

In one embodiment, the PS4 variant polypeptide is capable of degrading resistant starch.

As used herein the term 'degrading' relates to the partial or complete hydrolysis or degradation of resistant starch to glucose and/or oligosaccharides—such as maltose and/or dextrins.

The PS4 variant polypeptide may degrade residual resistant starch that has not been completely degraded by an animals amylase. By way of example, the PS4 variant polypeptide may be used to assist an animal's amylase (eg. pancreatic amylase) in improving the degradation of resistant starch. Pancreatic α-amylase is excreted in the digestive system by animals. Pancreatic α-amylase degrades starch in the feed. However, a part of the starch, the resistant starch, is not degraded fully by the pancreatic α-amylase and is therefore not absorbed in the small intestine (see definition of resistant starch). The PS4 variant polypeptide in some embodiments is able to assist the pancreatic α-amylase in degrading starch in the digestive system and thereby increase the utilisation of starch by the animal.

The ability of an enzyme to degrade resistant starch may be analysed for example by a method developed and disclosed by Megazyme International Ireland Ltd. for the measurement of resistant starch, solubilised starch and total starch content of a sample (Resistant Starch Assay Procedure, AOAC Method 2002.02, AACC Method 32-40).

Accordingly, the PS4 variant polypeptides may be ingested by an animal for beneficial purposes, and may therefore be incorporated into animal feeds.

We therefore disclose the use of a PS4 variant polypeptide as a component for use in a feed comprising starch, or for use in a feed improvement composition, in which the PS4 variant polypeptide is capable of degrading resistant starch. We also disclose a feed comprising a starch and a PS4 variant polypeptide. We further disclose a method of degrading resistant starch in a feed comprising contacting said resistant starch with a PS4 variant polypeptide.

We further describe the use of a PS4 variant polypeptide in the preparation of a feed comprising a starch, to degrade resistant starch. Furthermore, we disclose the use of a PS4 variant polypeptide in the preparation of a feed to improve the calorific value of said feed. We disclose the use of an enzyme in the preparation of a feed to improve animal performance. In a further embodiment, we describe a process for preparing a feed comprising admixing a starch and a PS4 variant polypeptide enzyme.

By way of example, use of a component comprising PS4 variant polypeptides and which is capable of degrading resistant starch is advantageous because there is a marked increase in the degradation of starch and/or starch degradation products in an animal. Furthermore, such use is advantageous because there is a marked increase in the digestibility of starch and/or starch degradation products by an animal. Furthermore, such use is advantageous because it provides a means of enhancing the efficiency of deriving energy from a feed by an animal. Furthermore, such use is advantageous because it provides a means to enhance the bioavailability of resistant starch.

Animal Feeds

Animal feeds for which the PS4 variant polypeptides are suitable for use may be formulated to meet the specific needs of particular animal groups and to provide the necessary carbohydrate, fat, protein and other nutrients in a form that can be metabolised by the animal.

Preferably, the animal feed is a feed for swine or poultry.

As used herein the term 'swine' relates to non-ruminant omnivores such as pigs, hogs or boars. Typically, swine feed includes about 50 percent carbohydrate, about 20 percent protein and about 5% fat. An example of a high energy swine feed is based on corn which is often combined with feed supplements for example, protein, minerals, vitamins and amino acids such as lysine and tryptophan. Examples of swine feeds include animal protein products, marine products, milk products, grain products and plant protein products, all of which may further comprise natural flavourings, artificial flavourings, micro and macro minerals, animal fats, vegetable fats, vitamins, preservatives or medications such as antibiotics.

It is to be understood that where reference is made in the present specification, including the accompanying claims, to 'swine feed' such reference is meant to include "transition" or "starter" feeds (used to wean young swine) and "finishing" or "grower" feeds (used following the transition stage for growth of swine to an age and/or size suitable for market).

As used herein the term 'poultry' relates to fowl such as chickens, broilers, hens, roosters, capons, turkeys, ducks, game fowl, pullets or chicks. Poultry feeds may be referred to as "complete" feeds because they contain all the protein, energy, vitamins, minerals, and other nutrients necessary for proper growth, egg production, and health of the birds. However, poultry feeds may further comprise vitamins, minerals or medications such as coccidiostats (for example Monensin sodium, Lasalocid, Amprolium, Salinomycin, and Sulfaquinoxaline) and/or antibiotics (for example Penicillin, Bacitracin, Chlortetracycline, and Oxytetracycline).

Young chickens or broilers, turkeys and ducks kept for meat production are fed differently from pullets saved for egg production. Broilers, ducks and turkeys have larger bodies and gain weight more rapidly than do the egg-producing types of chickens. Therefore, these birds are fed diets with higher protein and energy levels.

It is to be understood that where reference is made in the present specification, including the accompanying claims, to 'poultry feed' such reference is meant to include "starter" feeds (post-hatching), "finisher", "grower" or "developer" feeds (from 6-8 weeks of age until slaughter size reached) and "layer" feeds (fed during egg production).

Animal feeds may be formulated to meet the animal's nutritional needs with respect to, for example, meat production, milk production, egg production, reproduction and response to stress. In addition, the animal feeds are formulated to improve manure quality.

In a preferred aspect the animal feed contains a raw material such as a legume, for example pea or soy or a cereal, for example wheat, corn (maize), rye or barley. Suitably, the raw material may be potato.

Feed Stuffs

The PS4 variant polypeptides may be used in feeds for animal consumption by the indirect or direct application of the PS4 variant polypeptides to the feed, whether alone or in combination with other ingredients, such as food ingredients.

Typical food ingredients may include any one or more of an additive such as an animal or vegetable fat, a natural or synthetic seasoning, antioxidant, viscosity modifier, essential oil, and/or flavour, dye and/or colorant, vitamin, mineral, natural and/or non-natural amino acid, nutrient, additional enzyme (including genetically manipulated enzymes), a binding agent such as guar gum or xanthum gum, buffer, emulsifier, lubricant, adjuvant, suspending agent, preservative, coating agent or solubilising agent and the like.

Examples of the application methods include, but are not limited to, coating the feed in a material comprising the PS4 variant polypeptide, direct application by mixing the PS4 variant polypeptide with the feed, spraying the PS4 variant polypeptide onto the feed surface or dipping the feed into a preparation of the PS4 variant polypeptide.

The PS4 variant polypeptide is preferably applied by mixing it with a feed or by spraying onto feed particles for animal consumption. Alternatively, the PS4 variant polypeptide may be included in the emulsion of a feed, or the interior of solid products by injection or tumbling.

The PS4 variant polypeptide may be applied to intersperse, coat and/or impregnate a feed. Mixtures with other ingredients may also be used and may be applied separately, simultaneously or sequentially. Chelating agents, binding agents, emulsifiers and other additives such as micro and macro minerals, amino acids, vitamins, animal fats, vegetable fats, preservatives, flavourings, colourings, may be similarly applied to the feed simultaneously (either in mixture or separately) or applied sequentially.

Amount of PS4 Variant Polypeptide

The optimum amount of the PS4 variant polypeptide to be used will depend on the feed to be treated and/or the method of contacting the feed with the PS4 variant polypeptide and/or the intended use for the same. The amount of PS4 variant polypeptide should be in a sufficient amount to be effective to substantially degrade resistant starch following ingestion and during digestion of the feed.

Advantageously, the PS4 variant polypeptide would remain effective following ingestion of a feed for animal consumption and during digestion of the feed until a more complete digestion of the feed is obtained, i.e. an increased calorific value of the feed is released.

Amylase Combinations

We disclose in particular combinations of PS4 variant polypeptides with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration.

A maltogenic alpha-amylase from *Bacillus* (EP 120 693) is commercially available under the trade name Novamyl (Novo Nordisk A/S, Denmark) and is widely used in the baking industry as an anti-staling agent due to its ability to reduce retrogradation of starch. Novamyl is described in detail in International Patent Publication WO 91/04669. The maltogenic alpha-amylase Novamyl shares several characteristics with cyclodextrin glucanotransferases (CGTases), including sequence homology (Henrissat B, Bairoch A; Biochem. J., 316, 695-696 (1996)) and formation of transglycosylation products (Christophersen, C., et al., 1997, Starch, vol. 50, No. 1, 39-45).

In highly preferred embodiments, we disclose combinations comprising PS4 variant polypeptides together with Novamyl or any of its variants. Such combinations are useful for food production such as baking. The Novamyl may in particular comprise Novamyl 1500 MG.

Other documents describing Novamyl and its uses include Christophersen, C., Pedersen, S., and Christensen, T., (1993) Method for production of maltose an a limit dextrin, the limit dextrin, and use of the limit dextrin. Denmark, and WO 95/10627. It is further described in U.S. Pat. No. 4,598,048 and U.S. Pat. No. 4,604,355. Each of these documents is hereby incorporated by reference, and any of the Novamyl polypeptides described therein may be used in combinations with any of the PS4 variant polypeptides described here.

Variants, homologues, and mutants of Novamyl may be used for the combinations, provided they retain alpha amylase activity. For example, any of the Novamyl variants disclosed in U.S. Pat. No. 6,162,628, the entire disclosure of which is hereby incorporated by reference, may be used in combination with the PS4 variant polypeptides described here. In particular, any of the polypeptides described in that document, specifically variants of SEQ ID NO:1 of U.S. Pat. No. 6,162,628 at any one or more positions corresponding to Q13, I16, D17, N26, N28, P29, A30, S32, Y33, G34, L35, K40, M45, P73, V74, D76 N77, D79, N86, R95, N99, I100, H103, Q119, N120, N131, S141, T142, A148, N152, A163, H169, N171, G172,I174, N176, N187, F188, A192, Q201, $N_2O_3$, H220, N234, G236, Q247, K249, D261, N266, L268, R272, N275, N276, V279, N280, V281, D285, N287, F297, Q299, $N_3O_5$, K316, N320, L321, N327, A341, N342, A348, Q365, N371, N375, M378, G397, A381, F389, N401, A403, K425, N436, S442, N454, N468, N474, S479, A483, A486, V487, S493, T494, S495, A496, S497, A498, Q500, N507, I510, N513, K520, Q526, A555, A564, S573, N575, Q581, S583, F586, K589, N595, G618, N621, Q624, A629, F636, K645, N664 and/or T681 may be used.

Amino Acid Sequences

The invention makes use of a PS4 variant nucleic acid, and the amino acid sequences of such PS4 variant nucleic acids are encompassed by the methods and compositions described here.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The PS4 variant enzyme described here may be used in conjunction with other enzymes. Thus we further disclose a combination of enzymes wherein the combination comprises a PS4 variant polypeptide enzyme described here and another enzyme, which itself may be another PS4 variant polypeptide enzyme.

PS4 Variant Nucleotide Sequence

As noted above, we disclose nucleotide sequences encoding the PS4 variant enzymes having the specific properties described.

The term "nucleotide sequence" or "nucleic acid sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" as used in this document includes genomic DNA, cDNA, synthetic DNA, and RNA. Preferably it means DNA, more preferably cDNA sequence coding for a PS4 variant polypeptide.

Typically, the PS4 variant nucleotide sequence is prepared using recombinant DNA techniques (i.e. recombinant DNA). However, in an alternative embodiment, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

Preparation of Nucleic Acid Sequences

A nucleotide sequence encoding either an enzyme which has the specific properties as defined herein (e.g., a PS4 variant polypeptide) or an enzyme which is suitable for modification, such as a parent enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Variants/Homologues/Derivatives

We further describe the use of variants, homologues and derivatives of any amino acid sequence of an enzyme or of any nucleotide sequence encoding such an enzyme, such as a PS4 variant polypeptide or a PS4 variant nucleic acid. Unless the context dictates otherwise, the term "PS4 variant nucleic acid" should be taken to include each of the nucleic acid entities described below, and the term "PS4 variant polypeptide" should likewise be taken to include each of the polypeptide or amino acid entities described below.

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of this document it is preferred to express homology in terms of sequence identity.

In the present context, an homologous sequence is taken to include a nucleotide sequence which may be at least 75, 80, 85 or 90% identical, preferably at least 95, 96, 97, 98 or 99% identical to a nucleotide sequence encoding a PS4 variant polypeptide enzyme (such as a PS4 variant nucleic acid). Typically, the homologues will comprise the same sequences that code for the active sites etc as the subject sequence. Although homology can also be considered in terms of similarity (i.e. amino acid residues having similar chemical properties/functions), in the context of this document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 Short Protocols in Molecular Biology, $4^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60).

However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput.Appl Biosci. 9: 745-756)(Taylor W. R. (1986) "The classification of amino acid conservation" J. Theor.Biol. 119; 205-218). Conservative substitutions may be made, for example according to the table below which describes a generally accepted Venn diagram grouping of amino acids.

| Set | | | | | | | | | | | Sub-set | | | | |
|---|---|---|---|---|---|---|---|---|---|---|---|---|---|---|---|
| Hydro-phobic | F | W | Y | H | K | M | I | L | V | A | G C | Aromatic<br>Aliphatic | F<br>I | W<br>L | Y<br>V | H |
| Polar | W | Y | H | K | R | E | D | C | S | T | N Q | Charged<br>Positively<br>charged<br>Negatively<br>charged | H<br>H<br><br>E | K<br>K<br><br>D | R<br>R | E D |
| Small | V | C | A | G | S | P | T | N | D | | | Tiny | A | G | S | |

We further disclose sequences comprising homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or 13-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell DC, *Trends Biotechnol.* (1995) 13(4), 132-134.

The nucleotide sequences described here, and suitable for use in the methods and compositions described here (such as PS4 variant nucleic acids) may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

We further describe the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the PS4 variant sequences may be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides (nucleotide sequences) such as the PS4 variant nucleic acids described in this document may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically, or by any means available to those of skill in the art. They may also be cloned by standard techniques. In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector. Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

We further describe sequences that are complementary to the nucleic acid sequences of PS4 variants or sequences that are capable of hybridising either to the PS4 variant sequences or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies. Therefore, we disclose the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein. More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

We further disclose nucleotide sequences that can hybridise to the nucleotide sequences of PS4 variants (including complementary sequences of those presented herein), as well as nucleotide sequences that are complementary to sequences that can hybridise to the nucleotide sequences of PS4 variants (including complementary sequences of those presented herein). We further describe polynucleotide sequences that are capable of hybridising to the nucleotide sequences presented herein under conditions of intermediate to maximal stringency.

In a preferred aspect, we disclose nucleotide sequences that can hybridise to the nucleotide sequence of a PS4 variant nucleic acid, or the complement thereof, under stringent conditions (e.g. 50° C. and 0.2×SSC). More preferably, the nucleotide sequences can hybridise to the nucleotide sequence of a PS4 variant, or the complement thereof, under high stringent conditions (e.g. 65° C. and 0.1×SSC).

Site-Directed Mutagenesis

Once an enzyme-encoding nucleotide sequence has been isolated, or a putative enzyme-encoding nucleotide sequence has been identified, it may be desirable to mutate the sequence in order to prepare an enzyme. Accordingly, a PS4 variant sequence may be prepared from a parent sequence. Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis").

In one aspect the sequence for use in the methods and compositions described here is a recombinant sequence—i.e. a sequence that has been prepared using recombinant DNA techniques. These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

In one aspect the sequence for use in the methods and compositions described here is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The nucleotide sequence for use in the methods and compositions described here may be incorporated into a recombinant replicable vector. The vector may be used to replicate and express the nucleotide sequence, in enzyme form, in and/or from a compatible host cell. Expression may be controlled using control sequences eg. regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression of PS4 Nucleic Acids and Polypeptides

The PS4 polynucleotides and nucleic acids may include DNA and RNA of both synthetic and natural origin which DNA or RNA may contain modified or unmodified deoxy- or dideoxy-nucleotides or ribonucleotides or analogs thereof. The PS4 nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The PS4 nucleic acid may even be codon optimised to further increase expression.

The term "synthetic", as used herein, is defined as that which is produced by in vitro chemical or enzymatic synthesis. It includes but is not limited to PS4 nucleic acids made with optimal codon usage for host organisms such as the methylotrophic yeasts *Pichia* and *Hansenula*.

Polynucleotides, for example variant PS4 polynucleotides described here, can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

The term "transformed cell" includes cells that have been transformed by use of recombinant DNA techniques. The transformation typically occurs by insertion of one or more nucleotide sequences into a cell that is to be transformed. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence (i.e. is a sequence that is natural to the cell that is to be transformed)—so that the cell receives one or more extra copies of a nucleotide sequence already present in it.

Thus in a further embodiment, we provide a method of making PS4 variant polypeptides and polynucleotides by introducing a polynucleotide into a replicable vector, introducing the vector into a compatible host cell, and growing the host cell under conditions which bring about replication of the vector. The vector may be recovered from the host cell.

Expression Constructs

The PS4 nucleic acid may be operatively linked to transcriptional and translational regulatory elements active in a host cell of interest. The PS4 nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the PS4 nucleic acid may encode a fusion protein comprising a membrane binding domain.

Expression Vector

The PS4 nucleic acid may be expressed at the desired levels in a host organism using an expression vector.

An expression vector comprising a PS4 nucleic acid can be any vector which is capable of expressing the gene encoding PS4 nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector may be one which, when introduced into a host cell, is integrated into the host cell genome and replicated together with the chromosome.

Components of the Expression Vector

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the PS4 variant polypeptide to a host cell organelle such as a peroxisome or to a particular host cell compartment. Such a targeting sequence includes but is not limited to the sequence SKL. In the present context, the term "expression signal" includes any of the above control sequences, repressor or activator sequences. For expression under the direction of control sequences, the nucleic acid sequence the PS4 variant polypeptide is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators. The control sequences may in particular comprise promoters.

Promoter

In the vector, the nucleic acid sequence encoding for the variant PS4 polypeptide is operably combined with a suitable promoter sequence. The promoter can be any DNA sequence having transcription activity in the host organism of choice and can be derived from genes that are homologous or heterologous to the host organism.

Bacterial Promoters

Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes, the promoter of the *Bacillus subtilis* apre gene and a promoter derived from a *Lactococcus* sp.-derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

Fungal Promoters

For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Yeast Promoters

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Host Organisms (I) Bacterial Host Organisms

Examples of suitable bacterial host organisms are gram positive bacterial species such as Bacillaceae including *Bacillus clausii, Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism.

(II) Yeast Host Organisms

A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to *Schizosaccharomyce* such as, for example, *S. Pombe* species.

Preferably a strain of the methylotrophic yeast species *Pichia pastoris* is used as the host organism. Preferably the host organism is a *Hansenula* species.

(III) Fungal Host Organisms

Suitable host organisms among filamentous fungi include species of *Aspergillus*, e.g. *Aspergillus niger, Aspergillus oryzae, Aspergillus tubigensis, Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Suitable fungal host organisms may also include *Trichoderma* spp (especially *Trichoderma reesei* formerly *Trichoderma longibrachiatum*; also known as *Hypocrea* jecorina).

Protein Expression and Purification

Host cells comprising polynucleotides may be used to express polypeptides, such as variant PS4 polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ (Promega) rabbit reticulocyte system.

EXAMPLES

Example 1

Cloning of PS4

*Pseudomonas sacharophila* is grown overnight on LB media and chromosomal DNA is isolated by standard methods (Sambrook J, 1989). A 2190 bp fragment containing the PS4 open reading frame (Zhou et al., 1989) is amplified from *P. sacharophila* chromosomal DNA by PCR using the primers P1 and P2 (see Table 3). The resulting fragment is used as a template in a nested PCR with primers P3 and P4, amplifying the openreading frame of PS4 without its signal sequence and introducing a NcoI site at the 5' end of the gene and a BamHI site at the 3' end. Together with the NcoI site a codon for a N-terminal Methionine is introduced, allowing for intracellular expression of PS4. The 1605 bp fragment is cloned into pCRBLUNT TOPO (Invitrogen) and the integrity of the construct analysed by sequencing. The *E. coli Bacillus* shuttle vector pDP66K (Penning a et al., 1996) is modified to allow for expression of the PS4 under control of the P32 promoter and the ctgase signal sequence. The resulting plasmid, pCSmta is transformed into *B. subtilis*.

A second expression construct is made in which the starch binding domain of PS4 is removed. In a PCR with primers P3 and P6 (Table 3) on pCSmta, a truncated version of the mta gene is generated. The full length mta gene in pCSmta is exchanged with the truncated version which resulted in the plasmid pCSmta-SBD.

Example 2

Site Directed Mutagenesis of PS4

Mutations are introduced into the mta gene by 2 methods. Either by a 2 step PCR based method, or by a Quick Exchange method (QE). For convenience the mta gene is split up in 3 parts; a PvuI-FspI fragment, a FspI-PstI fragment and a PstI-AspI fragment, further on referred to as fragment 1, 2 and 3 respectively.

In the 2 step PCR based method, mutations are introduced using Pfu DNA polymerase (Stratagene). A first PCR is carried out with a mutagenesis primer (Table 4) for the coding strand plus a primer downstream on the lower strand (either 2R or 3R Table 3). The reaction product is used as a primer in a second PCR together with a primer upstream on the coding strand. The product of the last reaction is cloned into pCR-BLUNT topo (Invitrogen) and after sequencing the fragment is exchanged with the corresponding fragment in pCSmta.

Using the Quick Exchange method (Stratagene), mutations are introduced using two complementary primers in a PCR on a plasmid containing the mta gene, or part of the mta gene.

For this purpose a convenient set of plasmids is constructed, comprising of 3 SDM plasmids and 3 pCSΔ plasmids. The SDM plasmids each bear 1 of the fragments of the mta gene as mentioned above, in which the desired mutation is introduced by QE. After verification by sequencing, the fragments are cloned into the corresponding recipient pCSΔ plasmid. The pCSΔ plasmids are inactive derivatives from pCSmta. Activity is restored by cloning the corresponding fragment from the SDM plasmid, enabling easy screening.

TABLE 3

Primers used in cloning the mta gene, and standard primers used in construction of site directed mutants with the 2 step PCR method.

| Primer | Primer sequence | SEQ ID NO: | Introduced site |
|---|---|---|---|
| P1 | 5'- ATG ACG AGG TCC TTG TTT TTC | 35 | |
| P2 | 5'- CGC TAG TCG TCC ATG TCG | 36 | |
| P3 | 5'- <u>GCC ATG GAT</u> CAG GCC GGC AAG AGC CCG | 37 | NcoI |
| P4 | 5'- <u>TGG ATC C</u>TC AGA ACG AGC CGC TGG T | 38 | BamHI |
| P6 | 5'- <u>GAA TTC</u> AGC CGC CGT CAT TCC CGC C | 39 | EcoRI |
| 2L | 5'-AGA TTT ACG GCA TGT TTC GC | 40 | |
| 2R | 5'-TAG CCG CTA TGG AAG CTG AT | 41 | |
| 3L | 5'-TGA CCT TCG TCG ACA ACC AC | 42 | |
| 3R | 5'-GAT AGC TGC TGG TGA CGG TC | 43 | |

TABLE 4

Primers used to introduce site directed mutations in mta

| Mutation | Oligo Sequence | SEQ ID NO: | Modification | Strand | Purpose |
|---|---|---|---|---|---|
| G134R | CTGCCGGCCGGCCAGcGCT-TCTGGCG | 44 | | + | SDM |
| G134R- | cgccagaagcgctggccg-gccggcag | 45 | | − | SDM |
| I157L | GACGGTGACCGCTTC-cTgGGCGGCGAGTCG | 46 | | + | SDM |
| I151L- | cgactcgccgcccag-gaagcggtcaccgtc | 47 | | − | SDM |
| G223A | GGCGAGCTGTGGAAAgc-cCCTTCTGAATATCCG | 48 | | + | SDM |
| G223A- | cggatattca-gaagggctttccacagctcgcc | 49 | | − | SDM |
| H307L | gaacGGCGGCCAGCACct-gTGGGCGCTGCAG | 50 | | + | SDM |
| H307L- | ctgcagcgcccacaggt-gctggccgccgttc | 51 | | − | SDM |
| S334P, D343E | GTACTGGccgCACATGTAC-GACTGGGGCTACGGCgaaTTCATC | 52 | | + | SDM |
| S334P, D343E- | gatgaattcgccgtagc-cccagtcgtacatgtgcggccagtac | 53 | | − | SDM |

TABLE 5

Features of the SDM and pCSΔ plasmids

| Plasmid | Features/construction |
|---|---|
| SDM1 | pBlueSK+ 480 bp SalI-StuI fragment mta |
| SDM2 | pBlueSK+ 572 bp SacII-PstI fragment mta |
| SDM3 | pBlueSK+ 471 bp SalI-StuI fragment mta |
| pCSΔ1 | FseI site filled in with Klenow ---> frameshift in mta |
| pCSΔ2 | FspI-PstI fragment of mta replaced with 'junk-DNA' |
| pCSΔ3 | PstI-AspI fragment of mta replaced with 'junk-DNA' |

Example 3

Multi SDM

The PS4 variants were generated using a QuikChange Multi Site Directed Mutagenesis Kit (Stratagene) according to the manufactures protocol with some modifications as described.
Step 1: Mutant Strand Synthesis Reaction (PCR)
Inoculate 3 ml. LB (22 g/l Lennox L Broth Base, Sigma)+ antibiotics (0.05 µg/ml kanamycin, Sigma) in a 10 ml Falcon tube
Incubate o/n 37° C., ca. 200 rpm.
Spin down the cells by centrifugation (5000 rpm/5 min)
Poor off the medium
Prepare ds-DNA template using QIAGEN Plasmid Mini Purification Protocol 1. The mutant strand synthesis reaction for thermal cycling was prepared as follow:
PCR Mix:

| | |
|---|---|
| 2.5 µl | 10X QuickChange ® Multi reaction buffer |
| 0.75 µl | QuickSolution |
| X µl | Primers (primer length 28-35 bp → 10 pmol / primer length 24-27 bp → 7 pmol / primer length 20-23 bp → 5 pmol) |
| 1 µl | dNTP mix |
| X µl | ds-DNA template (200 ng) |
| 1 µl | QuickChange ® Multi enzyme blend (2.5 U/µl) (Pfu Turbo ® DNA polymerase) |
| X µl | dH$_2$O (to a final volume of 25 µl) |

Mix all components by pipetting and briefly spin down the reaction mixtures.
2. Cycle the reactions using the following parameters:
35 cycles of denaturation (96° C./1 min)
primer annealing (62.8° C./1 min)
elongation (65° C./15 min)
then hold at 4° C.
Preheat the lid of the PCR machine to 105° C. and the plate to 95° C. before the PCR tubes are placed in the machine (eppendorf thermal cycler).

Step 2: Dpn I Digestion
1. Add 2 µl Dpn I restriction enzyme (10 U/µl) to each amplification reaction, mix by pipetting and spin down mixture.
2. Incubate at 37° C. for ~3 hr.

Step 3: Transformation of XL10-Gold® Ultracompetent Cells
1. Thaw XL10-Gold cells on ice. Aliquot 45 µl cells per mutagenesis reaction to prechilled Falcon tubes.
2. Turn on the waterbath (42° C.) and place a tube with NZY⁺ broth in the bath to preheat.
3. Add 2 l β-mercaptoethanol mix to each tube. Swirl and tap gently and incubate 10 min on ice, swirling every 2 min.
4. Add 1,5 µl Dpn I-treated DNA to each aliquot of cells, swirl to mix and incubate on ice for 30 min.
5. Heat-pulse the tubes in 42° C. waterbath for 30 s and place on ice for 2 min.
6. Add 0.5 ml preheated NZY⁺ broth to each tube and incubate at 37° C. for 1 hr with shaking at 225-250 rpm.
7. Plate 200 µl of each transformation reaction on LB plates (33.6 g/l Lennox L Agar, Sigma) containing 1% starch and 0.05 µg/ml kanamycin
8. Incubate the transformation plates at 37° C. overnight.

TABLE 6

Primer table for pPD77d14:

| Mutation | Oligo Sequence | SEQ ID NO: | Modification | Strand | Purpose |
|---|---|---|---|---|---|
| N33Y, D34N | GCGAAGCGCCCTACAACTG-GTACAAC | 54 | 5' phosphate | + | MSDM |
| K71R | CCGACGGCGGCAGGTCCGGCG | 55 | 5' phosphate | + | MSDM |
| G87S | CAAGAACAGCCGCTACG-GCAGCGAC | 56 | 5' phosphate | + | MSDM |
| G121D | CACATGAACCGCGACTAC-CCGGACAAG | 57 | 5' phosphate | + | MSDM |
| G134R | CTGCCGGCCGGCCAGcGCT-TCTGGCG | 44 | 5' phosphate | + | MSDM |
| A141P | CGCAACGACTGCGCCGAC-CCGGG | 58 | 5' phosphate | + | MSDM |
| I157L | GACGGTGACCGCTTC-cTgGGCGGCGAGTCG | 46 | 5' phosphate | + | MSDM |
| L178F, A179T | CGCGACGAGTTTACCAAC-CTGCG | 59 | 5' phosphate | + | MSDM |
| G223A | GGCGAGCTGTGGAAAgc-cCCTTCTGAATATCCG | 48 | 5' phosphate | + | MSDM |
| H307L | gaacGGCGGCCAGCACct-gTGGGCGCTGCAG | 50 | 5' phosphate | + | MSDM |
| S334P, D343E | GTACTGGccgCACATGTAC-GACTGGGGCTACGGCgaaTTCATC | 52 | 5' phosphate | + | MSDM |

TABLE 7

Primer table for pPD77d20:

| Mutation | Oligo Sequence | SEQ ID NO: | Modification | Strand | Purpose |
|---|---|---|---|---|---|
| N33Y, D34N | GCGAAGCGCCCTACAACTG-GTACAAC | 54 | 5' phosphate | + | MSDM |
| K71R | CCGACGGCGGCAGGTCCGGCG | 55 | 5' phosphate | + | MSDM |

TABLE 7-continued

Primer table for pPD77d20:

| Mutation | Oligo Sequence | SEQ ID NO: | Modification | Strand | Purpose |
|---|---|---|---|---|---|
| G121D | CACATGAACCGCGACTAC-CCGGACAAG | 57 | 5' phosphate | + | MSDM |
| G134R | CTGCCGGCCGGCCAGcGCT-TCTGGCG | 44 | 5' phosphate | + | MSDM |
| A141P | CGCAACGACTGCGCCGAC-CCGGG | 58 | 5' phosphate | + | MSDM |
| I157L | GACGGTGACCGCTTC-cTgGGCGGCGAGTCG | 46 | 5' phosphate | + | MSDM |
| L178F, A179T | CGCGACGAGTTTACCAAC-CTGCG | 59 | 5' phosphate | + | MSDM |
| G223A | GGCGAGCTGTGGAAAgc-cCCTTCTGAATATCCG | 48 | 5' phosphate | + | MSDM |
| H307L | gaacGGCGGCCAGCACct-gTGGGCGCTGCAG | 50 | 5' phosphate | + | MSDM |
| S334P, D343E | GTACTGGccgCACATGTAC-GACTGGGGCTACGGCgaaTTCATC | 52 | 5' phosphate | + | MSDM |

TABLE 8

Primer table for pPD77d34:

| Mutation | Oligo Sequence | SEQ ID NO: | Modification | Strand | Purpose |
|---|---|---|---|---|---|
| N33Y, D34N | GCGAAGCGCCCTACAACTG-GTACAAC | 54 | 5' phosphate | + | MSDM |
| G121D | CACATGAACCGCGACTAC-CCGGACAAG | 57 | 5' phosphate | + | MSDM |
| G134R | CTGCCGGCCGGCCAGcGCT-TCTGGCG | 44 | 5' phosphate | + | MSDM |
| A141P | CGCAACGACTGCGCCGAC-CCGGG | 58 | 5' phosphate | + | MSDM |
| I157L | GACGGTGACCGCTTC-cTgGGCGGCGAGTCG | 46 | 5' phosphate | + | MSDM |
| L178F, A179T | CGCGACGAGTTTACCAAC-CTGCG | 59 | 5' phosphate | + | MSDM |
| G223A | GGCGAGCTGTGGAAAgc-cCCTTCTGAATATCCG | 48 | 5' phosphate | + | MSDM |
| H307L | gaacGGCGGCCAGCACct-gTGGGCGCTGCAG | 50 | 5' phosphate | + | MSDM |

TABLE 8-continued

Primer table for pPD77d34:

| Mutation | Oligo Sequence | SEQ ID NO: | Modification | Strand | Purpose |
|---|---|---|---|---|---|
| S334P | GTACTGGccgCACATGTAC-GAC TGGGGCTACGGC | 60 | 5' phosphate | + | MSDM |

Vector System Based on pPD77

The vector system used for pPD77 is based on pCRblunt-TOPOII (invitrogen). The zeocin resistance cassette has been removed by pmlI, 393 bp fragment removed. The expression cassette from the pCC vector (P32-ssCGTase-PS4-tt) has then been inserted into the vector.

Ligation of PS4 Variant into pCCMini

The plasmid which contain the relevant mutations (created by MSDM) is cut with restriction enzyme Nco 1 and Hind III (Biolabs):

3 μg plasmid DNA, X μl 10× buffer 2, 10 units Nco 1, 20 units HindIII,

Incubation 2 h at 37° C.

Run digestion on a 1% agarose gel. Fragments sized 1293 bp (PS4 gene) is cut out of the gel and purified using Qiagen gel purification kit.

The vector pCCMini is then cut with restriction enzymes, Nco 1 and Hind III, and the digestion is then run on a 1% agarose gel. The fragment sized 3569 bp is cut out of the gel and purified using Qiagen gel purification kit.

Ligation: Use Rapid DNA ligation kit (Roche)

Use the double amount of insert compared to vector e.g. 2 μl insert (PS4 gene)

1 μl vector

5 μl T4 DNA ligation buffer 2×conc

1 μl dH$_2$O

1 μl T4 DNA ligase

Ligate 5 min/RT

Transform the ligation into One Shot TOPO competent cells according to manufactures protocol (Invitrogen). Use 5 μl ligation per transformation.

Plate 50 μl transformationsmix onto LB plates (33.6 g/l Lennox L Agar, Sigma) containing 1% starch and 0.05 μg/ml kanamycin. Vectors containing insert (PS4 variants) can be recognised by halo formation on the starch plates.

Example 3A

Production of PS4 Variant Polypeptide with Substitution at Position 307 pSac-pMD229

Sequence pSac-pMD229 (SEQ ID NO: 14) comprising mutations atN33Y, D34N, G121F, G134R, A141P, Y146G, I157L, S161A, L178F, A179T, G223E, S229P, H272Q, G303E, H307L, A309P, S334P relative to wild type non-maltogenic exoamylase is made from a wild type sequence using site directed mutagenesis (as described above in Example 2) or Multi Site Directed Mutagenesis (as described above in Example 3), with the primers in the table below:

Primers for pMD229

| Purpose | Description | Modification | Strand | 5' Oligo Sequence 3' | SEQ ID NO: |
|---|---|---|---|---|---|
| MSDM | N33Y, D34N | 5' phosphate | + | GCGAAGCGCCCTACAACTGGTACAAC | 54 |
| MSDM | G121F | 5' phosphate | + | CCAATCACATGAACCGCttcTACCCGGACAAGGAG | 61 |
| SDM | G134R | | + | CTGCCGGCCGGCCAGcGCTTCTGGCG | 44 |
| SDM | G134R- | | - | cgccagaagcgctggccggccggcag | 45 |
| MSDM | A141P | 5' phosphate | + | CGCAACGACTGCGCCGACCCGGG | 58 |
| MSDM | Y146G | 5' phosphate | + | GATCCGGGCAACggcCCCAACGACTGCG | 62 |
| SDM | I157L | | + | GACGGTGACCGCTTCcTgGGCGGCGAGTCG | 46 |
| SDM | I157L- | | - | cgactcgccgcccaggaagcggtcaccgtc | 47 |
| MSDM | S161A | 5' phosphate | + | GGGCGGCGAGcgGACCTGAACA | 63 |
| MSDM | L178F, A179T | 5' phosphate | + | CGCGACGAGTTTACCAACCTGCG | 59 |
| MSDM | G223E(gag) | 5' phosphate | + | GGCGAGCTGTGGAAAGDNCCTTCTGAATATCCGAG | 64 |

Primers for pMD229

| Purpose | Description | Modification | Strand | 5' Oligo Sequence 3' | SEQ ID NO: |
|---|---|---|---|---|---|
| MSDM | S229P | 5' phosphate | + | GCCTTCTGAATATCCGccgTGGGACTGGCGCAAC | 65 |
| MSDM | H272Q | 5' phosphate | + | CCGACTGGAAGcagGGCCTCAATGGC | 66 |
| MSDM | G303E | 5' phosphate | + | CCGGGCAGAACgaaGGCCAGCACCTGTG | 67 |
| SDM | H307L | | + | gaacGGCGGCCAGCACctgTGGGCGCTGCAG | 50 |
| SDM | H307L- | | - | ctgcagcgcccacaggtgctggccgccgttc | 51 |
| MSDM | A309P | 5' phosphate | + | GCACCTGTGGccgCTGCAGGACG | 68 |
| SDM | S334P, D343E | | + | GTACTGGccgCACATGTACGACTGGGGCTACGGCgaaTTCATC | 52 |
| SDM | S334P, D343E- | | - | gatgaattcgccgtagccccagtcgtacatgtgcggcagtac | 53 | psac-pMS382

Sequence pSac-pMS382 (SEQ ID NO: 22) comprising 307K is made from pSac-pSac-pMD229 using Multi Site Directed Mutagenesis (as described above in Example 3), with the primers in the table below:

Primers for pMD229 --> pMS382:

| Purpose | Description | Modification | Strand | 5' Oligo Sequence 3' | SEQ ID NO: |
|---|---|---|---|---|---|
| MSDM | G70K (synt) | 5' phosphate | + | CTGGACGGATGGAgatAAAAGCGGAGGCGGC | 59 |
| MSDM | Q272H (synt) | 5' phosphate | + | CGTCGCCGATTGGAAAcatGGCCTGAACGGAAATC | 70 |
| MSDM | E303G (synt) | 5' phosphate | + | CCGGGACAAAATggaGGACAACATCTTTGGC | 71 |
| MSDM | L307K (synt) | 5' phosphate | + | CAAAATGAAGGACAACATaaaTGGCCGCTTCAAGATGGCC | 72 |
| MSDM | D145N (synt) | 5' phosphate | + | GGACCCGGGAaatGGACCGAATGATTGCG | 73 |

\* pMS382 was generated from the synthetic gene pMS230 which therefore also needed to be reverted in position 145 from D to N PS4 variant polypeptides with other residues at position 307 are generated using Multi Site Directed Mutagenesis (as described above in Example 3), with the primers in the table below:

| Purpose | Description | Codon | name | Oligo Sequence | SEQ ID NO: | Modification | Strand |
|---|---|---|---|---|---|---|---|
| MSDM | L307K(synt) | aaa | pMS343 | CAAAATGAAGGACAACATaaaTGGCCGCTTCAAGATGGCC | 72 | 5' phosphate | + |

| Purpose | Description | Codon | name | Oligo Sequence | SEQ ID NO: | Modification | Strand |
|---------|-------------|-------|------|----------------|------------|--------------|--------|
| MSDM | L307Q(synt) | cag | pMS344 | GAAGGACAACATcagTGGCCG CTTCAAGATGGCC | 74 | 5' phosphate | + |
| MSDM | L307V(synt) | gtc | pMS345 | GAAGGACAACATGTCTGGCC GCTTCAAGATGGCC | 75 | 5' phosphate | + |
| MSDM | L307W(synt) | tgg | pMS346 | CAAAATGAAGGACAACATtgg TGGCCGCTTCAAGATGGCC | 76 | 5' phosphate | + |
| MSDM | L307Y(synt) | tat | pMS347 | CAAAATGAAGGACAACATtatT GGCCGCTTCAAGATGGCC | 77 | 5' phosphate | + |
| MSDM | L307C(synt) | tgc | pMS348 | CAAAATGAAGGACAACATtgc TGGCCGCTTCAAGATGGCC | 78 | 5' phosphate | + |
| MSDM | L307E(synt) | gaa | pMS371 | CAAAATGAAGGACAACATgaa TGGCCGCTTCAAGATGGCC | 79 | 5' phosphate | + |
| MSDM | L307F(synt) | ttt | pMS349 | GAAGGACAACATtttTGGCCGC TTCAAGATGG | 80 | 5' phosphate | + |
| MSDM | L307H(synt) | cat | pMS370 | GAAGGACAACATcatTGGCCG CTTCAAGATGG | 81 | 5' phosphate | + |

Primer used for site scan in position 307:

| Purpose | Description | Codon | Oligo Sequence | SEQ ID NO: | Modification | Strand |
|---------|-------------|-------|----------------|------------|--------------|--------|
| MSDM | L307NNS (synt) | NNS | CAAAATGAAGGACAACATNN STGGCCGCTTCAAGATGGCC | 82 | 5' phosphate | + |

Example 4

Transformation into *Bacillus subtilis* (Protoplast Transformation)

*Bacillus subtilis* (strain DB104A; Smith et al. 1988; Gene 70, 351-361) is transformed with the mutated plasmids according to the following protocol.

A. Media for Protoplasting and Transformation

| | |
|---|---|
| 2 × SMM | per litre: 342 g sucrose (1 M); 4.72 g sodium maleate (0.04 M); 8:12 g MgCl$_2$,6H$_2$0 (0.04 M); pH 6.5 with concentrated NaOH. Distribute in 50-ml portions and autoclave for 10 min. |
| 4 × YT | 2 g Yeast extract + 3.2 g Tryptone + 0.5 g NaCl per 100 ml. |
| (½ NaCl) | mix equal volumes of 2 × SMM and 4 × YT. |
| SMMP | 10 g polyethyleneglycol 6000 (BDH) or 8000 (Sigma) in |
| PEG | 25 ml 1 × SMM (autoclave for 10 min.). |

B. Media for Plating/Regeneration

| | |
|---|---|
| agar | 4% Difco minimal agar. Autoclave for 15 min. |
| sodium succinate | 270 g/l (1 M), pH 7.3 with HCl. Autoclave for 15 min. |
| phosphate buffer | 3.5 g K$_2$HPO$_4$ + 1.5 g KH$_2$PO$_4$ per 100 ml. Autoclave for 15 min. |
| MgCl$_2$ | 20.3 g MgCl$_2$, 6H$_2$O per 100 ml (1 M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |
| DM3 regeneration medium: mix at 60 C. (waterbath; 500-ml bottle): | 250 ml sodium succinate<br>50 ml casamino acids<br>25 ml yeast extract<br>50 ml phosphate buffer<br>15 ml glucose<br>10 ml MgCl$_2$<br>100 ml molten agar |

Add appropriate antibiotics: chloramphenicol and tetracycline, 5 ug/ml; erythromycin, 1 ug/ml. Selection on kanamycin is problematic in DM3 medium: concentrations of 250 ug/ml may be required.

C. Preparation of Protoplasts

1. Use detergent-free plastic or glassware throughout.
2. Inoculate 10 ml of 2×YT medium in a 100-ml flask from a single colony. Grow an overnight culture at 25-30 C in a shaker (200 rev/min).
3. Dilute the overnight culture 20 fold into 100 ml of fresh 2×YT medium (250-ml flask) and grow until OD$_{600}$=0.4-0.5 (approx. 2 h) at 37 C in a shaker (200-250 rev/min).
4. Harvest the cells by centrifugation (9000 g, 20 min, 4 C).
5. Remove the supernatant with pipette and resuspend the cells in 5 ml of SMMP+5 mg lysozyme, sterile filtered.
6. Incubate at 37 C in a waterbath shaker (100 rev/min). After 30 min and thereafter at 15 min intervals, examine 25 ul samples by microscopy. Continue incubation until 99% of the cells are protoplasted (globular appearance). Harvest the protoplasts by centrifugation (4000 g, 20 min, RT) and pipet off the supernatant. Resuspend the pellet gently in 1-2 ml of SMMP.

The protoplasts are now ready for use. (Portions (e.g. 0.15 ml) can be frozen at −80 C for future use (glycerol addition is not required). Although this may result in some reduction of transformability, 106 transformants per ug of DNA can be obtained with frozen protoplasts).

D. Transformation
1. Transfer 450 ul of PEG to a microtube.
2. Mix 1-10 ul of DNA (0.2 ug) with 150 ul of protoplasts and add the mixture to the microtube with PEG. Mix immediately, but gently.
3. Leave for 2 min at RT, and then add 1.5 ml of SMMP and mix.
4. Harvest protoplasts by microfuging (10 min, 13.000 rev/min (10-12.000 g)) and pour off the supernatant. Remove the remaining droplets with a tissue.

Add 300 ul of SMMP (do not vortex) and incubate for 60-90 min at 37 C in a waterbath shaker (100 rev/min) to allow for expression of antibiotic resistance markers. (The protoplasts become sufficiently resuspended through the shaking action of the waterbath.). Make appropriate dilutions in 1×SSM and plate 0.1 ml on DM3 plates Example 5

Fermentation of PS4 Variants in Shake Flasks

The shake flask substrate is prepared as follows:

| Ingredient | % (w/v) |
| --- | --- |
| Water | — |
| Yeast extract | 2 |
| Soy Flour | 2 |
| NaCl | 0.5 |
| Dipotassium phosphate | 0.5 |
| Antifoam agent | 0.05 |

The substrate is adjusted to pH 6.8 with 4N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flasks are inoculated with the variants and incubated for 24 hours at 35° C./180 rpm in an incubator. After incubation cells are separated from broth by centrifugation (10.000×g in 10 minutes) and finally, the supernatant is made cell free by microfiltration at 0.2 μm. The cell free supernatant is used for assays and application tests.

Example 6

Amylase Assays

Betamyl Assay
One Betamyl unit is defined as activity degrading 0.0351 mmole per 1 min. of PNP-coupled maltopentaose so that 0.0351 mmole PNP per 1 min. can be released by excess α-glucosidase in the assay mix. The assay mix contains 50 ul 50 mM Na-citrate, 5 mM CaCl2, pH 6.5 with 25 ul enzyme sample and 25 ul Betamyl substrate (Glc5-PNP and α-glucosidase) from Megazyme, Ireland (1 vial dissolved in 10 ml water). The assay mix is incubated for 30 min. at 40 C and then stopped by adding 150 ul 4% Tris. Absorbance at 420 nm is measured using an ELISA-reader and the Betamyl activity is calculate based on Activity=A420*d in Betamyl units/ml of enzyme sample assayed.

Endo-amylase Assay
The endo-amylase assay is identical to the Phadebas assay run according to manufacturer (Pharmacia & Upjohn Diagnostics AB).

Exo-specificity
The ratio of exo-amylase activity to Phadebas activity was used to evaluate exo-specificity.

Example 7

Half-life Determination t½ is defined as the time (in minutes) during which half the enzyme activity is inactivated under defined heat conditions. In order to determine the half life of the enzyme, the sample is heated for 1-40 minutes at constant temperatures of 60° C. to 90° C. The half life is calculated based on the residual Betamyl assay.

Procedure: In an Eppendorf vial, 1000 μl buffer is pre-heated for at least 10 minutes at 60° C. or higher. The heat treatment of the sample is started addition of 100 μl of the sample to the preheated buffer under continuous mixing (800 rpm) of the Eppendorf vial in an heat incubator (Termomixer comfort from Eppendorf). After 0, 2, 4, 6, 8 and 9 minutes of incubation, the treatment is stopped by transferring 45 μl of the sample to 1000 μl of the buffer equilibrated at 20° C. and incubating for one minute at 1500 rpm and at 20° C. The residual activity is measured with the Betamyl assay.

Calculation: Calculation of t½ is based on the slope of log 10 (the base-10 logarithm) of the residual Betamyl activity versus the incubation time. t½ is calculated as Slope/0.301=t½.

Example 8

Model System Baking Tests

The doughs are made in the Farinograph at 30.0° C. 10.00 g reformed flour is weighed out and added in the Farinograph; after 1 min. mixing the reference/sample (reference=buffer or water, sample=enzyme+buffer or water) is added with a sterile pipette through the holes of the kneading vat. After 30 sec. the flour is scraped off the edges—also through the holes of the kneading vat. The sample is kneaded for 7 min.

A test with buffer or water is performed on the Farinograph before the final reference is run. FU should be 400 on the reference, if it is not, this should be adjusted with, for example, the quantity of liquid. The reference/sample is removed with a spatula and placed in the hand (with a disposable glove on it), before it is filled into small glass tubes (of approx. 4.5 cm's length) that are put in NMR tubes and corked up. 7 tubes per dough are made.

When all the samples have been prepared, the tubes are placed in a (programmable) water bath at 33° C. (without corks) for 25 min. and hereafter the water bath is set to stay for 5 min. at 33° C., then to heated to 98° C. over 56 min. (1.1° C. per minute) and finally to stay for 5 min. at 96° C.

The tubes are stored at 20.0° C. in a thermo cupboard. The solid content of the crumb was measured by proton NMR using a Bruker NMS 120 Minispec NMR analyser at day 1, 3 and 7 as shown for crumb samples prepared with 0, 05, 1 and 2 ppm PSacD34 in FIG. 2. The lower increase in solid content over time represents the reduction in amylopectin retrogradation. After 7 days of storage at 20.0° C. in a thermo cupboard 10-20 mg samples of crumb weighed out and placed in 40 µl aluminium standard DSC capsules and kept at 20° C.

The capsules are used for Differential Scanning Calorimetry on a Mettler Toledo DSC 820 instrument. As parameters are used a heating cycle of 20-95° C. with 10° C. per min. heating and Gas/flow: $N_2$/80 ml per min. The results are analysed and the enthalpy for melting of retrograded amylopectin is calculated in J/g.

Example 9

Antistaling Effects

Model bread crumbs are prepared and measured according to Example 8. PS4 variants show a strong reduction of the amylopectin retrogradation after baking as measured by Differential Scanning Calorimetry in comparison to the control. The PS4 variants show a clear dosage effect.

Example 10

Recipe for Baking Trials

Baking trials were carried out with a standard white bread sponge and dough recipe for US toast. The sponge dough is prepared from 1400 g of flour "Gold Medal" from General Mills, USA, 800 g of water, 40 g of rape seed oil, 7.5 g GRINDSTED SSL P55 Veg, 10 g emulsifier DIMODAN™ PH200 and 60 g of compressed yeast. The sponge is mixed for 1 min. at low speed and subsequently 3 min. at speed 2 on a Hobart spiral mixer. The sponge is subsequently fermented for 3 hours at 25° C., 85% RH.

Thereafter, 600 g of "Gold Medal" flour, 18 g of compressed yeast, 5 g of calcium propionate, 160 g of sucrose, 5 g of calcium propionate, 432 g of water and ascorbic acid (60 ppm final concentration) and ADA (azodicarbonamide; 40 ppm final concentration) are added to the sponge. The resulting dough is mixed for 1 min. at low speed and then 2 min. on high speed on a Diosna mixer. Then 30 g of salt is added to the dough.

The dough is rested for 5 min. at ambient temperature, and then 550 g dough pieces are scaled, moulded on Glimek sheeter with the settings 1:4, 2:4, 3:15, 4:12 and width 8 on both sides and transferred to a baking form. After 65 min. proofing at 43° C. at 95% RH the doughs are baked for 26 min. at 200° C. in an MIWE oven.

Example 11

Control of Volume of Danish Rolls

Danish Rolls are prepared from a dough based on 2000 g Danish reform flour (from Cerealia), 120 g compressed yeast, 32 g salt, and 32 g sucrose. Water is added to the dough according to prior water optimisation.

The dough is mixed on a Diosna mixer (2 min. at low speed and 5 min. at high speed). The dough temperature after mixing is kept at 26° C. 1350 g dough is scaled and rested for 10 min. in a heating cabinet at 30° C. The rolls are moulded on a Fortuna molder and proofed for 45 min. at 34° C. and at 85% relative humidity. Subsequently the rolls are baked in a Bago 2 oven for 18 min. at 250° C. with steam in the first 13 seconds. After baking the rolls are cooled for 25 min. before weighing and measuring of volume.

The rolls are evaluated regarding crust appearance, crumb homogeneity, capping of the crust, ausbund and specific volume (measuring the volume with the rape seed displacement method).

Based on these criteria it is found that the PS4 variants increase the specific volume and improve the quality parameters of Danish rolls. Thus PS4 variants are able to control the volume of baked products.

Example 12

Protocol for Evaluation of Firmness, Resilience and Cohesiveness

Texture Profile Analysis of Bread

Firmness, resilience and cohesiveness are determined by analysing bread slices by Texture Profile Analysis using a Texture Analyser From Stable Micro Systems, UK. Calculation of firmness and resilience is done according to preset standard supplied by Stable Micro System, UK. The probe used is aluminium 50 mm round.

Bread is sliced with the width of 12.5 mm. The slices are stamped out to a circular piece with a diameter of 45 mm and measured individually.

The following settings are used:
Pre Test Speed: 2 mm/s
Test Speed: 2 mm/s
Post Test Speed: 10 mm/s
Rupture Test Distance: 1%
Distance: 40%
Force: 0.098 N
Time: 5.00 sec
Count: 5
Load Cell: 5 kg
Trigger Type Auto—0.01 N The mode of compression is a modification to the one used in Standard method AACC 74-09. The sample is compressed twice in the test. FIG. 1 shows an example of a curve from the Texture Analyser.

Example 13

Protocol for Evaluation of Firmness

Firmness is determined at 40% compression during the first compression. The figure is the force needed to compress the slice to 40% of the total thickness. The lower the value, the softer the bread. The firmness is expressed as a pressure, for example, in hPa.

This assay may be referred to as the "Firmness Evaluation Protocol".

Example 14

Protocol for Evaluation of Resilience

Area under the curve is a measure of work applied during the test. The area under the curve in the compression part (A1) and the withdrawal part (A2) during the first compression are shown in FIG. 1.

The ratio between A1 and A2 is defined as the resilience of the sample, and is expressed as Resilience Units. True elastic material will give a symmetric curve, as the force applied during the first part will be equal to the force in the second part. For bread and bread-like material, A2 is normally smaller than A2 due to disturbance of the structure during compression. Hence, resilience is always lower than 1.

This assay may be referred to as the "Resilience Evaluation Protocol".

Example 15

Protocol for Evaluation of Cohesiveness

The cohesiveness is defined as the ratio between the area under second compression to the area under first compression (A3 μl+A2), and is expressed as Cohesiveness Units. It is a measure of the decay of the sample during compression. The higher the ability of the sample to regain its shape after first compression the closer the value will be to 1. For bread and bread-like material cohesiveness is always lower than 1.

This assay may be referred to as the "Cohesiveness Evaluation Protocol".

Example 16

Protocol for Evaluation of Crumbliness (Resistance to Crumbling)

Two slices of bread are placed on a piece of paper. Each slice is divided into 4 squares by vertical and subsequent horizontal tears of the slice.

Tearing is done by pulling the crumb apart by the fingers. First the slice is torn from the middle of the top bread surface to the middle of the bottom bread surface. Thereafter, each half of the original slice is torn from the crust side to the inside of the slice. The small crumb pieces, which are separated from the 4 squares, are removed by shaking each piece after a tear at least 3 times by moving the hand up and down.

The weight of the separated small crumb pieces is determined as a measure of crumbliness. This assay may be referred to as the "Crumbliness Evaluation Protocol".

Example 17

Protocol for Evaluation of Foldability

The toast bread is sliced using an automatic bread slicer with set slice thickness of 15 mm. The slice is folded by hand from the top of the slice towards the bottom, so that the direction of the crease is from side to side.

The foldability is visually assessed using the following scoring system:

| Score | Feature |
| --- | --- |
| 1 | Unfoldable, slice breaks upon folding |
| 2 | Foldable, whole slice breaks within 5 seconds after folding |
| 3 | Foldable, part of the slice breaks within 5 seconds after folding. Other parts break later. |
| 4 | Foldable, part of the slice breaks later than 5 seconds after folding. Other parts do not break. |
| 5 | Foldable, no part of the slice break after folding |

This assay may be referred to as the "Foldability Evaluation Protocol".

Example 18

Improved Thermostability of PS4 Variant Polypeptides

Thermal stability of amylase pSac-pMS382 is measured as described above and compared to that of pSac-D34/pMD3 (SEQ ID NO: 2) and pSac-pMD229 (SEQ ID NO: 13).

Because heat inactivation follows a $1^{st}$ order reaction, half-life defined as the time (in minutes) for 50% inactivation is determined based on residual activity using the Betamyl assay after incubation for 1-40 minutes at 75, 80 and 85° C. (167, 176 and 185° F., respectively) in 50 mM sodium-citrate, 5 mM calcium chloride, pH 6.5.

Figure 2:
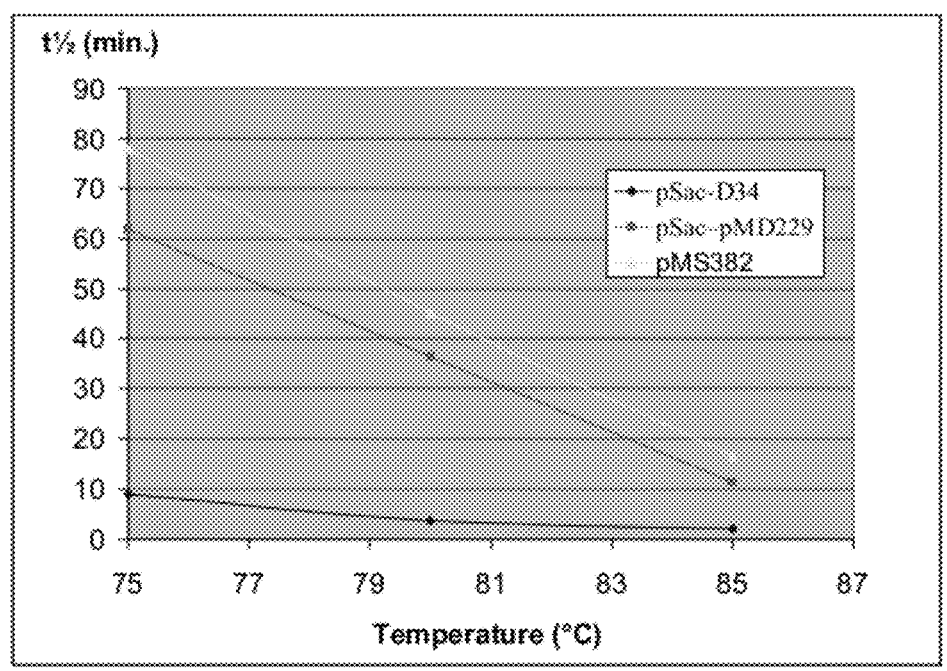
FIG. 2 shows the results of an experiment to determine the temperature stability of the PS4 variant polypeptides described here. X-axis: temperature, Y-axis: half-life (minutes). Diamonds: pSac-D34/pMD3 (SEQ ID NO: 2), Squares: pSac-pMD229 (SEQ ID NO: 13), Triangles: pSac-pMS382 (SEQ ID NO: 21)

The results are shown in FIG. 2. This figure shows that the thermostability (half life) of PS4 variant polypeptides comprising a substitution at position 307 to a basic or positively charged amino acid is improved compared to polypeptides without such a mutation.

Example 19

Improved Handling Properties of Food Products Treated with PS4 Variant Polypeptides Firmness Bread is baked with varying amounts of pSac-pMS382 (SEQ ID NO: 21) comprising a substitution to a basic or positively charged residue at position 307, i.e., 20,000, 40,000 and 60,000 Betamyl units/kg of pSac-pMS382.

The firmness of the bread is tested according to the protocol set out in Example 13 at various times after baking. As a control, firmness of bread baked without any enzyme is also measured.

Figure 3:
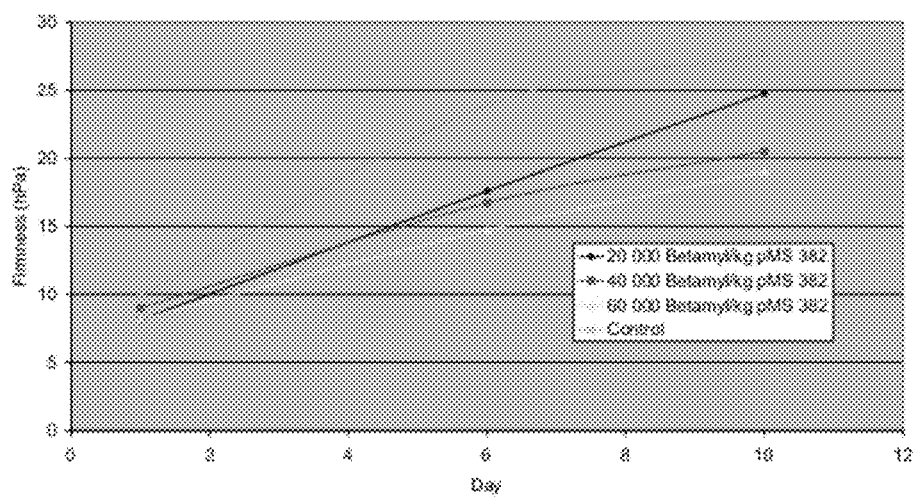
FIG. 3 shows the results of a baking trial in which firmness of bread treated with various concentrations of PS4 variant polypeptide and untreated bread are tested. The X-axis shows the number of days, while the Y-axis shows firmness expressed as hPa (see Example 13). Diamond: 20,000 Betamyl units/kg of pSac-pMS382. Square: 40,000 Betamyl units/kg of pSac-pMS382. Triangle: 60,000 Betamyl units/kg of pSac-pMS382. Cross: Control (no enzyme).

FIG. 3 shows the results of a baking trial in which firmness of bread is tested.

Example 20

Improved Handling Properties of Food Products Treated with PS4 Variant Polypeptides Resilience Bread is baked with varying amounts of pSac-pMS382 (SEQ ID NO: 21) comprising a substitution to a basic or positively charged residue at position 307, i.e., 20,000, 40,000 and 60,000 Betamyl units/kg of pSac-pMS382.

The resilience of the bread is tested according to the protocol set out in Example 14 at various times after baking. As a control, resilience of bread baked without any enzyme is also measured.

Figure 4:
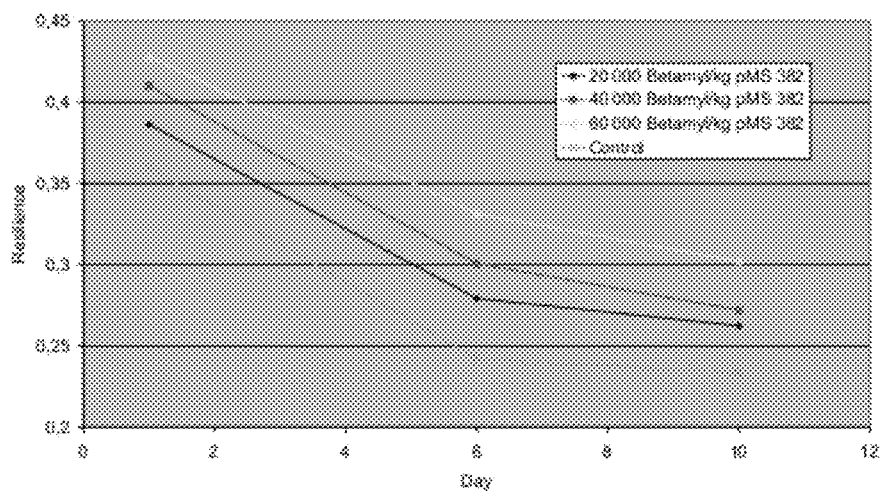
FIG. 4 shows the results of a baking trial in which resilience of bread treated with various concentrations of PS4 variant polypeptide and untreated bread are tested. The X-axis shows the number of days, while the Y-axis shows resilience expressed as Resilience Units (see Example 14). Diamond: 20,000 Betamyl units/kg of pSac-pMS382. Square: 40,000 Betamyl units/kg of pSac-pMS382. Triangle: 60,000 Betamyl units/kg of pSac-pMS382. Cross: Control (no enzyme).

FIG. 4 shows the results of a baking trial in which resilience of bread is tested.

Example 21

Improved Handling Properties of Food Products Treated with PS4 Variant Polypeptides Cohesiveness Bread is baked with varying amounts of pSac-pMS382 (SEQ ID NO: 21) comprising a substitution to a basic or positively charged residue at position 307, i.e., 20,000, 40,000 and 60,000 Betamyl units/kg of pSac-pMS382.

The cohesiveness of the bread is tested according to the protocol set out in Example 15 at various times after baking. As a control, cohesiveness of bread baked without any enzyme is also measured.

Figure 5:
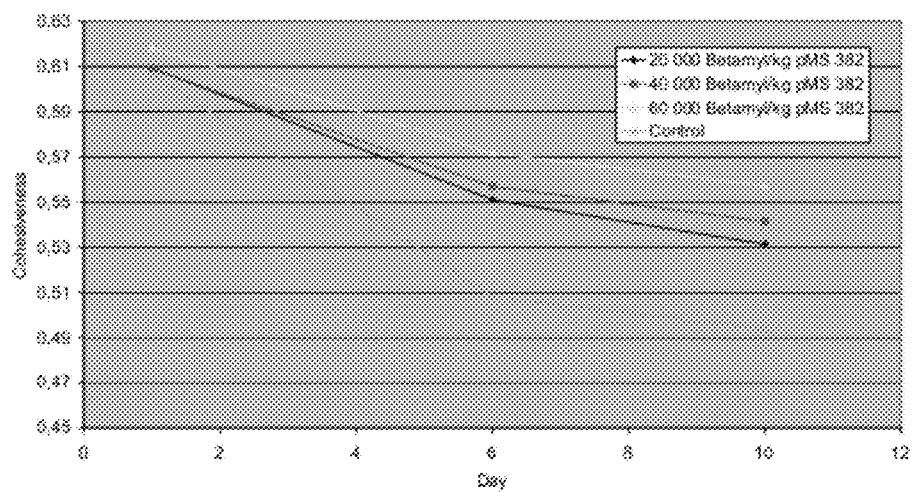
FIG. 5 shows the results of a baking trial in which cohesiveness of bread treated with various concentrations of PS4 variant polypeptide and untreated bread are tested. The X-axis shows the number of days, while the Y-axis shows cohesiveness expressed as Cohesiveness Units (see Example 15). Diamond: 20,000 Betamyl/kg of pSac-pMS382. Square: 40,000 Betamyl/kg of pSac-pMS382. Triangle: 60,000 Betamyl/kg of pSac-pMS382. Cross: Control (no enzyme).

FIG. 5 shows the results of a baking trial in which cohesiveness of bread is tested.

Example 22

Improved Handling Properties of Food Products Treated with PS4 Variant Polypeptides Firmness Bread is baked with 60,000 Betamyl units/kg of pSac-pMS382 (SEQ ID NO: 21) comprising a substitution to a basic or positively charged residue at position 307 and the firmness of the bread is tested according to the protocol set out in Example 13 at various times after baking.

Bread is also baked with 60,000 Betamyl units/kg of pSac-D34/pMD3 (SEQ ID NO: 2) and 60,000 Betamyl units/kg of pSac-pMD229 (SEQ ID NO: 13), each without a substitution at position 307 to a basic or positively charged amino acid. The firmness of the bread is tested.

As a control, firmness of bread baked without any enzyme is also measured.

Figure 6:
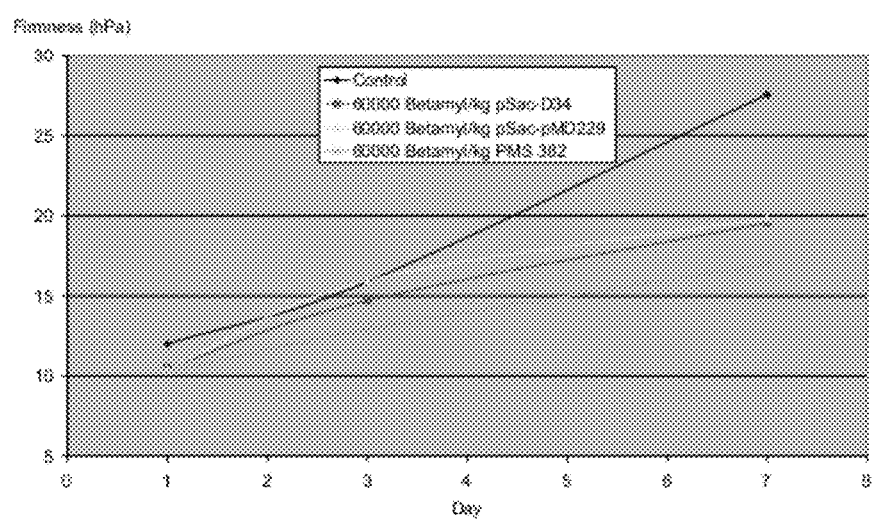
FIG. 6 shows the results of a baking trial in which firmness of bread treated with PS4 variant polypeptide with substitution at 307 is tested. The X-axis shows the number of days, while the Y-axis shows firmness expressed as hPa (see Example 13). Diamond: Control (no enzyme). Square: 60,000 Betamyl units/kg pSac-D34/pMD3 (SEQ ID NO: 2). Triangle: 60,000 Betamyl units/kg of pSac-pMD229 (SEQ ID NO: 13). Cross: 60,000 Betamyl units/kg of pSac-pMS382.

FIG. 6 shows the results of a baking trial in which firmness of bread treated with PS4 variant polypeptide with and without substitution at 307 is tested.

Example 23

Improved Handling Properties of Food Products Treated with PS4 Variant Polypeptides Firmness, Resilience and Cohesiveness Bread is baked with 60,000 Betamyl units/kg of pSac-pMS382 (SEQ ID NO: 21) comprising a substitution to a basic or positively charged residue at position 307 and the resilience of the bread is tested according to the protocol set out in Example 14 at various times after baking.

Bread is also baked with 60,000 Betamyl units/kg of pSac-D34/pMD3 (SEQ ID NO: 2) and 60,000 Betamyl units/kg of pSac-pMD229 (SEQ ID NO: 13), each without a substitution at position 307 to a basic or positively charged amino acid. The resilience of the bread is tested.

As a control, resilience of bread baked without any enzyme is also measured.

Figure 7:
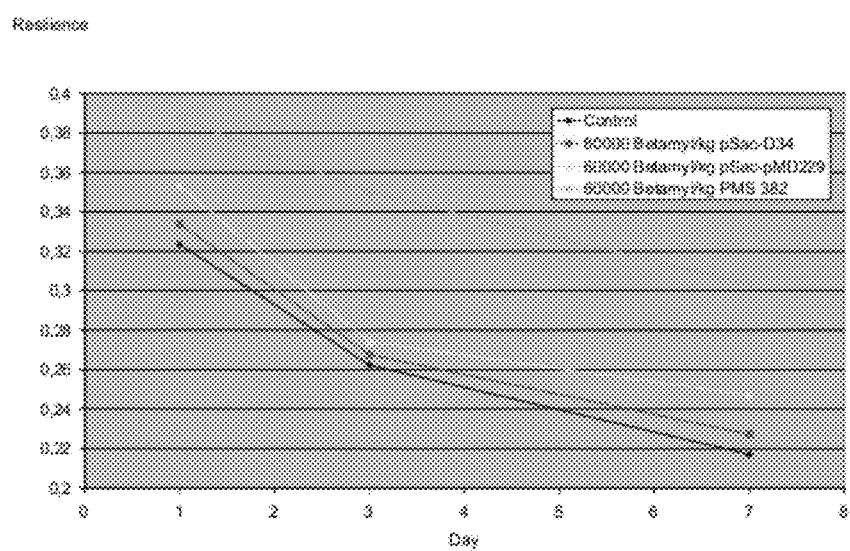
FIG. 7 shows the results of a baking trial in which resilience of bread treated with PS4 variant polypeptide with substitution at 307 is tested. The X-axis shows the number of days, while the Y-axis shows resilience expressed as resilience units (see Example 14). Diamond: Control (no enzyme). Square: 60,000 Betamyl units/kg pSac-D34/pMD3 (SEQ ID NO: 2). Triangle: 60,000 Betamyl units/kg of pSac-pMD229 (SEQ ID NO: 13). Cross: 60,000 Betamyl units/kg of pSac-pMS382.

FIG. 7 shows the results of a baking trial in which resilience of bread treated with PS4 variant polypeptide with and without substitution at 307 is tested.

Example 24

Improved Handling Properties of Food Products Treated with PS4 Variant Polypeptides Cohesiveness Bread is baked with 60,000 Betamyl units/kg of pSac-pMS382 (SEQ ID NO: 21) comprising a substitution to a basic or positively charged residue at position 307 and the cohesiveness of the bread is tested according to the protocol set out in Example 15 at various times after baking.

Bread is also baked with 60,000 Betamyl units/kg of pSac-D34/pMD3 (SEQ ID NO: 2) and 60,000 Betamyl units/kg of pSac-pMD229 (SEQ ID NO: 13), each without a substitution at position 307 to a basic or positively charged amino acid. The cohesiveness of the bread is tested.

As a control, cohesiveness of bread baked without any enzyme is also measured.

Figure 8:
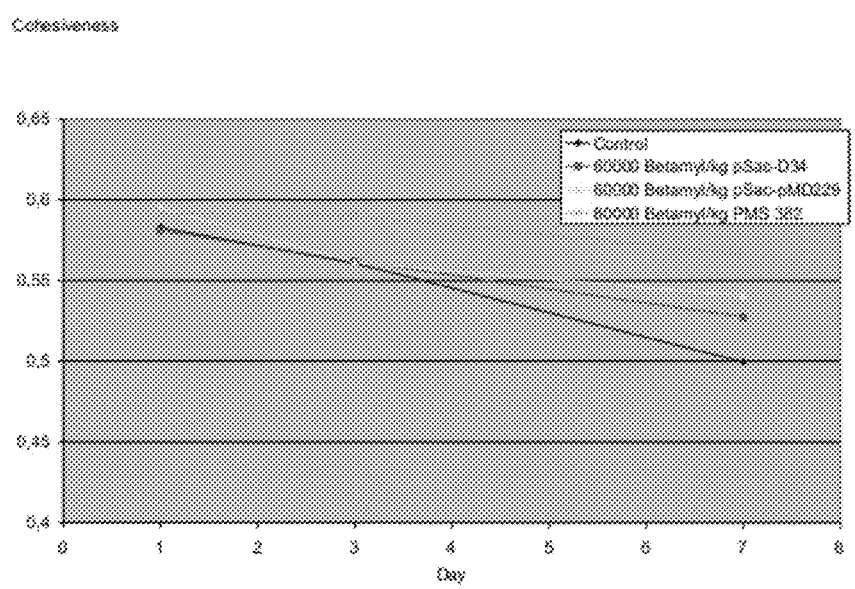
FIG. 8 shows the results of a baking trial in which cohesiveness of bread treated with PS4 variant polypeptide with substitution at 307 is tested. The X-axis shows the number of days, while the Y-axis shows cohesiveness expressed as cohesiveness units (see Example 15). Diamond: Control (no enzyme). Square: 60,000 Betamyl units/kg pSac-D34/pMD3 (SEQ ID NO: 2). Triangle: 60,000 Betamyl units/kg of pSac-pMD229 (SEQ ID NO: 13). Cross: 60,000 Betamyl units/kg of pSac-pMS382.

FIG. 8 shows the results of a baking trial in which cohesiveness of bread treated with PS4 variant polypeptide with and without substitution at 307 is tested.

Example 25

Improved Handling Properties of Food Products Treated with PS4 Variant Polypeptides Foldability Sponge and dough toast bread treated with 4 ppm of pSac-pMS382 (SEQ ID NO: 21, H307K substitution) is baked and foldability of the resulting breads is tested and scored as described above.

As a control, sponge and dough toast bread not treated with enzyme is baked and foldability tested and scored.

Tests are done on three slices on day 13 after baking.

| Enzyme Applied | Average Foldability Score |
|---|---|
| 4 ppm pSac-pMS382 | 3 |
| Control (no enzyme) | 1 |

As shown in the table above and Figures, foldability is improved in sponge and dough toast bread treated with a PS4 variant polypeptide comprising a substitution at position 307 to a basic or positively charged amino acid compared to untreated toast bread.

Example 26

Improved Handling Properties of Food Products Treated with PS4 Variant Polypeptides Foldability Sponge and dough toast bread treated with 4 ppm of pSac-pMS382 (SEQ ID NO: 21, H307K substitution) is baked and foldability of the resulting breads is tested and scored as described above.

As controls, sponge and dough toast bread not treated with enzyme is baked and foldability tested and scored. Foldability of sponge and dough toast breads treated with other enzymes as shown below is also tested.

Enzyme pSac-D34 (also known as pMD3) comprises mutations N33Y, D34N, G121D, G134R, A141P, I157L, L178F, A179T, G223A, H307L, S334P relative to wild type non-maltogenic exoamylase and its sequence is shown as SEQ ID NO: 2.

Enzyme pSac-pMD229 comprises mutations N33Y, D34N, G121F, G134R, A141P, Y146G, I157L, S161A, L178F, A179T, G223E, S229P, H272Q, G303E, H307L, A309P, S334P relative to wild type non-maltogenic exoamylase and its sequence is shown as SEQ ID NO: 13.

Tests are done on three slices on day 8 after baking.

| Enzyme Applied | Average Foldability score |
|---|---|
| pSac-pMS382 (SEQ ID NO: 21) | 5 |
| pSac-pMD229 (SEQ ID NO: 13) | 3 |
| pSac-D34/pMD3 (SEQ ID NO: 2) | 2 |
| Control (no enzyme) | 1 |

As shown in the table above, foldability is improved in sponge and dough toast bread treated with a PS4 variant polypeptide comprising a substitution at position 307 to a basic or positively charged amino acid compared to enzymes without this substitution.

Example 27

Improved Handling Properties of Food Products Treated with Combinations of PS4 Variant Polypeptides and Other Enzymes: Foldability Sponge and dough toast bread treated with 6 ppm of pSac-pMS382 (SEQ ID NO: 21, 307K substitution) alone or in combination with other enzymes as shown below is baked and foldability of the resulting breads is tested and scored as described above.

Combination 1: 6 ppm pSac-pMS382+50 ppm GRIND-AMYL™ POWERBake 900+15 ppm GRINDAMYL™ Max-Life U4.

Combination 2: 6 ppm pSac-pMS382+50 ppm GRIND-AMYL™ POWERBake 900

Combination 3: 6 ppm pSac-pMS382+50 ppm GRIND-AMYL™ POWERBake 900+150 ppm GRINDAMYL™ POWERBake 4050

GRINDAMYL™ POWERBake 900 is a xylanase commercially available from Danisco A/S. GRINDAMYL™ Max-Life U4 is a bacterial α-amylase commercially available from Danisco A/S. GRINDAMYL™ POWERBake 4050 is a lipase commercially available from Danisco A/S.

As controls, sponge and dough toast bread not treated with enzyme is baked and foldability tested and scored.

Tests are done on three slices on day 5 after baking.

| Enzyme Applied | Average Foldability Score |
| --- | --- |
| 6 ppm pSac-pMS382 | 4 |
| 6 ppm pSac-pMS382 + 50 ppm POWERBake 900 + 15 ppm Max-Life U4 | 5 |
| 6 ppm pSac-pMS382 + 50 ppm POWERBake 900 | 5 |
| 6 ppm pSac-pMS382 + 50 ppm POWERBake 900 + 150 ppm POWERBake 4050 | 5 |
| Control (no enzyme) | 1 |

As shown in the table above, foldability is improved in sponge and dough toast bread treated with a PS4 variant polypeptide comprising a substitution at position 307 to a basic or positively charged amino acid alone or in combination with other enzymes such as bacterial α-amylase, lipase and xylanase.

Example 28

Improved Handling Properties of Food Products Treated with PS4

Variant Polypeptides Crumbliness Tests

Sponge and dough toast bread treated with 4 ppm of pSac-pMS382 (SEQ ID NO: 21,307K substitution) is baked and crumbliness of the resulting breads is tested and scored as described above.

As a control, sponge and dough toast bread not treated with enzyme is baked and foldability tested and scored.

Tests are done on day 13 after baking.

| Enzyme applied | Weight of Separated Crumb in mg |
| --- | --- |
| Control (no enzyme) | 23 |
| 4 ppm pSac-pMS382 | 13 |

As shown in the table above, crumbliness is reduced in sponge and dough toast bread after 13 days, treated with a PS4 variant polypeptide comprising a substitution at position 307 to a basic or positively charged amino acid.

Example 29

Improved Handling Properties of Food Products Treated with PS4 Variant Polypeptides Crumbliness Tests Sponge and dough toast bread treated with 4 ppm of pSac-pMS382 (SEQ ID NO: 21,307K substitution) is baked and crumbliness of the resulting breads is tested and scored as described above.

As a control, sponge and dough toast bread not treated with enzyme is baked and foldability tested and scored.

Tests are done on day 15 after baking.

| Enzyme applied | Weight of Separated Crumb in mg |
| --- | --- |
| Control (no enzyme) | 41 |
| 4 ppm pSac-pMS382 | 9 |

As shown in the table above, crumbliness is reduced in sponge and dough toast bread after 15 days, treated with a PS4 variant polypeptide comprising a substitution at position 307 to a basic or positively charged amino acid.

Example 30

PS4 Variant Polypeptides with Position 307K Substitutions

The following polypeptides with substitutions at position 307 to lysine are made and their properties tested as described above. The sequences of the polypeptides comprise the sequence of SEQ ID NO: 2 together with the substitutions specified.

| Variant | Mutations (of SEQ ID NO: 2) |
| --- | --- |
| SSM471C04 | N33Y, D34N, G121F, G134R, A141P, Y146G, I157L, S161A, L178F, A179T, G223E, S229P, H272Q, G303E, H307K, A309P, S334P |
| pMS343 | N33Y, D34N, G121F, G134R, A141P, Y146G, I157L, S161A, L178F, A179T, G223E, S229P, H272Q, G303E, H307K, A309P, S334P |
| pMS358 | N33Y, D34N, G121F, G134R, A141P, N145D, Y146G, I157L, S161A, L178F, A179T, G223E, S229P, H272Q, H307K, A309P, S334P |
| pMS361 | N33Y, D34N, G121F, G134R, A141P, N145D, Y146G, I157L, S161A, L178F, A179T, G223E, S229P, H272Q, G303E, H307K, A309P, S334P |
| pMS364 | N33Y, D34N, G121F, G134R, A141P, N145D, Y146G, I157L, S161A, L178F, A179T, G223E, S229P, H272Q, H307K, A309P, S334P |
| pMS366 | N33Y, D34N, G121F, G134R, A141P, Y146G, I157L, S161A, L178F, A179T, G223E, S229P, H272Q, H307K, A309P, S334P |
| pMS368 | N33Y, D34N, G121F, G134R, A141P, N145D, Y146G, I157L, G158T, S161A, L178F, A179T, G223E, S229P, H272Q, G303E, H307K, A309P, S334P |
| pMS359 | N33Y, D34N, D68C, G121F, G134R, A141P, Y146G, I157L, S161A, L178F, A179T, G223E, S229P, H272Q, G303E, H307K, A309P, S334P |
| pMS360 | N33Y, D34N, D68C, G121F, G134R, A141P, Y146G, I157L, S161A, L178F, A179T, G223E, S229P, H272Q, H307K, A309P, S334P |
| pMS362 | N33Y, D34N, D68C, G121F, G134R, A141P, Y146G, I157L, S161A, L178F, A179T, G223E, S229P, H272Q, G303E, H307K, A309P, S334P |

| Variant | Mutations (of SEQ ID NO: 2) |
|---|---|
| pMS363 | N33Y, D34N, D68C, G121F, G134R, A141P, N145D, Y146G, I157L, G158T, S161A, L178F, A179T, G223E, S229P, H272Q, G303E, H307K, A309P, S334P |
| pMS365 | N33Y, D34N, D68C, G121F, G134R, A141P, Y146G, I157L, G158T, S161A, L178F, A179T, G223E, S229P, H272Q, H307K, A309P, S334P |
| pMS367 | N33Y, D34N, D68C, G121F, G134R, A141P, N145D, Y146G, I157L, S161A, L178F, A179T, G223E, S229P, H272Q, G303E, H307K, A309P, S334P |
| pMS369 | N33Y, D34N, G70D, G121F, G134R, A141P, Y146G, I157L, S161A, L178F, A179T, G223E, S229P, G303E, H307K, A309P, S334P |
| pMS380 | N33Y, D34N, G121F, G134R, A141P, N145D, Y146G, I157L, S161A, L178F, A179T, G223E, S229P, H307K, A309P, S334P |
| pMS383 | N33Y, D34N, G70K, G121F, G134R, A141P, N145D, Y146G, I157L, S161A, L178F, A179T, G223E, S229P, H307K, A309P, S334P |
| pMS384 | N33Y, D34N, G70K, G121F, G134R, A141P, N145D, Y146G, I157L, S161A, L178F, A179T, G223E, S229P, H272Q, H307K, A309P, S334P |
| pMS385 | N33Y, D34N, G121F, G134R, A141P, N145D, Y146G, I157L, S161A, L178F, A179T, G223E, S229P, H272Q, H307K, A309P, S334P |
| pMS372 | N33Y, D34N, G121F, G134R, A141P, N145D, Y146G, I157L, S161A, L178F, A179T, Y198W, G223E, S229P, H272Q, H307K, A309P, S334P |
| pMS381 | N33Y, D34N, G70K, G121F, G134R, A141P, N145D, Y146G, I157L, S161A, L178F, A179T, G223E, S229P, H272Q, H307K, A309P, S334P |
| pMS391 | N33Y, D34N, G70K, G121F, G134R, A141P, Y146G, I157L, S161A, L178F, A179T, G223E, S229P, H272Q, H307K, A309P, S334P |
| pMS382 | N33Y, D34N, G70D, G121F, G134R, A141P, Y146G, I157L, S161A, L178F, A179T, G223E, S229P, H307K, A309P, S334P |
| pMS386 | N33Y, D34N, G70K, G121F, G134R, A141P, N145D, Y146G, I157L, S161A, L178F, A179T, Y198W, G223E, S229P, H272Q, H307K, A309P, S334P |
| pMS387 | N33Y, D34N, G70D, G121F, G134R, A141P, N145D, Y146G, I157L, S161A, L178F, A179T, G223E, S229P, H272Q, H307K, A309P, S334P |
| pMS388 | N33Y, D34N, G70D, G121F, G134R, A141P, N145D, Y146G, I157L, S161A, L178F, A179T, Y198W, G223E, S229P, H272Q, H307K, A309P, S334P |
| pMS390 | N33Y, D34N, G70K, G121F, G134R, A141P, N145D, Y146G, I157L, S161A, L178F, A179T, G223E, S229P, H272Q, H307K, A309P, S334P |
| pMS392 | N33Y, D34N, G121F, G134R, A141P, N145D, Y146G, I157L, S161A, L178F, A179T, G223E, S229P, H272Q, H307K, A309P, S334P |
| pMS393 | N33Y, D34N, G70D, G121F, G134R, A141P, N145D, Y146G, I157L, S161A, L178F, A179T, Y198W, G223E, S229P, H272Q, H307K, A309P, S334P |
| pMS382 | N33Y, D34N, G70D, G121F, G134R, A141P, Y146G, I157L, S161A, L178F, A179T, G223E, S229P, H307K, A309P, S334P |
| pMS389 | N33Y, D34N, G121F, G134R, A141P, N145D, Y146G, I157L, S161A, L178F, A179T, G223E, S229P, H272Q, H307K, A309P, S334P |
| pMS390 | N33Y, D34N, G70K, G121F, G134R, A141P, N145D, Y146G, I157L, S161A, L178F, A179T, G223E, S229P, H272Q, H307K, A309P, S334P |

Example 31

PS4 Variant Polypeptides with Position 307H

The following polypeptides with histidine at position 307 together with other mutations are made and their properties tested as described above. The sequences of the polypeptides comprise the sequence of SEQ ID NO: 2 together with the substitutions specified.

| Variant | Mutations (of SEQ ID NO: 2) |
|---|---|
| pMS375 | N33Y, D34N, G70D, G121F, G134R, A141P, N145D, Y146G, I157L, S161A, L178F, A179T, G223E, S229P, H272Q, H307H, A309P, S334P |
| pMS376 | N33Y, D34N, G121F, G134R, A141P, N145D, Y146G, I157L, S161A, L178F, A179T, G223E, S229P, H272Q, H307H, A309P, S334P |
| pMS379 | N33Y, D34N, G121F, G134R, A141P, N145D, Y146G, I157L, S161A, L178F, A179T, G223E, S229P, H272Q, H307H, A309P, S334P |
| pMS394 | N33Y, D34N, G121F, G134R, A141P, Y146G, I157L, S161A, L178F, A179T, G223E, S229P, H272Q, H307H, A309P, S334P |
| pMS395 | N33Y, D34N, G70D, G121F, G134R, A141P, Y146G, I157L, S161A, L178F, A179T, Y198W, G223E, S229P, H272Q, H307H, A309P, S334P |
| pMS396 | N33Y, D34N, G70D, G121F, G134R, A141P, N145D, Y146G, I157L, S161A, L178F, A179T, G223E, S229P, H272Q, H307H, A309P, S334P |

| Variant | Mutations (of SEQ ID NO: 2) |
|---|---|
| pMS397 | N33Y, D34N, G121F, G134R, A141P, N145D, Y146G, I157L, S161A, L178F, A179T, G223E, S229P, H272Q, H307H, A309P, S334P |
| pMS396 | N33Y, D34N, G70D, G121F, G134R, A141P, N145D, Y146G, I157L, S161A, L178F, A179T, G223E, S229P, H272Q, H307H, A309P, S334P |

Example 32

Generation of PS4 Polypeptides with L307R and L307K Mutations

SSM 471 B10 and SSM 471 C04 with other residues at position 307 (L307R, L307K) are generated using Multi Site Directed Mutagenesis (as described above in Example 3), with the primers in the table below Primer used for site scan in position 307:

| Purpose | Description | Codon | Oligo Sequence | SEQ ID NO: | Modification | Strand |
|---|---|---|---|---|---|---|
| MSDM | L307NNS (synt) | NNS | CAAAATGAAGGACAACATNN STGGCCGCTTCAAGATGGCC | 82 | 5' phosphate | + |

96 clones from the Site Scan library are sequenced and the two variants SSM 471 BIO and SSM 471 C04 containing amino acid R and K respectively in position 307 are identified.

The amino acid sequence of SSM471 B10 is set out as SEQ ID NO: 27, while the nucleic acid sequence of SSM471 B10 is set out as SEQ ID NO: 28.

The amino acid sequence of SSM471 C04 is set out as SEQ ID NO: 29, while the nucleic acid sequence of SSM471 C04 is set out as SEQ ID NO: 30.

Other PS4 variant polypeptides derived from a parent polypeptide and with mutations L307R or L307K are likewise generated using Multi Site Directed Mutagenesis (as described above in Example 3), with the primers in the table below:

Primer Used for Site Scan in Position 307

Primer used for site scan in position 307:

| Purpose | Description | Codon | Oligo Sequence | SEQ ID NO: | Modification | Strand |
|---|---|---|---|---|---|---|
| MSDM | L307NNS (synt) | NNS | CAAAATGAAGGACAACATNN STGGCCGCTTCAAGATGGCC | 82 | 5' phosphate | + |

For polypeptides with an additional mutation in the region of 301 to 306 or 308 to 313, the additional mutation is generated by Multi Site Directed Mutagenesis (according to the method described in Example 3).

96 clones from the Site Scan libraries are sequenced and thereby variants containing amino acid R and K, respectively in position 307 are identified.

Example 33

Tortilla Trial

Tortillas are baked to a recipe as follows:

| | Baker's % | |
|---|---|---|
| Ingredients | Control | Test |
| Flour | 100.00 | 100.00 |
| Salt | 2.00 | 2.00 |
| Sodium Bicarbonate | 1.00 | 1.00 |
| Sodium Acid Pyrophosphate 28 | 0.45 | 0.45 |
| Fumaric Acid | 0.65 | 0.65 |
| Potassium Sorbate | 0.40 | 0.40 |
| PANODAN ® POWERBake 808 K1 | 0.40 | 0.40 |
| Calcium Propionate | 0.40 | 0.40 |
| All Purpose Shortening | 13.00 | 13.00 |

| | Baker's % | |
|---|---|---|
| Ingredients | Control | Test |
| Water | 56.00 | 56.00 |
| Novamyl ™ 1500 | 400 ppm | — |
| pSac-pMS382 (SEQ ID NO: 21) (EDS 201) | — | 100 ppm |

Procedure

Dough temperature must be 30° C. Put all dry ingredients into aK emper mixer and mix for 1 min slow. Add water—mix 12 min slow. Scaling: 1350 g. Moulding: Glimek: Press time 3.0–rounding time: 3.0. Rest dough 10 min at 30° C. Pass the dough balls trough the CFO 40 tortilla machine:

Settings:

Pressing: Hot press the dough balls:

Top plate: 205° C.; Bottom plate: 200° C.

Conveyers:

Top: 230° C.; Middle: 225° C.; Bottom: 160° C.

Baking time Approx 30 seconds

Cooling: 12 min. at: 20° C., 80% RH

Packing: Vacuum With CO2

Settings: Vacuum: 40; CO2: 41; Temp: 82° C.

Example 34

Results of Foldability Test Day 8 After Baking

A foldability test is conducted at day 8 after baking according to Example 17.

Figure 9:
FIG. 9. Foldability test day 8 after baking of tortillas with 400 ppm Novamyl™ 1500 and 50 BMK/kg pSac-pMS382 (SEQ ID NO: 21).
Figure 10:
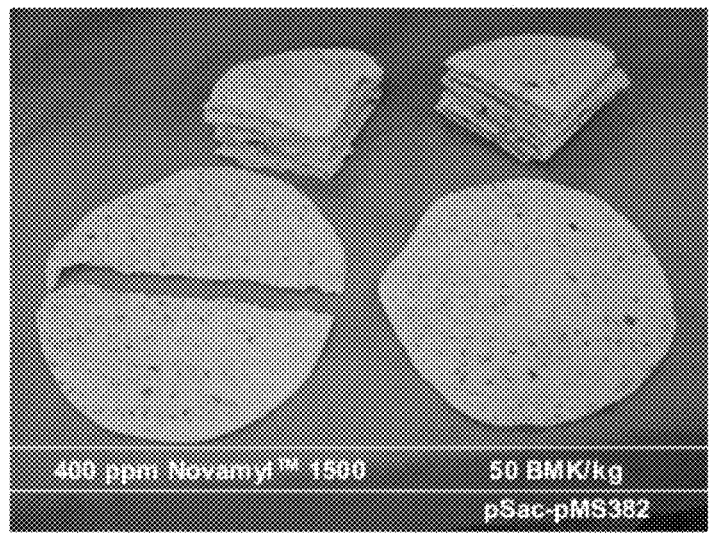
FIG. 10. Foldability test day 8 after baking of tortillas with 400 ppm Novamyl™ 1500 and 50 BMK/kg pSac-pMS382 (SEQ ID NO: 21).

FIG. 9 shows the results of a foldability test day 8 after baking of tortillas with 400 ppm Novamyl™ 1500 and 50 BMK/kg pSac-pMS382 (SEQ ID NO: 21). FIG. 10 shows the results of a foldability test day 8 after baking of tortillas with 400 ppm Novamyl™ 1500 and 50 BMK/kg pSac-pMS382 (SEQ ID NO: 21).

When 10 tortillas with 400 ppm of Novamyl™ 1500 are folded, all cracked during folding as shown in FIGS. 9 and 10.

When 10 tortillas with 50 BMK/kg pSac-pMS382 (SEQ ID NO: 21) are folded, none cracked during folding as shown in FIGS. 9 and 10.

Example 35

Baking Trial with SSM 471 B10 (SEQ ID NO: 27, 307R) and SSM 471 C04 (SEQ ID NO: 29, 307K)

US toast prepared by a sponge and dough procedure as described in Example 10 is used to test the variants SSM 471 B10 (SEQ ID NO: 27) with 307R and SSM 471 C04 (SEQ ID NO: 29) with 307K at a 40 BMK/kg dosage.

The toast is evaluated for firmness and resilience as described in Examples 12 to 14.

Figure 11:
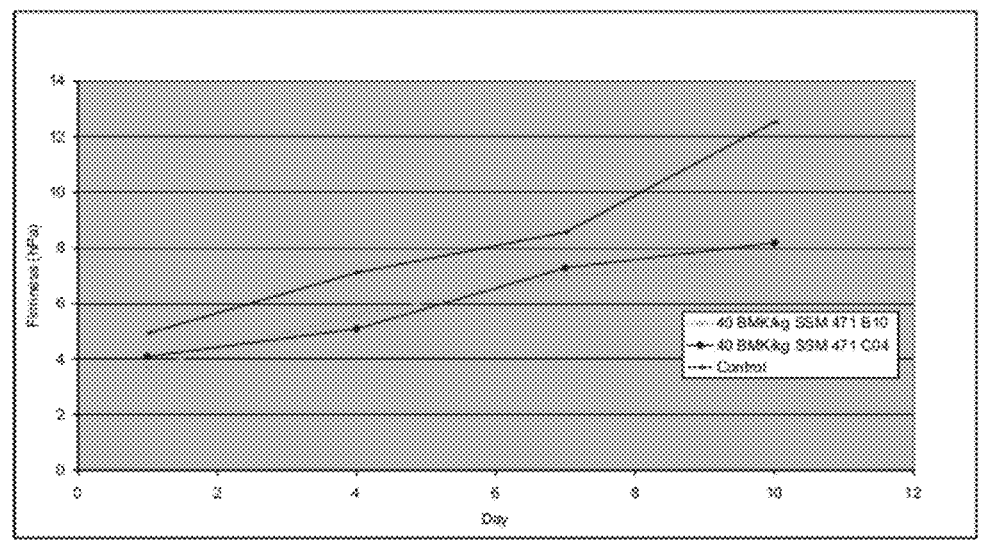
FIG. 11. Firmness test of US toast prepared with SSM 471 B10 (SEQ ID NO: 27) and SSM 471 C04 (SEQ ID NO: 29).
Figure 12:
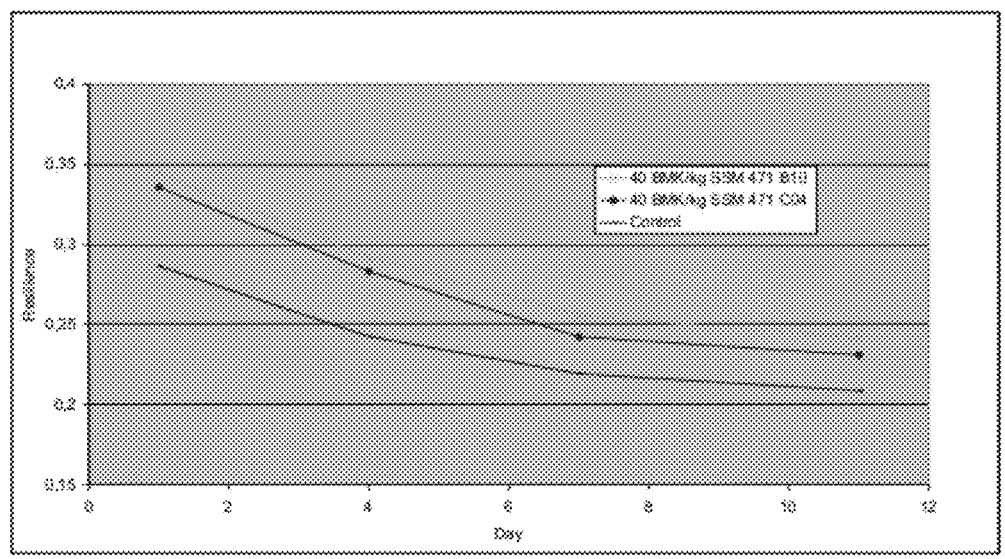
FIG. 12. Resilience test of US toast prepared with SSM 471 B10 (SEQ ID NO: 27) and SSM 471 C04 (SEQ ID NO: 29).

FIG. 11 shows the results of a firmness test of US toast prepared with SSM 471 B10 (SEQ ID NO: 27) and SSM 471 C04 (SEQ ID NO: 29). FIG. 12 shows the results of a resilience test of US toast prepared with SSM 471 B10 (SEQ ID NO: 27) and SSM 471 C04 (SEQ ID NO: 29).

Both variants are seen to give a significant decrease in firmness (FIG. 11) and a significant increase in resilience (FIG. 12) indicating that 307R and 307K variants give significant antistaling effects.

Example 36

Baking trial with PMS 370 (SEQ ID NO: 31, 307H) and SSM 471 C04 (SEQ ID NO: 29, 307K)

PMS 370 is generated using Multi Site Directed Mutagenesis as described above in Example 3. The sequence of PMS 370 is set out as SEQ ID NO: 31.

US toast is prepared by a sponge and dough procedure as described in Example 10. The toast is used to test the variants PMS 370 with 307H and SSM 471 C04 with 307K at 20, 40 and 60 BMK/kg dosage.

The toast is evaluated for resilience as described in Examples 12 and 14.

Figure 13:
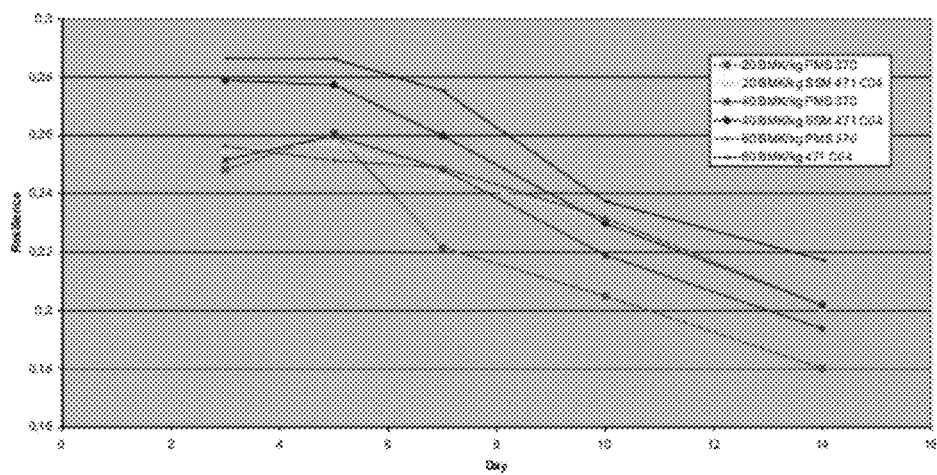
FIG. 13. Resilience test of US toast prepared with pMS 370 (SEQ ID NO: 31) and SSM 471 C04 (SEQ ID NO: 29).

FIG. 13 shows the results of a resilience test of US toast prepared with pMS 370 (SEQ ID NO: 31) and SSM 471 C04 (SEQ ID NO: 29).

Both variants are shown to give a significant increase in resilience (FIG. 13) with increasing dosage indicating that 307H and 307K variants give significantly improved resilience as a function of dosage. However, the effect of the 307K variant dosages is substantially stronger than the effect of the respective 307H variant dosages.

* * *

The invention will now be further described by the following numbered paragraphs:

1. A PS4 variant polypeptide derivable from a parent polypeptide having amylase activity, in which the PS4 variant polypeptide comprises an amino acid substitution at position 307 to lysine (K) or arginine (R), with reference to the position numbering of a *Pseudomonas saccharophilia* exoamylase sequence shown as SEQ ID NO: 1.
2. A PS4 variant polypeptide according to Paragraph 1, which is derivable from a parent polypeptide having exoamylase activity, preferably non-maltogenic exoamylase activity.
3. A PS4 variant polypeptide according to Paragraph 1, in which the amino acid substitution at position 307 is a substitution to lysine (307K), preferably H307K or a substitution to arginine (307R), preferably H307R.
4. A PS4 variant polypeptide according to Paragraph 1, 2 or 3, which further comprises an amino acid substitution at position 70.
5. A PS4 variant polypeptide according to any preceding paragraph, in which the amino acid substitution at position 70 is a substitution to aspartic acid (70D), preferably G70D.
6. A PS4 variant polypeptide according to any preceding paragraph, in which the amino acid at position 272 of the sequence of the PS4 variant polypeptide is histidine (H).
7. A PS4 variant polypeptide according to any preceding paragraph, in which the amino acid at position 303 of the sequence of the PS4 variant polypeptide is glycine (G).
8. A PS4 variant polypeptide according to any preceding paragraph, in which the PS4 variant polypeptide further comprises one or more mutations selected from the group consisting of positions: 33, 34, 121, 134, 141, 146, 157, 161, 178, 179, 223, 229, 309 or
9. A PS4 variant polypeptide according to any preceding paragraph, in which the further mutation(s) in the PS4 variant polypeptide are selected from the group consisting of: 33Y, 34N, 121F, 134R, 141P, 146G, 157L, 161A, 178F, 179T, 223E, 229P, 309P, 334P, preferably N33Y, D34N, G121F, G134R, A141P, Y146G, I157L, S161A, L178F, A179T, G223E, S229P, A309P and S334P.
10. A PS4 variant polypeptide according to any preceding paragraph, in which the PS4 variant polypeptide comprises the following substitutions 33Y, 34N, 70D, 121F, 134R, 141P, 146G, 157L, 161A, 178F, 179T, 223E, 229P, 307K, 309P, 334P, preferably N33Y, D34N, G70D, G121F, G134R, A141P, Y146G, I157L, S161A, L178F, A179T, G223E, S229P, H307K, A309P, S334P relative to a *Pseudomonas saccharophilia* exoamylase sequence shown as SEQ ID NO: 1.
11. A PS4 variant polypeptide according to any preceding paragraph, in which the PS4 variant polypeptide comprises a sequence SEQ ID NO: 21 (pSac-pMS382).
12. A PS4 variant polypeptide according to any preceding paragraph, in which the PS4 variant polypeptide comprises the following substitutions 33Y, 34N, 70D, 121F, 134R, 141P, 146G, 157L, 161A, 178F, 179T, 223E, 229P, 307R, 309P, 334P, preferably N33Y, D34N, G70D, G121F, G134R, A141P, Y146G, I157L, S161A, L178F, A179T, G223E, S229P, H307R, A309P, S334P relative to a *Pseudomonas saccharophilia* exoamylase sequence shown as SEQ ID NO: 1.
13. A PS4 variant polypeptide according to any preceding paragraph, in which the PS4 variant polypeptide comprises a sequence SEQ ID NO: 23 (pSac-pMS382R).
14. A PS4 variant polypeptide derivable from a parent polypeptide having non-maltogenic exoamylase activity, in which the PS4 variant polypeptide comprises the following substitutions 33Y, 34N, 70D, 121F, 134R, 141P, 146G, 157L, 161A, 178F, 179T, 223E, 229P, 309P, 334P, preferably N33Y, D34N, G70D, G121F, G134R, A141P, Y146G, I157L, S161A, L178F, A179T, G223E, S229P, A309P, S334P relative to a *Pseudomonas saccharophilia* exoamylase sequence shown as SEQ ID NO: 1.

15. A PS4 variant polypeptide according to any preceding paragraph, in which the PS4 variant polypeptide comprises a sequence SEQ ID NO: 25 (pSac-pMS382H).

16. A PS4 variant polypeptide according to any preceding paragraph, in which the parent polypeptide comprises a non-maltogenic exoamylase, preferably a glucan 1,4-alpha-maltotetrahydrolase (EC 3.2.1.60).

17. A PS4 variant polypeptide according to any preceding paragraph, in which the parent polypeptide is or is derivable from *Pseudomonas* species, preferably *Pseudomonas saccharophilia* or *Pseudomonas stutzeri*.

18. A PS4 variant polypeptide according to any preceding paragraph, in which the parent polypeptide is a non-maltogenic exoamylase from *Pseudomonas saccharophilia* exoamylase having a sequence shown as SEQ ID NO: 1 or SEQ ID NO: 5.

19. A PS4 variant polypeptide according to any preceding paragraph having an amino acid sequence which at least 75% identical to SEQ ID NO: 1 or SEQ ID NO: 5.

20. A PS4 variant polypeptide according to any of Paragraphs 1 to 8, in which the parent polypeptide is a non-maltogenic exoamylase from *Pseudomonas stutzeri* having a sequence shown as SEQ ID NO: 7 or SEQ ID NO: 11.

21. A PS4 variant polypeptide according to according to any of Paragraphs 1 to 8 or 11 having an amino acid sequence which at least 75% identical to SEQ ID NO: 7 or SEQ ID NO: 11.

22. A PS4 variant polypeptide according to any preceding paragraph, which comprises a sequence as set out in the description, paragraphs or figures.

23. A PS4 variant polypeptide according to any preceding paragraph, which comprises a sequence selected from the group consisting of: SEQ ID NO: 21 (pSac-pMS382), SEQ ID NO: 23 (pSac-pMS382R) and SEQ ID NO: 25 (pSac-pMS382H).

24. A PS4 variant polypeptide according to any preceding paragraph, in which the PS4 variant polypeptide has a higher thermostability compared to the parent polypeptide or a wild type polypeptide when tested under the same conditions.

25. A PS4 variant polypeptide according to any preceding paragraph, in which the half life (t½), preferably at 60 degrees C., is increased by 15% or more, preferably 50% or more, most preferably 100% or more, relative to the parent polypeptide or the wild type polypeptide.

26. A PS4 variant polypeptide according to any preceding paragraph, in which a food product treated with a the PS4 variant polypeptide has any one or more, preferably all of the following properties: (a) lower firmness; (b) higher resilience; (c) higher cohesiveness; (d) lower crumbliness; and (e) higher foldability compared to a food product which has been treated with a parent polypeptide or a wild type polypeptide.

27. A PS4 variant polypeptide according to Paragraph 26, in which the resilience, cohesiveness or foldability of the food product is independently increased by 15% or more, preferably 50% or more, most preferably 100% or more, relative to a food product which has been treated with a parent polypeptide or a wild type polypeptide.

28. A PS4 variant polypeptide according to Paragraph 26 or 27, in which each of resilience cohesiveness and foldability of a food product treated with a the PS4 variant polypeptide is increased compared to a food product which has been treated with a parent polypeptide or a wild type polypeptide.

29. A PS4 variant polypeptide according to Paragraph 26, in which the firmness or the crumbliness of the food product is independently decreased by 15% or more, preferably 50% or more, most preferably 100% or more, relative to a food product which has been treated with a parent polypeptide or a wild type polypeptide.

30. A PS4 variant polypeptide according to Paragraph 26 or 29, in which each of the firmness and crumblines of a food product treated with a the PS4 variant polypeptide is decreased compared to a food product which has been treated with a parent polypeptide or a wild type polypeptide.

31. A polypeptide comprising a fragment of at least 20 residues of a PS4 variant polypeptide according to any preceding paragraph, in which the polypeptide has non-maltogenic exoamylase activity.

32. A polypeptide derivable from a PS4 variant polypeptide according to any preceding paragraph by mutation at one or more residues of the PS4 variant polypeptide sequence, in which the polypeptide has a higher thermostability or a higher exo-specificity, or both, compared to the parent polypeptide of the PS4 variant polypeptide or a wild type polypeptide, or in which a food product treated with a the PS4 variant polypeptide has any one or more, preferably all of the following properties: (a) lower firmness; (b) higher resilience; (c) higher cohesiveness; (d) lower crumbliness; or (e) higher foldability as compared to a food product which has been treated with a parent polypeptide or a wild type polypeptide.

33 Use of a PS4 variant polypeptide as set out in any preceding paragraph as a food or feed additive.

34. A process for treating a starch comprising contacting the starch with a polypeptide as set out in any of Paragraphs 1 to 32 and allowing the polypeptide to generate from the starch one or more linear products.

35. Use of a polypeptide as set out in any of Paragraphs 1 to 32 in preparing a food or feed product.

36. A process of preparing a food or feed product comprising admixing a polypeptide as set out in any of Paragraphs 1 to 32 with a food or feed ingredient.

37. Use according to Paragraph 35, or a process according to Paragraph 36, in which the food product comprises a dough or a dough product, preferably a processed dough product.

38. A use or process according to any of Paragraphs 35 to 37, in which the food product is a bakery product.

39. A process for making a bakery product comprising: (a) providing a starch medium; (b) adding to the starch medium a polypeptide as set out in any of Paragraphs 1 to 32; and (c) applying heat to the starch medium during or after step (b) to produce a bakery product.

40. A food product, feed product, dough product or a bakery product obtained by a process according to any of Paragraphs 35 to 39.

41. An improver composition for a dough, in which the improver composition comprises a polypeptide as set out in any of Paragraphs 1 to 32, and at least one further dough ingredient or dough additive.

42. A composition comprising a flour and a polypeptide as set out in any of Paragraphs 1 to 32.

43. Use of a PS4 variant polypeptide as set out in any of Paragraphs 1 to 42, in a dough product to retard or reduce staling, preferably detrimental retrogradation, of the dough product.

44. Use of a PS4 variant polypeptide as set out in any of Paragraphs 1 to 42, in a dough product to improve any one or more of firmness, resilience, cohesiveness, crumbliness or foldability of the dough product.

45. A combination of a PS4 variant polypeptide as set out in any preceding paragraph, together with any one or more of the following:
    (a) maltogenic alpha-amylase also called glucan 1,4-α-maltohydrolase (EC 3.2.1.133) from *Bacillus stearothermophilus*, or a variant, homologue, or mutants thereof which have maltogenic alpha-amylase activity;
    (b) a bakery xylanase (EC 3.2.1.8) from e.g. *Bacillus* sp., *Aspergillus* sp., *Thermomyces* sp. or *Trichoderma* sp.;
    (c) α-amylase (EC 3.2.1.1) from *Bacillus* amyloliquafaciens or a variant, homologue, or mutants thereof which have alpha-amylase activity; and
    (d) a lipase such as glycolipase from *Fusarium heterosporum*.

46. Use of a combination according to Paragraph 45 for an application according to any preceding paragraph.

47. A food or feed product produced by treatment with a combination according to Paragraph 31.

48. A nucleic acid capable of encoding a polypeptide according to any of Paragraphs 1 to 32.

49. A nucleic acid according to Paragraph 48 having a nucleic acid sequence which at least 75% identical to SEQ ID NO: 6 or SEQ ID NO: 12.

50. A nucleic acid comprising a fragment of at least 60 residues of a nucleic acid according to Paragraph 48 or 49 which is capable of encoding a polypeptide having non-maltogenic exoamylase activity.

51. A nucleic acid sequence derivable from a parent sequence, the parent sequence capable of encoding a non-maltogenic exoamylase, which nucleic acid sequence comprises a substitution at one or more residues such that the nucleic acid encodes a lysine (R) or arginine (K) residue at position 307, optionally together with one or more further mutation(s) such that the nucleic acid encodes one or more residues selected from the group consisting of: 33Y, 34N, 121F, 134R,141P, 146G, 157L, 161A, 178F, 179T, 223E, 229P, 309P, 334P with reference to the position numbering of a *Pseudomonas saccharophilia* exoamylase sequence shown as SEQ ID NO: 1.

52. A PS4 nucleic acid sequence according to any of Paragraphs 48 to 52, which is derived from a parent sequence encoding a non-maltogenic exoamylase by substitution of one or more nucleotide residues.

53. A nucleic acid sequence according to any of Paragraphs 48 to 52, selected from the group consisting of: SEQ ID NO: 22 (pSac-pMS382), SEQ ID NO: 24 (pSac-pMS382R) and SEQ ID NO: 26 (pSac-pMS382H).

54. A plasmid comprising a PS4 nucleic acid according to any of Paragraphs 48 to 53.

55. An expression vector comprising a PS4 nucleic acid according to any of Paragraphs 48 to 54, or capable of expressing a polypeptide according to any of Paragraphs 1 to 32.

56. A host cell comprising, preferably transformed with, a plasmid according to Paragraph 54 or an expression vector according to Paragraph 55.

57. A cell capable of expressing a polypeptide according to any of Paragraphs 1 to 32.

58. A host cell according to Paragraph 56, or a cell according to Paragraph 57, which is a bacterial, fungal or yeast cell.

59. A method of expressing a PS4 variant polypeptide, the method comprising obtaining a host cell or a cell according to Paragraph 56, 57 or 58 and expressing the polypeptide from the cell or host cell, and optionally purifying the polypeptide.

60. A method of altering the sequence of a polypeptide, preferably a non-maltogenic exoamylase, by introducing an amino acid substitution at position 70 to a basic or positively charged residue, optionally together with one or more further mutation(s) selected from the group consisting of: 33Y, 34N, 121F, 134R,141P, 146G, 157L, 161A, 178F, 179T, 223E, 229P, 272H, 303G, 309P, 334P (with reference to the position numbering of a *Pseudomonas saccharophilia* exoamylase sequence shown as SEQ ID NO: 1), into a parent polypeptide having non-maltogenic exoamylase activity.

61. A method according to Paragraph 60, in which the basic or positively charged residue comprises lysine (K), arginine (R) or histidine (H).

62. A method according to Paragraph 60 or 61, in which the sequence of the non-maltogenic exoamylase is altered by altering the sequence of a nucleic acid which encodes the non-maltogenic exoamylase.

63. A method of producing a PS4 polypeptide variant, the method comprising introducing an amino acid substitution into a parent polypeptide having non-maltogenic exoamylase activity, the amino acid substitution being selected from the group consisting of: 33Y, 34N, 70K/R/H, 121F, 134R,141P, 146G, 157L, 161A, 178F, 179T, 223E, 229P, 272H, 303G, 309P, 334P with reference to the position numbering of a *Pseudomonas saccharophilia* exoamylase sequence shown as SEQ ID NO: 1.

64. A method according to Paragraph 62 or 63, in which the sequence of a nucleic acid encoding the parent polypeptide is altered to introduce the amino acid substitution.

65. A method of altering the sequence of a nucleic acid encoding a non-maltogenic exoamylase, the method comprising introducing into the sequence a codon which encodes an amino acid residue selected from the group consisting of: 33Y, 34N, 70K/R/H, 121F, 134R,141P, 146G, 157L, 161A, 178F, 179T, 223E, 229P, 272H, 303G, 309P, 334P, with reference to the position numbering of a *Pseudomonas saccharophilia* exoamylase sequence shown as SEQ ID NO: 1.

66. A method of increasing the thermostability, or the exo-specificity, or both, of a polypeptide, the method comprising the steps as set out in any of Paragraphs 58 to 65.

67. A method according to any of Paragraphs 58 to 66, in which the polypeptide is isolated or purified, or both.

68. A polypeptide obtainable by a method according to any of Paragraphs 58 to 67.

69. A polypeptide obtained by a method according to any of Paragraphs 58 to 68.

70. A PS4 variant polypeptide, use, process, food product, feed product, dough product, bakery product, improver composition, composition, nucleic acid, vector or host cell substantially as hereinbefore described with reference to and as shown in the accompanying drawings.

References

Penning a, D., van der Veen, B.A., Knegtel, R.M., van Hijum, S.A., Rozeboom, H.J., Kalk, K.H., Dijkstra, B.W., Dijkhuizen, L. (1996). The raw starch binding domain of cyclodextrin glycosyltransferase from *Bacillus circulans* strain 251. J. Biol. Chem. 271, 32777-32784.

Sambrook J, F.E.M.T. (1989). Molecular Cloning: A Laboratory Manual, 2nd Edn. Cold Spring Harbor Laboratory, Cold Spring Harbor N.Y.

Zhou, J.H., Baba, T., Takano, T., Kobayashi, S., Arai, Y. (1989). Nucleotide sequence of the maltotetraohydrolase gene from *Pseudomonas saccharophila*. FEBS Lett. 255, 37-41.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A non-naturally occurring variant polypeptide of SEQ ID NO: 1 having amylase activity and comprising an amino acid substitution at position 307 to lysine (K) or arginine (R), with reference to the position numbering of SEQ ID NO: 1.

2. The polypeptide according to claim 1, wherein the polypeptide is prepared from a parent polypeptide having exoamylase activity.

3. A method of treating a food product with the polypeptide of claim 1 comprising contacting the food product with the polypeptide.

4. A process for treating a starch comprising contacting the starch with a polypeptide as set out in claim 1 and allowing the polypeptide to generate from the starch one or more linear products.

5. A process of preparing a food or feed product comprising admixing a polypeptide as set out in claim 1 with a food or feed ingredient.

6. A process according to claim 5, in which the food product comprises a dough or a dough product, preferably a processed dough product, or in which the food product is a bakery product.

7. A process for making a bakery product comprising: (a) providing a starch medium; (b) adding to the starch medium a polypeptide as set out in claim 1; and (c) applying heat to the starch medium during or after step (b) to produce a bakery product.

8. A food product or feed product comprising the polypeptide as set out in claim 1 with a food or feed ingredient.

9. An improver composition for a dough, in which the improver composition comprises the polypeptide as set out in claim 1, and at least one further dough ingredient or dough additive.

10. A composition comprising a flour and the polypeptide as set out in claim 1.

11. A combination of the polypeptide as set out in claim 1, together with any one or more of the following:
(a) maltogenic alpha-amylase also called glucan 1,4-a-maltohydrolase (EC 3.2.1.133) from *Bacillus stearothermophilus*, or a variant, homologue, or mutants thereof which have maltogenic alpha-amylase activity;
(b) a bakery xylanase (EC 3.2.1.8) from e.g. *Bacillus* sp., *Aspergillus* sp., *Thermomyces* sp. or *Trichoderma* sp.;
(c) a-amylase (EC 3.2.1.1) from *Bacillus amyloliqufaciens* or a variant, homologue, or mutants thereof which have alpha-amylase activity; and
(d) a lipase such as glycolipase from *Fusarium heterosporum*.

12. A food or feed product produced by treatment with a combination of the polypeptide according to claim 1 and the enzyme(s) according to claim 11.

13. The polypeptide according to claim 2, wherein the parent polypeptide has nonmaltogenic exoamylase activity.

14. The polypeptide according to claim 1, wherein the amino acid substitution is H307K.

15. The polypeptide according to claim 1, wherein the amino acid substitution is H307R.

16. The polypeptide according to claim 1, wherein the polypeptide further comprises an amino acid substitution at position 70 with reference to the position numbering of SEQ ID NO: 1.

17. The polypeptide according to claim 16, wherein the amino acid substitution is G70D.

18. The polypeptide according to claim 17, wherein the polypeptide comprises H307K, a histidine (H) at position 272, and a glycine (G) at position 303, with reference to the position numbering of SEQ ID NO: 1.

19. The polypeptide according to claim 17, wherein the polypeptide comprises H307R, a glycine (G) at position 303, and a histidine (H) at position 272, with reference to the position numbering of SEQ ID NO: 1.

20. The polypeptide according to claim 1, wherein the polypeptide further comprises one or more mutation(s) selected from the group consisting of positions: 33, 34, 70, 121, 134, 141, 146, 157, 161, 178, 179, 223, 229, 309 or 334, with reference to the position numbering of SEQ ID NO: 1.

21. The polypeptide according to claim 20, wherein the one or more mutation(s) are selected from the group consisting of: N:33Y, D34N, G121F, G134R, A141P, Y146G, I157L, S161A, L178F, A179T, G223E, S229P, A309P and S334P.

22. The polypeptide according to claim 1 comprising SEQ ID NO: 21.

23. The polypeptide according to claim 1 comprising SEQ ID NO: 23.

24. The polypeptide according to claim 2, wherein the parent polypeptide is a non-maltogenic exoamylase.

25. The polypeptide according to claim 24, wherein the parent polypeptide is a glucan 1,4-alpha-maltotetrahydrolase (EC 3.2.1.60).

26. The polypeptide according to claim 2, wherein the parent polypeptide is a *Pseudomonas saccharophila* exoamylase.

27. The polypeptide according to claim 2, wherein the parent polypeptide is a non-maltogenic exoamylase from *Pseudomonas saccharophila* having a sequence shown as SEQ ID NO: 1.

28. The polypeptide according to claim 1, wherein the polypeptide has a higher thermostability compared to a parent polypeptide from which it is prepared when tested under the same conditions.

29. The polypeptide according to claim 1, wherein the polypeptide has a half life (t½) at 60 degrees C. increased by 15% or more compared to a parent polypeptide from which it is prepared when tested under the same conditions.

30. A method according to claim 3, wherein the food product is a tortilla.

31. A process according to claim 5, wherein the food product is a tortilla.

32. A process according to claim 6, wherein the bakery product is a tortilla.

33. A process according to claim 7, wherein the bakery product is a tortilla.

34. A food product according to claim 8, wherein the food product is a tortilla.

* * * * *

SEQUENCE LISTING

<160> NUMBER OF SEQ ID NOS: 82

<210> SEQ ID NO 1
<211> LENGTH: 530
<212> TYPE: PRT
<213> ORGANISM: Pseudomonas saccharophila

<400> SEQUENCE: 1

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270
```

```
Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
        515                 520                 525

Ser Phe
    530

<210> SEQ ID NO 2
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95
```

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
            115                 120                 125

Leu Pro Ala Gly Gln Arg Phe Trp Arg Asn Asp Cys Pro Asp Pro Gly
        130                 135                 140

Asn Tyr Pro Asn Asp Cys Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 3
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

```
Tyr Asn Trp Tyr Asn Ile Leu Arg Gln Gln Ala Ser Thr Ile Ala Ala
             35                  40                  45

Asp Gly Phe Ser Ala Ile Trp Met Pro Val Pro Trp Arg Asp Phe Ser
 50                  55                  60

Ser Trp Thr Asp Pro Gly Arg Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
                100                 105                 110

Val Val Pro Asn His Met Asn Arg Asp Tyr Pro Asp Lys Glu Ile Asn
                115                 120                 125

Leu Pro Ala Gly Gln Arg Phe Trp Arg Asn Asp Cys Pro Asp Pro Gly
            130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Phe Arg Phe
            180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ala Pro
210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 4
<211> LENGTH: 429
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 4
```

| | | | | | | | | | | | | | | | |
|---|---|---|---|---|---|---|---|---|---|---|---|---|---|---|---|
| Asp | Gln | Ala | Gly | Lys | Ser | Pro | Ala | Gly | Val | Arg | Tyr | His | Gly | Gly | Asp |
| 1 | | | | 5 | | | | | 10 | | | | | 15 | |
| Glu | Ile | Ile | Leu | Gln | Gly | Phe | His | Trp | Asn | Val | Val | Arg | Glu | Ala | Pro |
| | | | 20 | | | | | 25 | | | | | 30 | | |
| Tyr | Asn | Trp | Tyr | Asn | Ile | Leu | Arg | Gln | Gln | Ala | Ser | Thr | Ile | Ala | Ala |
| | | | 35 | | | | | 40 | | | | | 45 | | |
| Asp | Gly | Phe | Ser | Ala | Ile | Trp | Met | Pro | Val | Pro | Trp | Arg | Asp | Phe | Ser |
| 50 | | | | | 55 | | | | | 60 | | | | | |
| Ser | Trp | Thr | Asp | Pro | Gly | Arg | Ser | Gly | Gly | Glu | Gly | Tyr | Phe | Trp |
| 65 | | | | | 70 | | | | | 75 | | | | | 80 |
| His | Asp | Phe | Asn | Lys | Asn | Ser | Arg | Tyr | Gly | Ser | Asp | Ala | Gln | Leu | Arg |
| | | | | 85 | | | | | 90 | | | | | 95 | |
| Gln | Ala | Ala | Gly | Ala | Leu | Gly | Gly | Ala | Gly | Val | Lys | Val | Leu | Tyr | Asp |
| | | | | 100 | | | | | 105 | | | | | 110 | |
| Val | Val | Pro | Asn | His | Met | Asn | Arg | Asp | Tyr | Pro | Asp | Lys | Glu | Ile | Asn |
| | | | 115 | | | | | 120 | | | | | 125 | | |
| Leu | Pro | Ala | Gly | Gln | Arg | Phe | Trp | Arg | Asn | Asp | Cys | Pro | Asp | Pro | Gly |
| 130 | | | | | 135 | | | | | 140 | | | | | |
| Asn | Tyr | Pro | Asn | Asp | Cys | Asp | Asp | Gly | Asp | Arg | Phe | Leu | Gly | Gly | Glu |
| 145 | | | | | 150 | | | | | 155 | | | | | 160 |
| Ser | Asp | Leu | Asn | Thr | Gly | His | Pro | Gln | Ile | Tyr | Gly | Met | Phe | Arg | Asp |
| | | | | 165 | | | | | 170 | | | | | 175 | |
| Glu | Phe | Thr | Asn | Leu | Arg | Ser | Gly | Tyr | Gly | Ala | Gly | Gly | Phe | Arg | Phe |
| | | | 180 | | | | | 185 | | | | | 190 | | |
| Asp | Phe | Val | Arg | Gly | Tyr | Ala | Pro | Glu | Arg | Val | Asp | Ser | Trp | Met | Ser |
| | | | 195 | | | | | 200 | | | | | 205 | | |
| Asp | Ser | Ala | Asp | Ser | Ser | Phe | Cys | Val | Gly | Glu | Leu | Trp | Lys | Ala | Pro |
| 210 | | | | | 215 | | | | | 220 | | | | | |
| Ser | Glu | Tyr | Pro | Ser | Trp | Asp | Trp | Arg | Asn | Thr | Ala | Ser | Trp | Gln | Gln |
| 225 | | | | | 230 | | | | | 235 | | | | | 240 |
| Ile | Ile | Lys | Asp | Trp | Ser | Asp | Arg | Ala | Lys | Cys | Pro | Val | Phe | Asp | Phe |
| | | | | 245 | | | | | 250 | | | | | 255 | |
| Ala | Leu | Lys | Glu | Arg | Met | Gln | Asn | Gly | Ser | Val | Ala | Asp | Trp | Lys | His |
| | | | 260 | | | | | 265 | | | | | 270 | | |
| Gly | Leu | Asn | Gly | Asn | Pro | Asp | Pro | Arg | Trp | Arg | Glu | Val | Ala | Val | Thr |
| | | | 275 | | | | | 280 | | | | | 285 | | |
| Phe | Val | Asp | Asn | His | Asp | Thr | Gly | Tyr | Ser | Pro | Gly | Gln | Asn | Gly | Gly |
| | 290 | | | | | 295 | | | | | 300 | | | | |
| Gln | His | Leu | Trp | Ala | Leu | Gln | Asp | Gly | Leu | Ile | Arg | Gln | Ala | Tyr | Ala |
| 305 | | | | | 310 | | | | | 315 | | | | | 320 |
| Tyr | Ile | Leu | Thr | Ser | Pro | Gly | Thr | Pro | Val | Val | Tyr | Trp | Pro | His | Met |
| | | | | 325 | | | | | 330 | | | | | 335 | |
| Tyr | Asp | Trp | Gly | Tyr | Gly | Glu | Phe | Ile | Arg | Gln | Leu | Ile | Gln | Val | Arg |
| | | | 340 | | | | | 345 | | | | | 350 | | |
| Arg | Thr | Ala | Gly | Val | Arg | Ala | Asp | Ser | Ala | Ile | Ser | Phe | His | Ser | Gly |
| | | | 355 | | | | | 360 | | | | | 365 | | |
| Tyr | Ser | Gly | Leu | Val | Ala | Thr | Val | Ser | Gly | Ser | Gln | Gln | Thr | Leu | Val |
| | 370 | | | | | 375 | | | | | 380 | | | | |
| Val | Ala | Leu | Asn | Ser | Asp | Leu | Ala | Asn | Pro | Gly | Gln | Val | Ala | Ser | Gly |

```
                385                 390                 395                 400
Ser Phe Ser Glu Ala Val Asn Ala Ser Asn Gly Gln Val Arg Val Trp
                    405                 410                 415

Arg Ser Gly Ser Gly Asp Gly Gly Asn Asp Gly Gly
                420                 425

<210> SEQ ID NO 5
<211> LENGTH: 551
<212> TYPE: PRT
<213> ORGANISM: Pseudomonas saccharophila

<400> SEQUENCE: 5

Met Ser His Ile Leu Arg Ala Ala Val Leu Ala Ala Val Leu Leu Pro
1               5                   10                  15

Phe Pro Ala Leu Ala Asp Gln Ala Gly Lys Ser Pro Ala Gly Val Arg
                20                  25                  30

Tyr His Gly Gly Asp Glu Ile Ile Leu Gln Gly Phe His Trp Asn Val
            35                  40                  45

Val Arg Glu Ala Pro Asn Asp Trp Tyr Asn Ile Leu Arg Gln Gln Ala
        50                  55                  60

Ser Thr Ile Ala Ala Asp Gly Phe Ser Ala Ile Trp Met Pro Val Pro
65                  70                  75                  80

Trp Arg Asp Phe Ser Ser Trp Thr Asp Gly Gly Lys Ser Gly Gly Gly
                85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Gly Ala Leu Gly Gly Ala Gly Val
        115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Glu Ser Asp Leu Asn Thr Gly His Pro Gln Ile Tyr
            180                 185                 190

Gly Met Phe Arg Asp Glu Leu Ala Asn Leu Arg Ser Gly Tyr Gly Ala
        195                 200                 205

Gly Gly Phe Arg Phe Asp Phe Val Arg Gly Tyr Ala Pro Glu Arg Val
    210                 215                 220

Asp Ser Trp Met Ser Asp Ser Ala Asp Ser Ser Phe Cys Val Gly Glu
225                 230                 235                 240

Leu Trp Lys Gly Pro Ser Glu Tyr Pro Ser Trp Asp Trp Arg Asn Thr
                245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Val
        275                 280                 285

Ala Asp Trp Lys His Gly Leu Asn Gly Asn Pro Asp Pro Arg Trp Arg
    290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
```

```
                340             345             350
Tyr Trp Ser His Met Tyr Asp Trp Gly Tyr Gly Asp Phe Ile Arg Gln
        355                 360                 365

Leu Ile Gln Val Arg Arg Thr Ala Gly Val Arg Ala Asp Ser Ala Ile
    370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Ala Asn Pro Gly
                405                 410                 415

Gln Val Ala Ser Gly Ser Phe Ser Glu Ala Val Asn Ala Ser Asn Gly
            420                 425                 430

Gln Val Arg Val Trp Arg Ser Gly Ser Asp Gly Gly Gly Asn Asp
        435                 440                 445

Gly Gly Glu Gly Gly Leu Val Asn Val Asn Phe Arg Cys Asp Asn Gly
        450                 455                 460

Val Thr Gln Met Gly Asp Ser Val Tyr Ala Val Gly Asn Val Ser Gln
465                 470                 475                 480

Leu Gly Asn Trp Ser Pro Ala Ser Ala Val Arg Leu Thr Asp Thr Ser
                485                 490                 495

Ser Tyr Pro Thr Trp Lys Gly Ser Ile Ala Leu Pro Asp Gly Gln Asn
            500                 505                 510

Val Glu Trp Lys Cys Leu Ile Arg Asn Glu Ala Asp Ala Thr Leu Val
        515                 520                 525

Arg Gln Trp Gln Ser Gly Gly Asn Asn Gln Val Gln Ala Ala Ala Gly
        530                 535                 540

Ala Ser Thr Ser Gly Ser Phe
545                 550

<210> SEQ ID NO 6
<211> LENGTH: 3050
<212> TYPE: DNA
<213> ORGANISM: Pseudomonas saccharophila

<400> SEQUENCE: 6
gatcggcgta ggtttcgcat tcgttgccca ggcgatattt cgccggtgcg ccagcagcct      60
ggaagcaggc ctggtcgccg ccgccggccg tggcgccgac gcccgaacgc agatagccgt     120
ggaaatcgac cgccagggcc gggccgccga ccagcagggc ggcaagcagg caggcgggtt     180
ttaggacgaa caggggggtgc gcggtgtgct tcatgacgag gtccttgttt ttcttgttaa     240
tgccgaatcg atcacgcctt cgctgcgtgt cgcagggcgc agctcggtgg cgaaagcctc     300
ggggatggct ccgctggcgg catcctcccg accagagatt tcgctggcgc agctcgaggg     360
cgtaatcagg atgagtgcgg cgtaatccct ggggtggggc tacgcccggc agggcgcaga     420
tgattgccag gggccttcgg cctggccact acgccgcctg caactgggcg gggaggttg     480 gtggtcgggg cgtgcagggg cagcctgcgg gtgccggtcg aagacccggc cggcgttcat     540
cctcgtccgg cggccttgcc gtaggatacc cgaacaagca caagaaccgg agtattgcga     600
tgagccacat cctgcgtgcc gccgtattgg cggcggtcct gctgccgttt ccgcactgg     660 ccgatcaggc cggcaagagc ccggccgggg tgcgctacca cggcggcgac gaaatcatcc     720
tccagggctt ccactggaac gtcgtccgcg aagcgcccaa cgactggtac aacatcctcc     780
gccaacaggc ctcgacgatc gcggccgacg gcttctcggc aatctggatg ccggtgccct     840
ggcgtgactt ctccagctgg accgacgcg gcaagtccgg cggcggcgaa ggctacttct     900
ggcacgactt caacaagaac ggccgctacg gcagcgacgc ccagctgcgc caggccgccg     960
```

```
gcgcactcgg tggcgccggg gtgaaggtgc tctacgatgt ggtgcccaat cacatgaacc    1020
gcggctaccc ggacaaggag atcaacctgc cggccggcca gggcttctgg cgcaacgact    1080
gcgccgaccc gggcaactac cccaacgact gcgacgacgg tgaccgcttc atcggcggcg    1140
agtcggacct gaacaccggc catccgcaga tttacggcat gtttcgcgac gagcttgcca    1200
acctgcgcag cggctacggc gccggcggct ccgcttcga cttcgttcgc ggctatgcgc    1260
ccgagcgggt cgacagctgg atgagcgaca cgccgacag cagcttctgc gttggcgagc    1320
tgtggaaagg cccttctgaa tatccgagct gggactggcg caacgcgcg agctggcagc    1380 agatcatcaa ggactggtcc gaccgggcca agtgcccggt gttcgacttc gctctcaagg    1440
agcgcatgca gaacgctcg gtcgccgact ggaagcatgg cctcaatggc aaccccgacc    1500
cgcgctggcg cgaggtggcg gtgaccttcg tcgacaacca cgacaccggc tattcgcccg    1560
ggcagaacgg cggccagcac cactgggcgc tgcaggacgg gctgatccgc caggcctacg    1620
cctacatcct caccagcccg ggcacgccgg tggtgtactg gtcgcacatg tacgactggg    1680
gctacggcga cttcatccgc cagctgatcc aggtgcggcg caccgccggc gtgcgcgccg    1740
attcggcgat cagcttccat agcggctaca gcggtctggt cgctaccgtc agcggcagcc    1800
agcagaccct ggtggtggcg ctcaactccg atctggccaa ccccggccag gttgccagcg    1860
gcagcttcag cgaggcggtc aacgccagca acggccaggt gcgcgtctgg cgcagcggta    1920
gcggcgatgg cggcgggaat gacggcggcg agggtggctt ggtcaatgtg aactttcgct    1980
gcgacaacgg cgtgacgcag atgggcgaca gcgtctacgc ggtgggcaac gtcagccagc    2040
tcggcaactg gagcccggcc tccgcggtac ggctgaccga caccagcagc tatccgacct    2100
ggaagggcag catcgccctg cctgacggtc agaacgtgga atggaagtgc ctgatccgca    2160
acgaggcgga cgcgacgctg gtgcgtcagt ggcaatcggg cggcaacaac caggtccagg    2220
ccgccgccgg cgcgagcacc agcggctcgt tctgacgaca tgcccgcccg gcctcggcta    2280
cgcctacgcc gggcggctcc tcccgaccca gggtgggcag ggaggaggcc ggcgacgggc    2340
cgggccgccg atgctggcac gacaaccata aaagccttcg cgctgcgctg tcgtatcagg    2400
agctgttcat gttggcccag acccgctcga ccccttccg gcttggcttc ctggcccggc    2460
tgtacctgct gatcgccgca ctggtggcct tgctgatgct ggtagccggc accagcctgg    2520
ttgccatcgg ccgcctgcaa ggcaatgccg agcaaatctc gtcgaccgcg tcgcgtctgc    2580
tggtcagcga gagcttcttc ggtacgttgc agagcctgac gcagaacctg tccgacgccc    2640
tggccgagga ccggcctgac cagctcgacg gctatgtcgg ccggcatcgc acgctgcagg    2700 accaggcct cgagctgttc gcccagctgg agcgggtgac gccggacat gccgagacca    2760 agcaagcctg gcggcgctgt tgccggagct cgaccgccgc agcctggcgc tgatcgatgc    2820
gcacgcgacc tgctcgcgcg tggggcgcaa cgccgtcgcc tgcgcgatct gcagctgcag    2880
ttctcgcggc tcaagcagga cctgctgcag gcgcagttcg tgacgggcga cgagctggtc    2940
gcctattcca tcaagcagtt catcatcccg ctcgagcagg tcgagcgctg ctgttcgatg    3000
ccatcggcgt gtcttcgatc aaggcactcg atgaagcggg tgcgcagatc                3050
```

<210> SEQ ID NO 7
<211> LENGTH: 527
<212> TYPE: PRT
<213> ORGANISM: Pseudomonas stutzeri

<400> SEQUENCE: 7

Asp Gln Ala Gly Lys Ser Pro Asn Ala Val Arg Tyr His Gly Gly Asp

-continued

```
  1               5                   10                  15
Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ala Thr Ile Ala Ala
             35                  40                  45

Asp Gly Phe Ser Ala Ile Trp Met Pro Val Pro Trp Arg Asp Phe Ser
 50                  55                  60

Ser Trp Ser Asp Gly Ser Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
                100                 105                 110

Val Val Pro Asn His Met Asn Arg Gly Tyr Pro Asp Lys Glu Ile Asn
             115                 120                 125

Leu Pro Ala Gly Gln Gly Phe Trp Arg Asn Asp Cys Ala Asp Pro Gly
         130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
             165                 170                 175

Glu Phe Thr Asn Leu Arg Ser Gln Tyr Gly Ala Gly Phe Arg Phe
             180                 185                 190

Asp Phe Val Arg Gly Tyr Ala Pro Glu Arg Val Asn Ser Trp Met Thr
         195                 200                 205

Asp Ser Ala Asp Asn Ser Phe Cys Val Gly Glu Leu Trp Lys Gly Pro
210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
             245                 250                 255

Ala Leu Lys Glu Arg Met Gln Asn Gly Ser Ile Ala Asp Trp Lys His
         260                 265                 270

Gly Leu Asn Gly Asn Pro Asp Pro Arg Trp Arg Glu Val Ala Val Thr
     275                 280                 285

Phe Val Asp Asn His Asp Thr Gly Tyr Ser Pro Gly Gln Asn Gly Gly
         290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
             325                 330                 335

Tyr Asp Trp Gly Tyr Gly Asp Phe Ile Arg Gln Leu Ile Gln Val Arg
         340                 345                 350

Arg Ala Ala Gly Val Arg Ala Asp Ser Ala Ile Ser Phe His Ser Gly
         355                 360                 365

Tyr Ser Gly Leu Val Ala Thr Val Ser Gly Ser Gln Gln Thr Leu Val
     370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
             405                 410                 415

Arg Ser Gly Thr Gly Ser Gly Gly Gly Glu Pro Gly Ala Leu Val Ser
             420                 425                 430
```

```
Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Trp Lys Cys Leu Ile Arg
                485                 490                 495

Asn Glu Ala Asn Ala Thr Gln Val Arg Gln Trp Gln Gly Gly Ala Asn
                500                 505                 510

Asn Ser Leu Thr Pro Ser Glu Gly Ala Thr Thr Val Gly Arg Leu
                515                 520                 525

<210> SEQ ID NO 8
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ala Thr Ile Ala Ala
            35                  40                  45

Asp Gly Phe Ser Ala Ile Trp Met Pro Val Pro Trp Arg Asp Phe Ser
        50                  55                  60

Ser Trp Ser Asp Pro Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
                100                 105                 110

Val Val Pro Asn His Met Asn Arg Asp Tyr Pro Asp Lys Glu Ile Asn
                115                 120                 125

Leu Pro Ala Gly Gln Arg Phe Trp Arg Asn Asp Cys Pro Asp Pro Gly
130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
                180                 185                 190

Asp Phe Val Arg Gly Tyr Ala Pro Glu Arg Val Asn Ser Trp Met Thr
                195                 200                 205

Asp Ser Ala Asp Asn Ser Phe Cys Val Gly Glu Leu Trp Lys Ala Pro
        210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
                260                 265                 270
```

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
        370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
        450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 9
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Arg Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ser Ala Leu Gly Gly Ala Gly Val Lys Val Leu Tyr Asp
            100                 105                 110

```
Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 10
```

```
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Arg Ser Gly Gly Gly Gly Tyr Phe Trp
65                  70                  75                  80

His Asp Phe Asn Lys Asn Ser Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380
```

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
            405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
            450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
            485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
            515                 520                 525

<210> SEQ ID NO 11
<211> LENGTH: 548
<212> TYPE: PRT
<213> ORGANISM: Pseudomonas stutzeri

<400> SEQUENCE: 11

Met Ser His Ile Leu Arg Ala Ala Val Leu Ala Ala Met Leu Leu Pro
1               5                   10                  15

Leu Pro Ser Met Ala Asp Gln Ala Gly Lys Ser Pro Asn Ala Val Arg
            20                  25                  30

Tyr His Gly Gly Asp Glu Ile Ile Leu Gln Gly Phe His Trp Asn Val
            35                  40                  45

Val Arg Glu Ala Pro Asn Asp Trp Tyr Asn Ile Leu Arg Gln Gln Ala
50                  55                  60

Ala Thr Ile Ala Ala Asp Gly Phe Ser Ala Ile Trp Met Pro Val Pro
65                  70                  75                  80

Trp Arg Asp Phe Ser Ser Trp Ser Asp Gly Ser Lys Ser Gly Gly Gly
            85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Ser Ala Leu Gly Gly Ala Gly Val
            115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
            165                 170                 175

Phe Ile Gly Gly Asp Ala Asp Leu Asn Thr Gly His Pro Gln Val Tyr
            180                 185                 190

Gly Met Phe Arg Asp Glu Phe Thr Asn Leu Arg Ser Gln Tyr Gly Ala
            195                 200                 205

Gly Gly Phe Arg Phe Asp Phe Val Arg Gly Tyr Ala Pro Glu Arg Val
            210                 215                 220

Asn Ser Trp Met Thr Asp Ser Ala Asp Asn Ser Phe Cys Val Gly Glu
225                 230                 235                 240

Leu Trp Lys Gly Pro Ser Glu Tyr Pro Asn Trp Asp Trp Arg Asn Thr
        245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Ile
        275                 280                 285

Ala Asp Trp Lys His Gly Leu Asn Gly Asn Pro Asp Pro Arg Trp Arg
    290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
        355                 360                 365

Leu Ile Gln Val Arg Arg Ala Ala Gly Val Arg Ala Asp Ser Ala Ile
    370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Gly Asn Pro Gly
                405                 410                 415

Gln Val Ala Ser Gly Ser Phe Ser Glu Ala Val Asn Ala Ser Asn Gly
            420                 425                 430

Gln Val Arg Val Trp Arg Ser Gly Thr Gly Ser Gly Gly Gly Glu Pro
        435                 440                 445

Gly Ala Leu Val Ser Val Ser Phe Arg Cys Asp Asn Gly Ala Thr Gln
    450                 455                 460

Met Gly Asp Ser Val Tyr Ala Val Gly Asn Val Ser Gln Leu Gly Asn
465                 470                 475                 480

Trp Ser Pro Ala Ala Ala Leu Arg Leu Thr Asp Thr Ser Gly Tyr Pro
                485                 490                 495

Thr Trp Lys Gly Ser Ile Ala Leu Pro Ala Gly Gln Asn Glu Glu Trp
            500                 505                 510

Lys Cys Leu Ile Arg Asn Glu Ala Asn Ala Thr Gln Val Arg Gln Trp
        515                 520                 525

Gln Gly Gly Ala Asn Asn Ser Leu Thr Pro Ser Glu Gly Ala Thr Thr
    530                 535                 540

Val Gly Arg Leu
545

<210> SEQ ID NO 12
<211> LENGTH: 2082
<212> TYPE: DNA
<213> ORGANISM: Pseudomonas stutzeri

<400> SEQUENCE: 12
gatcggcctt tacggaaagt gatagagctt ctcttccggc aaactttgtt ccccagtgac      60
agagggttag tatcggatcg cttcctcttt gggtttggta gatcaggagc gccgagagca     120
ggatgaaatc ctgcggccag aaggtcgcgc gaagatgtg gaactgctgc tggccgagat      180
ccggccggcg ttcatcctcg tccggcggcc ttgccgccag ctacccgaac aagcacaaga     240
accggagtat tgcgatgagc cacatcctgc gagccgccgt attggcggcg atgctgtttg c    300 cgttgccgtc catggccgat caggccggca agagcccaa cgctgtgcgc taccacggcg      360

```
gcgacgaaat cattctccag ggctttcact ggaacgtcgt ccgcgaagcg cccaacgact      420
ggtacaacat cctgcgccag caggccgcga ccatcgccgc cgacggcttc tcggcgatct      480
ggatgccggt gccctggcgc gacttctcca gctggagcga cggcagcaag tccgcggcg       540
gtgaaggcta cttctggcac gacttcaaca agaacggccg ctatggcagt gacgcccagc      600
tgcgtcaggc cgccagcgcg ctcggtggcg ccggcgtgaa agtgctttac gacgtggtgc      660
ccaaccacat gaaccgtggc tatccggaca aggagatcaa cctcccggcc ggccagggct      720
tctggcgcaa cgactgcgcc gacccgggca actaccccaa tgattgcgac gacggcgacc      780
gcttcatcgg cggcgatgcg gacctcaaca ccggccaccc gcaggtctac ggcatgttcc      840
gcgatgaatt caccaacctg cgcagtcagt acggtgccgg cggcttccgc ttcgactttg      900
ttcgggcta tgcgccggag cgggtcaaca gctggatgac cgatagcgcc gacaacagct       960
tctgcgtcgg cgaactgtgg aaaggcccct ctgagtaccc gaactgggac tggcgcaaca     1020
ccgccagctg gcagcagatc atcaaggact ggtccgaccg ggccaagtgc ccggtgttcg     1080
acttcgccct caaggaacgc atgcagaacg ctcgatcgcc gactggaagc acgcctgaac     1140
ggcaatcccg acccgcgtgg cgcgaggtgg cggtgacctt cgtcgacaac cacgacaccg     1200
gctactcgcc cgggcagaac ggtgggcagc accactgggc tctgcaggac gggctgatcc     1260
gccaggccta cgcctacatc ctcaccagcc ccggtacgcc ggtggtgtac tggtcgcaca     1320
tgtacgactg gggttacggc gacttcatcc gtcagctgat ccaggtgcgt cgcgccgccg     1380
gcgtgcgcgc cgattcggcg atcagcttcc acagcggcta cagcggtctg gtcgccaccg     1440
tcagcggcag ccagcagacc ctggtggtgg cgctcaactc cgacctgggc aatcccggcc     1500
aggtggccag cggcagcttc agcgaggcgg tcaacgccag caacggccag gtgcgcgtgt     1560
ggcgtagcgg cacgggcagc ggtggcggtg aacccggcgc tctggtcagt gtgagtttcc     1620
gctgcgacaa cggcgcgacg cagatgggcg acagcgtcta cgcggtcggc aacgtcagcc     1680
agctcggtaa ctggagcccg gccgcggcgt tgcgcctgac cgacaccagc ggctacccga     1740
cctggaaggg cagcattgcc ttgcctgccg gccagaacga ggaatggaaa tgcctgatcc     1800
gcaacgaggc caacgccacc caggtgcggc aatggcaggg cggggcaaac aacagcctga     1860
cgccgagcga gggcgccacc accgtcggcc ggctctagcc cgggcggcaa ctcggccgtc     1920
tcgcggatgt gaggcggctg gtctcggcgg cggtatcgtt gcgctggggg cggggccgcc     1980
gttcacgcgc cctgctatcg ctagttttcg gcgctccgcg catcggccag ttgccagcga     2040
atcgcctgcg cttcggcctg gtgcaggtcg tcgagcagcg ct                        2082
```

<210> SEQ ID NO 13
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe

```
              50                  55                  60
Ser Ser Trp Thr Asp Gly Gly Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
                100                 105                 110

Asp Val Val Pro Asn His Met Asn Arg Phe Tyr Pro Asp Lys Glu Ile
                115                 120                 125

Asn Leu Pro Ala Gly Gln Arg Phe Trp Arg Asn Asp Cys Pro Asp Pro
130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
                180                 185                 190

Phe Asp Phe Val Arg Gly Tyr Ala Pro Glu Arg Val Asp Ser Trp Met
                195                 200                 205

Ser Asp Ser Ala Asp Ser Ser Phe Cys Val Gly Glu Leu Trp Lys Glu
210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
                260                 265                 270

Gln Gly Leu Asn Gly Asn Pro Asp Pro Arg Trp Arg Glu Val Ala Val
                275                 280                 285

Thr Phe Val Asp Asn His Asp Thr Gly Tyr Ser Pro Gly Gln Asn Glu
                290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
                340                 345                 350

Arg Arg Thr Ala Gly Val Arg Ala Asp Ser Ala Ile Ser Phe His Ser
                355                 360                 365

Gly Tyr Ser Gly Leu Val Ala Thr Val Ser Gly Ser Gln Gln Thr Leu
                370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
                420                 425                 430

<210> SEQ ID NO 14
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 14

```
atggatcagg ccggcaagag cccggccggg gtgcgctacc acggcggcga cgaaatcatc      60
ctccagggct tccactggaa cgtcgtccgc gaagcgccct acaactggta caacatcctc     120
cgccaacagg cctcgacgat cgcggccgac ggcttctcgg caatctggat gccagtgccc     180
tggcgtgact tctccagctg gaccgacggc ggcaagtccg gcggcggcga aggctacttc     240
tggcacgact tcaacaagaa cggccgctac ggcagcgacg cccagctgcg ccaggccgcc     300
ggcgcactcg gtggcgccgg ggtgaaggtg ctctacgatg tggtgcccaa tcacatgaac     360
cgcttctacc cggacaagga gatcaacctg ccggccggcc agcgcttctg cgcaacgac      420
tgcccggatc cgggcaacgg ccccaacgac tgcgacgacg tgaccgcctt cctgggcggc     480
gaggcggacc tgaacaccgg ccatccgcag atttacggca tgtttcgcga cgagtttacc     540
aacctgcgca gcggctacgg cgccggcggc ttccgcttcg acttcgttcg cggctatgcg     600
cccgagcggg tcgacagctg gatgagcgac agcgccgaca gcagcttctg cgttggcgag     660
ctgtggaaag agccttctga atatccgccg tgggactggc gcaacacggc gagctggcag     720
cagatcatca aggactggtc cgaccgggcc aagtgcccgg tgttcgactt cgctctcaag     780
gagcgcatgc agaacggctc ggtcgccgac tggaagcagg gcctcaatgg caaccccgac     840
ccgcgctggc gcgaggtggc ggtgaccttc gtcgacaacc acgacaccgg ctattcgccc     900
gggcagaacg aaggccagca cctgtggccg ctgcaggacg ggctgatccg ccaggcctac     960
gcctacatcc tcaccagccc gggcacgccg gtggtgtact ggccgcacat gtacgactgg    1020
ggctacggcg acttcatccg ccagctgatc caggtgcggc gcaccgccgg cgtgcgcgcc    1080
gattcggcga tcagcttcca tagcggctac agcggtctgg tcgctaccgt cagcggcagc    1140
cagcagaccc tggtggtggc gctcaactcc gatctggcca accccggcca ggttgccagc    1200
ggcagcttca gcgaggcggt caacgccagc aacggccagg tgcgcgtctg cgcagcggt     1260
agcggcgatg gcggcgggaa tgacggcggc tga                                 1293
```

<210> SEQ ID NO 15
<211> LENGTH: 430
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Gly Lys Ser Gly Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Phe Tyr Pro Asp Lys Glu Ile
        115                 120                 125
```

Asn Leu Pro Ala Gly Gln Arg Phe Trp Arg Asn Asp Cys Pro Asp Pro
        130                 135                 140

Gly Asp Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
        210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Glu
290                 295                 300

Gly Gln His Leu Trp Ala Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
        370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Asn Asp Gly Gly
            420                 425                 430

<210> SEQ ID NO 16
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggatcagg ccggcaagag cccggccggg gtgcgctacc acggcggcga cgaaatcatc        60
ctccagggct ccactggaa cgtcgtccgc gaagcgccct acaactggta caacatcctc        120
cgccaacagg cctcgacgat cgcggccgac ggcttctcgg caatctggat gccagtgccc        180
tggcgtgact ctccagctg accgacggc ggcaagtccg cggcggcga aggctacttc         240 tggcacgact caacaagaa cggccgctac ggcagcgacg cccagctgcg ccaggccgcc        300
ggcgcactcg gtggcgccgg ggtgaaggtg ctctacgatg tggtgcccaa tcacatgaac        360

-continued

```
cgcttctacc cggacaagga gatcaacctg ccggccggcc agcgcttctg gcgcaacgac      420
tgcccggacc cgggcgacgg ccccaacgac tgcgacgacg gtgaccgctt cctgggcggc      480
gagtcggacc tgaacaccgg ccatccgcag atttacggca tgtttcgcga cgagtttacc      540
aacctgcgca gcggctacgg cgccggcggc ttccgcttcg acttcgttcg cggctatgcg      600
cccgagcggg tcgacagctg gatgagcgac agcgccgaca gcagcttctg cgttggcgag      660
ctgtggaaag agccttctga atatccgccg tgggactggc gcaacacggc gagctggcag      720
cagatcatca aggactggtc cgaccgggcc aagtgcccgg tgttcgactt cgctctcaag      780
gagcgcatgc agaacggctc ggtcgccgac tggaagcagg cctcaatgg caaccccgac      840 ccgcgctggc gcgaggtggc ggtgaccttc gtcgacaacc acgacaccgg ctattcgccc      900
gggcagaacg aaggccagca cctgtgggcg ctgcaggacg ggctgatccg ccaggcctac      960
gcctacatcc tcaccagccc gggcacgccg gtggtgtact ggccgcacat gtacgactgg     1020
ggctacggcg acttcatccg ccagctgatc caggtgcggc gcaccgccgg cgtgcgcgcc     1080
gattcggcga tcagcttcca tagcggctac agcggtctgg tcgctaccgt cagcggcagc     1140
cagcagaccc tggtggtggc gctcaactcc gatctggcca accccggcca ggttgccagc     1200
ggcagcttca gcgaggcggt caacgccagc aacggccagg tgcgcgtctg gcgcagcggt     1260
agcggcgatg gcggcgggaa tgacggcggc tga                                 1293
```

<210> SEQ ID NO 17
<211> LENGTH: 430
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Gly Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Asp Tyr Pro Asp Lys Glu Ile
        115                 120                 125

Asn Leu Pro Ala Gly Gln Arg Phe Trp Arg Asn Asp Cys Pro Asp Pro
    130                 135                 140

Gly Asn Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190
```

```
Phe Asp Phe Val Arg Gly Tyr Ala Pro Glu Arg Val Asp Ser Trp Met
            195                 200                 205

Ser Asp Ser Ala Asp Ser Ser Phe Cys Val Gly Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

Gln Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Glu
    290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
            420                 425                 430

<210> SEQ ID NO 18
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggatcagg ccggcaagag cccggccggg gtgcgctacc acggcggcga cgaaatcatc    60
ctccagggct ccactggaa cgtcgtccgc gaagcgccct acaactggta caacatcctc    120
cgccaacagg cctcgacgat cgcggccgac ggcttctcgg caatctggat gccagtgccc    180
tggcgtgact ctccagctg accgacggc ggcaagtccg gcggcggcga aggctacttc    240
tggcacgact tcaacaagaa cggccgctac ggcagcgacg cccagctgcg ccaggccgcc    300
ggcgcactcg gtggcgccgg ggtgaaggtg ctctacgatg tggtgcccaa tcacatgaac    360
cgcgactacc ggacaagga gatcaacctg ccggccggcc agcgcttctg cgcaacgac    420 tgcccggacc cgggcaacgg ccccaacgac tgcgacgacg gtgaccgctt cctgggcggc    480
gagtcggacc tgaacaccgg ccatccgcag atttacggca tgtttcgcga cgagtttacc    540
aacctgcgca gcggctacgg cgccggcggc ttccgcttcg acttcgttcg cggctatgcg    600
cccgagcggg tcgacagctg gatgagcgac agcgccgaca gcagcttctg cgttggcgag    660
ctgtggaaag agccttctga atatccgccg tgggactggc gcaacacggc gagctggcag    720
```

```
cagatcatca aggactggtc cgaccgggcc aagtgcccgg tgttcgactt cgctctcaag    780
gagcgcatgc agaacggctc ggtcgccgac tggaagcagg gcctcaatgg caaccccgac    840
ccgcgctggc gcgaggtggc ggtgaccttc gtcgacaacc acgacaccgg ctattcgccc    900
gggcagaacg aaggccagca cctgtggccg ctgcaggacg gctgatccg ccaggcctac     960 gcctacatcc tcaccagccc gggcacgccg gtggtgtact ggccgcacat gtacgactgg   1020
ggctacggcg acttcatccg ccagctgatc caggtgcggc gcaccgccgg cgtgcgcgcc   1080
gattcggcga tcagcttcca tagcggctac agcggtctgg tcgctaccgt cagcggcagc   1140
cagcagaccc tggtggtggc gctcaactcc gatctggcca accccggcca ggttgccagc   1200
ggcagcttca gcgaggcggt caacgccagc aacggccagg tgcgcgtctg gcgcagcggt   1260
agcggcgatg gcggcgggaa tgacggcggc tga                                 1293
```

<210> SEQ ID NO 19
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Asp Gln Ser Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Asp Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Asp Tyr Pro Asp Lys Glu Ile
        115                 120                 125

Asn Leu Pro Ala Gly Gln Arg Phe Trp Arg Asn Asp Cys Pro Asp Pro
    130                 135                 140

Gly Asn Gly Pro Asn Asp Cys Asp Asp Gly Asp Arg Phe Leu Gly Gly
145                 150                 155                 160

Glu Ser Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
```

|  | 260 |  |  |  | 265 |  |  |  | 270 |  |  |
|---|---|---|---|---|---|---|---|---|---|---|---|

Gln Gly Leu Asn Gly Asn Pro Asp Pro Arg Trp Arg Glu Val Ala Val
                275                 280                 285

Thr Phe Val Asp Asn His Asp Thr Gly Tyr Ser Pro Gly Gln Asn Glu
        290                 295                 300

Gly Gln His Leu Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
                340                 345                 350

Arg Arg Thr Ala Gly Val Arg Ala Asp Ser Ala Ile Ser Phe His Ser
                355                 360                 365

Gly Tyr Ser Gly Leu Val Ala Thr Val Ser Gly Ser Gln Gln Thr Leu
        370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
                420                 425                 430

<210> SEQ ID NO 20
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggatcaga gcggcaagag cccggccggg gtgcgctacc acggcggcga cgaaatcatc       60
ctccagggct ccactggaa cgtcgtccgc gaagcgccct acaactggta acacatcctc      120
cgccaacagg cctcgacgat cgcggccgac ggcttctcgg caatctggat gccagtgccc      180
tggcgtgact tctccagctg gaccgacggc gacaagtccg gcggcggcga aggctacttc      240
tggcacgact tcaacaagaa cggccgctac ggcagcgacg cccagctgcg ccaggccgcc      300
ggcgcactcg gtggcgccgg ggtgaaggtg ctctacgatg tggtgcccaa tcacatgaac      360
cgcgactacc cggacaagga gatcaacctg ccggccggcc agcgcttctg cgcaacgac       420 tgcccggacc cgggcaacgg ccccaacgac tgcgacgacg tgaccgcctt cctgggcggc      480
gagtcggacc tgaacaccgg ccatccgcag atttacggca tgtttcgcga cgagtttacc      540
aacctgcgca gcggctacgg cgccggcggc ttccgcttcg acttcgttcg cggctatgcg      600
cccgagcggg tcgacagctg gatgagcgac agcgccgaca gcagcttctg cgttggcgag      660
ctgtggaaag agccttctga atatccgccg tgggactggc gcaacacggc gagctggcag      720
cagatcatca aggactggtc cgaccgggcc aagtgcccgg tgttcgactt cgctctcaag      780
gagcgcatgc agaacggctc ggtcgccgac tggaagcagg gcctcaatgg caaccccgac      840
cgcgcctggc gcgaggtggc ggtgaccttc gtcgacaacc acgacaccgg ctattcgccc      900
gggcagaacg aaggccagca cctgtggccg ctgcaggacg gctgatccg  ccaggcctac      960 gcctacatcc tcaccagccc gggcacgccg gtggtgtact ggccgcacat gtacgactgg     1020
ggctacggcg acttcatccg ccagctgatc caggtgcggc gcaccgccgg cgtgcgcgcc     1080
gattcggcga tcagcttcca tagcggctac agcggtctgg tcgctaccgt cagcggcagc     1140

```
cagcagaccc tggtggtggc gctcaactcc gatctggcca accccggcca ggttgccagc    1200
ggcagcttca gcgaggcggt caacgccagc aacggccagg tgcgcgtctg gcgcagcggt    1260
agcggcgatg gcggcgggaa tgacggcggc tga                                 1293
```

<210> SEQ ID NO 21
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
                20                  25                  30

Pro Tyr Asn Trp Tyr Asn Ile Leu Arg Gln Gln Ala Ser Thr Ile Ala
            35                  40                  45

Ala Asp Gly Phe Ser Ala Ile Trp Met Pro Val Pro Trp Arg Asp Phe
        50                  55                  60

Ser Ser Trp Thr Asp Gly Asp Lys Ser Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Ala Gly Val Lys Val Leu Tyr
            100                 105                 110

Asp Val Val Pro Asn His Met Asn Arg Phe Tyr Pro Asp Lys Glu Ile
        115                 120                 125

Asn Leu Pro Ala Gly Gln Arg Phe Trp Arg Asn Asp Cys Pro Asp Pro
130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

His Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Gly
    290                 295                 300

Gly Gln His Lys Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335
```

```
Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Asn Asp Gly Gly
                420                 425                 430
```

<210> SEQ ID NO 22
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gatcaagcag gaaaaagccc ggcaggcgtc agatatcatg gcggcgatga atcatcctt       60
cagggctttc attggaacgt cgtcagagaa gcgccgtata actggtataa catcctgaga    120
caacaagcga gcacaattgc cgctgatggc ttttccgcaa tctggatgcc ggttccgtgg    180
agagattta gcagctggac ggatggagat aaaagcggag gcggcgaagg atatttttgg    240
catgacttta caaaaacgg ccgctatgga agcgatgctc aactgagaca agcagcagga    300
gcacttggag gagcaggagt caaagtcctg tacgatgtcg tcccgaacca tatgaaccgc    360
ttttatccgg acaaagaaat caatctgccg gcaggccaaa gattttggag aaacgattgc    420
ccggacccgg gaaatggacc gaatgattgc gatgatggcg atagatttct gggcggcgaa    480
gcggatctga atacaggcca tccgcaaatc tatggcatgt tcgggacgaa atttacgaat    540
ctgagaagcg gatatggagc gggcggattt cgctttgatt ttgtcagagg ctatgccccg    600
gaaagagttg atagctggat gagcgattca gcggatagca gcttttgcgt cggcgaactt    660
tggaaagaac cgagcgaata tccgccgtgg gattggagaa atacagcgag ctggcagcag    720
atcatcaaag attggagcga tagagcaaaa tgcccggtct ttgactttgc cctgaaagaa    780
cgcatgcaaa atgaagcgt cgccgattgg aaacatggcc tgaacggaaa tccggacccg    840
agatggagag aagtcgccgt cacgtttgtc gataaccatg acacaggata tagcccggga    900
caaaatggag acaacataa atggccgctt caagatggcc ttatcagaca ggcgtatgcc    960
tatatcctta catcaccggg aacaccggtt gtttattggc cgcatatgta tgattgggc   1020
tatggcgatt tcatccgcca actgatccag gttagaagaa cagcaggagt cagagcggat   1080
agcgccatta gctttcatag cggctatagc ggacttgtcg ctacagttag cggcagccaa   1140
caaacactgg tcgtcgccct gaatagcgat ctggcaaatc cgggacaagt tgctagcggc   1200
agctttagcg aagcagtcaa tgccagcaat ggccaagtca gagtctggag aagcggaagc   1260
ggagatggag aggaaatga cggaggataa                                     1290
```

<210> SEQ ID NO 23
<211> LENGTH: 430
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 23

| | | | | | | | | | | | | | | |
|---|---|---|---|---|---|---|---|---|---|---|---|---|---|---|
| Met | Asp | Gln | Ala | Gly | Lys | Ser | Pro | Ala | Gly | Val | Arg | Tyr | His | Gly |
| 1 | | | | 5 | | | | | 10 | | | | | 15 |
| Asp | Glu | Ile | Ile | Leu | Gln | Gly | Phe | His | Trp | Asn | Val | Val | Arg | Glu | Ala |
| | | | 20 | | | | | 25 | | | | | 30 | | |
| Pro | Tyr | Asn | Trp | Tyr | Asn | Ile | Leu | Arg | Gln | Gln | Ala | Ser | Thr | Ile | Ala |
| | | 35 | | | | | 40 | | | | | 45 | | | |
| Ala | Asp | Gly | Phe | Ser | Ala | Ile | Trp | Met | Pro | Val | Pro | Trp | Arg | Asp | Phe |
| 50 | | | | | 55 | | | | | 60 | | | | | |
| Ser | Ser | Trp | Thr | Asp | Gly | Asp | Lys | Ser | Gly | Gly | Glu | Gly | Tyr | Phe |
| 65 | | | | 70 | | | | | 75 | | | | | 80 |
| Trp | His | Asp | Phe | Asn | Lys | Asn | Gly | Arg | Tyr | Gly | Ser | Asp | Ala | Gln | Leu |
| | | | | 85 | | | | | 90 | | | | | 95 | |
| Arg | Gln | Ala | Ala | Gly | Ala | Leu | Gly | Gly | Ala | Gly | Val | Lys | Val | Leu | Tyr |
| | | | 100 | | | | | 105 | | | | | 110 | | |
| Asp | Val | Val | Pro | Asn | His | Met | Asn | Arg | Phe | Tyr | Pro | Asp | Lys | Glu | Ile |
| | | 115 | | | | | 120 | | | | | 125 | | | |
| Asn | Leu | Pro | Ala | Gly | Gln | Arg | Phe | Trp | Arg | Asn | Asp | Cys | Pro | Asp | Pro |
| 130 | | | | | 135 | | | | | 140 | | | | | |
| Gly | Asn | Gly | Pro | Asn | Asp | Cys | Asp | Asp | Gly | Asp | Arg | Phe | Leu | Gly | Gly |
| 145 | | | | | 150 | | | | | 155 | | | | | 160 |
| Glu | Ala | Asp | Leu | Asn | Thr | Gly | His | Pro | Gln | Ile | Tyr | Gly | Met | Phe | Arg |
| | | | | 165 | | | | | 170 | | | | | 175 | |
| Asp | Glu | Phe | Thr | Asn | Leu | Arg | Ser | Gly | Tyr | Gly | Ala | Gly | Gly | Phe | Arg |
| | | | 180 | | | | | 185 | | | | | 190 | | |
| Phe | Asp | Phe | Val | Arg | Gly | Tyr | Ala | Pro | Glu | Arg | Val | Asp | Ser | Trp | Met |
| | | 195 | | | | | 200 | | | | | 205 | | | |
| Ser | Asp | Ser | Ala | Asp | Ser | Ser | Phe | Cys | Val | Gly | Glu | Leu | Trp | Lys | Glu |
| 210 | | | | | 215 | | | | | 220 | | | | | |
| Pro | Ser | Glu | Tyr | Pro | Pro | Trp | Asp | Trp | Arg | Asn | Thr | Ala | Ser | Trp | Gln |
| 225 | | | | | 230 | | | | | 235 | | | | | 240 |
| Gln | Ile | Ile | Lys | Asp | Trp | Ser | Asp | Arg | Ala | Lys | Cys | Pro | Val | Phe | Asp |
| | | | | 245 | | | | | 250 | | | | | 255 | |
| Phe | Ala | Leu | Lys | Glu | Arg | Met | Gln | Asn | Gly | Ser | Val | Ala | Asp | Trp | Lys |
| | | | 260 | | | | | 265 | | | | | 270 | | |
| His | Gly | Leu | Asn | Gly | Asn | Pro | Asp | Pro | Arg | Trp | Arg | Glu | Val | Ala | Val |
| | | 275 | | | | | 280 | | | | | 285 | | | |
| Thr | Phe | Val | Asp | Asn | His | Asp | Thr | Gly | Tyr | Ser | Pro | Gly | Gln | Asn | Gly |
| 290 | | | | | 295 | | | | | 300 | | | | | |
| Gly | Gln | His | Arg | Trp | Pro | Leu | Gln | Asp | Gly | Leu | Ile | Arg | Gln | Ala | Tyr |
| 305 | | | | | 310 | | | | | 315 | | | | | 320 |
| Ala | Tyr | Ile | Leu | Thr | Ser | Pro | Gly | Thr | Pro | Val | Val | Tyr | Trp | Pro | His |
| | | | | 325 | | | | | 330 | | | | | 335 | |
| Met | Tyr | Asp | Trp | Gly | Tyr | Gly | Asp | Phe | Ile | Arg | Gln | Leu | Ile | Gln | Val |
| | | | 340 | | | | | 345 | | | | | 350 | | |
| Arg | Arg | Thr | Ala | Gly | Val | Arg | Ala | Asp | Ser | Ala | Ile | Ser | Phe | His | Ser |
| | | 355 | | | | | 360 | | | | | 365 | | | |
| Gly | Tyr | Ser | Gly | Leu | Val | Ala | Thr | Val | Ser | Gly | Ser | Gln | Gln | Thr | Leu |
| 370 | | | | | 375 | | | | | 380 | | | | | |
| Val | Val | Ala | Leu | Asn | Ser | Asp | Leu | Ala | Asn | Pro | Gly | Gln | Val | Ala | Ser |
| 385 | | | | | 390 | | | | | 395 | | | | | 400 |

-continued

```
Gly Ser Phe Ser Glu Ala Val Asn Ala Ser Asn Gly Gln Val Arg Val
            405                 410                 415

Trp Arg Ser Gly Ser Gly Asp Gly Gly Gly Asn Asp Gly Gly
            420                 425                 430

<210> SEQ ID NO 24
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gatcaagcag gaaaaagccc ggcaggcgtc agatatcatg gcggcgatga atcatcctt      60 cagggctttc attggaacgt cgtcagagaa gcgccgtata actggtataa catcctgaga   120
caacaagcga gcacaattgc cgctgatggc ttttccgcaa tctggatgcc ggttccgtgg   180
agagatttta gcagctggac ggatggagat aaaagcggag gcggcgaagg atattttgg    240 catgacttta acaaaaacgg ccgctatgga agcgatgctc aactgagaca gcagcagga    300 gcacttggag gagcaggagt caaagtcctg tacgatgtcg tcccgaacca tatgaaccgc   360
ttttatccgg acaagaaat caatctgccg gcaggccaaa gattttggag aaacgattgc    420
ccggacccgg gaaatggacc gaatgattgc gatgatggcg atagatttct gggcggcgaa   480
gcggatctga atacaggcca tccgcaaatc tatggcatgt tcgggacga atttacgaat    540 ctgagaagcg atatggagc gggcggattt cgctttgatt ttgtcagagg ctatgccccg    600
gaaagagttg atagctggat gagcgattca gcggatagca gcttttgcgt cggcgaactt   660
tggaaagaac cgagcgaata tccgccgtgg gattggagaa atacagcgag ctggcagcag   720
atcatcaaag attggagcga tagagcaaaa tgcccggtct ttgactttgc cctgaaagaa   780
cgcatgcaaa atgaagcgt cgccgattgg aaacatggcc tgaacggaaa tccggacccg   840
agatggagag aagtcgccgt cacgtttgtc gataaccatg acacaggata tagcccggga   900
caaaatggag acaacatcg ttggccgctt caagatggcc ttatcagaca ggcgtatgcc    960
tatatcctta catcaccggg aacaccggtt gtttattggc cgcatatgta tgattgggc   1020 tatggcgatt tcatccgcca actgatccag gttagaagaa cagcaggagt cagagcggat  1080
agcgccatta gctttcatag cggctatagc ggacttgtcg ctacagttag cggcagccaa  1140
caaacactgg tcgtcgccct gaatagcgat ctggcaaatc cggacaagt tgctagcggc   1200 agctttagcg aagcagtcaa tgccagcaat ggccaagtca gagtctggag aagcggaagc  1260
ggagatggag gaggaaatga cggaggataa                                    1290

<210> SEQ ID NO 25
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45
```

```
Ala Asp Gly Phe Ser Ala Ile Trp Met Pro Val Pro Trp Arg Asp Phe
     50                  55                  60

Ser Ser Trp Thr Asp Gly Asp Lys Ser Gly Gly Glu Gly Tyr Phe
65              70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Phe Tyr Pro Asp Lys Glu Ile
            115                 120                 125

Asn Leu Pro Ala Gly Gln Arg Phe Trp Arg Asn Asp Cys Pro Asp Pro
            130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
                180                 185                 190

Phe Asp Phe Val Arg Gly Tyr Ala Pro Glu Arg Val Asp Ser Trp Met
            195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

His Gly Leu Asn Gly Asn Pro Asp Pro Arg Trp Arg Glu Val Ala Val
            275                 280                 285

Thr Phe Val Asp Asn His Asp Thr Gly Tyr Ser Pro Gly Gln Asn Gly
            290                 295                 300

Gly Gln His His Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
            355                 360                 365

Gly Tyr Ser Gly Leu Val Ala Thr Val Ser Gly Ser Gln Gln Thr Leu
            370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Asn Asp Gly Gly
            420                 425                 430

<210> SEQ ID NO 26
<211> LENGTH: 1290
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 26

```
gatcaagcag gaaaaagccc ggcaggcgtc agatatcatg gcggcgatga atcatccttt     60
cagggctttc attggaacgt cgtcagagaa gcgccgtata actggtataa catcctgaga    120
caacaagcga gcacaattgc cgctgatggc ttttccgcaa tctggatgcc ggttccgtgg    180
agagatttta gcagctggac ggatggagat aaaagcggag gcggcgaagg atatttttgg    240
catgacttta caaaaacgg ccgctatgga agcgatgctc aactgagaca agcagcagga    300
gcacttggag gagcaggagt caaagtcctg tacgatgtcg tcccgaacca tatgaaccgc    360
ttttatccgg acaaagaaat caatctgccg gcaggccaaa gattttggag aaacgattgc    420
ccggacccgg gaaatggacc gaatgattgc gatgatggcg atagatttct gggcggcgaa    480
gcggatctga atacaggcca tccgcaaatc tatggcatgt ttcgggacga atttacgaat    540
ctgagaagcg gatatggagc gggcggattt cgctttgatt ttgtcagagg ctatgccccg    600
gaaagagttg atagctggat gagcgattca gcggatagca gcttttgcgt cggcgaactt    660
tggaaagaac cgagcgaata tccgccgtgg gattggagaa atacagcgag ctggcagcag    720
atcatcaaag attggagcga tagagcaaaa tgcccggtct ttgactttgc cctgaaagaa    780
cgcatgcaaa atgaagcgt cgccgattgg aaacatggcc tgaacggaaa tccggacccg    840
agatggagag aagtcgccgt cacgtttgtc gataaccatg acacaggata tagcccggga    900
caaaatggag acaacatca ctggccgctt caagatggcc ttatcagaca ggcgtatgcc    960
tatatcctta catcaccggg aacaccggtt gtttattggc cgcatatgta tgattgggc   1020
tatggcgatt tcatccgcca actgatccag gttagaagaa cagcaggagt cagagcggat   1080
agcgccatta gctttcatag cggctatagc ggacttgtcg ctacagttag cggcagccaa   1140
caaacactgg tcgtcgccct gaatagcgat ctggcaaatc cgggacaagt tgctagcggc   1200
agctttagcg aagcagtcaa tgccagcaat ggccaagtca gtctggag aagcggaagc   1260
ggagatggag gaggaaatga cggaggataa                                   1290
```

<210> SEQ ID NO 27
<211> LENGTH: 429
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110
```

Val Val Pro Asn His Met Asn Arg Phe Tyr Pro Asp Lys Glu Ile Asn
            115                 120                 125

Leu Pro Ala Gly Gln Arg Phe Trp Arg Asn Asp Cys Pro Asp Pro Gly
        130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Glu Pro
210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys Gln
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Glu Gly
        290                 295                 300

Gln His Arg Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 28
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gatcaagcag gaaaaagccc ggcaggcgtc agatatcatg gcggcgatga atcatccttt     60
cagggctttc attggaacgt cgtcagagaa gcgccgtata actggtataa catcctgaga    120
caacaagcga gcacaattgc cgctgatggc ttttccgcaa tctggatgcc ggttccgtgg    180
agagatttta gcagctggac ggatggaggc aaaagcggag cggcgaagg atattttgg     240 catgacttta acaaaaacgg ccgctatgga agcgatgctc aactgagaca agcagcagga    300

```
gcacttggag gagcaggagt caaagtcctg tacgatgtcg tcccgaacca tatgaaccgc    360 tttttatccgg acaaagaaat caatctgccg gcaggccaaa gattttggag aaacgattgc    420
ccggacccgg gaaatggacc gaatgattgc gatgatggcg atagatttct gggcggcgaa    480
gcggatctga atacaggcca tccgcaaatc tatggcatgt tcgggacga atttacgaat     540 ctgagaagcg gatatggagc gggcggattt cgctttgatt ttgtcagagg ctatgccccg    600
gaaagagttg atagctggat gagcgattca gcggatagca gcttttgcgt cggcgaactt    660
tggaaagaac cgagcgaata tccgccgtgg gattggagaa atacagcgag ctggcagcag    720
atcatcaaag attggagcga tagagcaaaa tgcccggtct ttgactttgc cctgaaagaa    780
cgcatgcaaa atggaagcgt cgccgattgg aaacaaggcc tgaacggaaa tccggacccg    840
agatggagag aagtcgccgt cacgtttgtc gataaccatg acacaggata tagcccggga    900
caaaatgaag acaacatcg gtggccgctt caagatggcc ttatcagaca ggcgtatgcc      960
tatatcctta catcaccggg aacaccggtt gtttattggc cgcatatgta tgattggggc    1020
tatggcgatt tcatccgcca actgatccag gttagaagaa cagcaggagt cagagcggat    1080
agcgccatta gctttcatag cggctatagc ggacttgtcg ctacagttag cggcagccaa    1140
caaacactgg tcgtcgccct gaatagcgat ctggcaaatc cgggacaagt tgctagcggc    1200
agctttagcg aagcagtcaa tgccagcaat ggccaagtca gagtctggag aagcggaagc    1260
ggagatggag gaggaaatga cggaggataa                                     1290

<210> SEQ ID NO 29
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
```

```
                          180                 185                 190
Asp Phe Val Arg Gly Tyr Ala Pro Glu Arg Val Asp Ser Trp Met Ser
            195                 200                 205
Asp Ser Ala Asp Ser Ser Phe Cys Val Gly Glu Leu Trp Lys Glu Pro
        210                 215                 220
Ser Glu Tyr Pro Pro Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys Gln
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Glu Gly
        290                 295                 300
Gln His Lys Trp Pro Leu Gln Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
        370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly
            420                 425

<210> SEQ ID NO 30
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gatcaagcag gaaaaagccc ggcaggcgtc agatatcatg gcggcgatga atcatccttt       60
cagggctttc attggaacgt cgtcagagaa gcgccgtata actggtataa catcctgaga      120
caacaagcga gcacaattgc cgctgatggc ttttccgcaa tctggatgcc ggttccgtgg      180
agagatttta gcagctggac ggatggaggc aaaagcggag gcggcgaagg atattttggg      240
catgacttta caaaaacggc cgctatggaa gcgatgctca actgagaca agcagcagga       300 gcacttggag gagcaggagt caaagtcctg tacgatgtcg tcccgaacca tatgaaccgc      360
ttttatccgg acaaagaaat caatctgccg gcaggccaaa gatttggag aaacgattgc       420 ccggaccggg gaaatggacc gaatgattgc gatgatggcg atagatttct gggcggcgaa      480
gcggatctga atacaggcca tccgcaaatc tatggcatgt tcgggacga atttacgaat       540 ctgagaagcg gatatggagc gggcggattt cgctttgatt ttgtcagagg ctatgccccg      600
gaaagagttg atagctggat gagcgattca gcggatagca gcttttgcgt cggcgaactt      660
```

-continued

```
tggaaagaac cgagcgaata tccgccgtgg gattggagaa atacagcgag ctggcagcag    720
atcatcaaag attggagcga tagagcaaaa tgcccggtct ttgactttgc cctgaaagaa    780
cgcatgcaaa atggaagcgt cgccgattgg aaacaaggcc tgaacggaaa tccggacccg    840
agatggagag aagtcgccgt cacgtttgtc gataaccatg acacaggata tagcccggga    900
caaaatgaag acaacataa gtggccgctt caagatggcc ttatcagaca ggcgtatgcc    960
tatatcctta catcaccggg aacaccggtt gtttattggc cgcatatgta tgattggggc   1020
tatggcgatt tcatccgcca actgatccag gttagaagaa cagcaggagt cagagcggat   1080
agcgccatta gctttcatag cggctatagc ggacttgtcg ctacagttag cggcagccaa   1140
caaacactgg tcgtcgccct gaatagcgat ctggcaaatc cgggacaagt tgctagcggc   1200
agctttagcg aagcagtcaa tgccagcaat ggccaagtca gagtctggag aagcggaagc   1260
ggagatggag gaggaaatga cggaggataa                                    1290
```

<210> SEQ ID NO 31
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Phe Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Gly Pro Asn Asp Cys Asp Asp Gly Asp Arg Phe Leu Gly Gly Glu
145                 150                 155                 160

Ala Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Glu Pro
    210                 215                 220

Ser Glu Tyr Pro Pro Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255
```

```
Ala Leu Lys Glu Arg Met Gln Asn Gly Ser Val Ala Asp Trp Lys Gln
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Glu Gly
    290                 295                 300

Gln His His Trp Pro Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
            325                 330                 335

Tyr Asp Trp Gly Tyr Gly Asp Phe Ile Arg Gln Leu Ile Gln Val Arg
        340                 345                 350

Arg Thr Ala Gly Val Arg Ala Asp Ser Ala Ile Ser Phe His Ser Gly
    355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
            405                 410                 415

Arg Ser Gly Ser Gly Asp Gly Gly Asn Asp Gly Gly
            420                 425

<210> SEQ ID NO 32
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gatcaagcag gaaaaagccc ggcaggcgtc agatatcatg gcggcgatga atcatccttt      60
cagggctttc attggaacgt cgtcagagaa gcgccgtata actggtataa catcctgaga     120
caacaagcga gcacaattgc cgctgatggc ttttccgcaa tctggatgcc ggttccgtgg     180
agagatttta gcagctggac ggatggaggc aaaagcggag gcggcgaagg atattttgg      240 catgacttta acaaaaacgg ccgctatgga agcgatgctc aactgagaca agcagcagga     300
gcacttggag gagcaggagt caaagtcctg tacgatgtcg tcccgaacca tatgaaccgc     360
ttttatccgg acaaagaaat caatctgccg gcaggccaaa gattttggag aaacgattgc     420
ccggacccgg gaaatggacc gaatgattgc gatgatggcg atagatttct gggcggcgaa     480
gcggatctga atacaggcca tccgcaaatc tatggcatgt tcgggacga atttacgaat      540 ctgagaagcg gatatggagc gggcggattt cgctttgatt ttgtcagagg ctatgccccg     600
gaaagagttg atagctggat gagcgattca gcggatagca gcttttgcgt cggcgaactt     660
tggaaagaac cgagcgaata tccgccgtgg gattggagaa atacagcgag ctggcagcag     720
atcatcaaag attggagcga tagagcaaaa tgcccggtct tgactttgc cctgaaagaa      780 cgcatgcaaa atgaagcgt cgccgattgg aaacaaggcc tgaacggaaa tccggacccg     840
agatggagag aagtcgccgt cacgtttgtc gataaccatg acacaggata tagcccggga     900
caaaatgaag gacaacatca ttggccgctt caagatggcc ttatcagaca ggcgtatgcc     960
tatatcctta tcatcccggg aacaccggtt gtttattggc cgcatatgta tgattgggc     1020 tatggcgatt tcatccgcca actgatccag gttagaagaa cagcaggagt cagagcggat    1080
```

```
agcgccatta gctttcatag cggctatagc ggacttgtcg ctacagttag cggcagccaa    1140
caaacactgg tcgtcgccct gaatagcgat ctggcaaatc cgggacaagt tgctagcggc    1200
agctttagcg aagcagtcaa tgccagcaat ggccaagtca gagtctggag aagcggaagc    1260
ggagatggag gaggaaatga cggaggataa                                    1290

<210> SEQ ID NO 33
<211> LENGTH: 21
<212> TYPE: PRT
<213> ORGANISM: Pseudomonas saccharophila

<400> SEQUENCE: 33

Met Ser His Ile Leu Arg Ala Ala Val Leu Ala Ala Val Leu Leu Pro
1               5                   10                  15

Phe Pro Ala Leu Ala
            20

<210> SEQ ID NO 34
<211> LENGTH: 101
<212> TYPE: PRT
<213> ORGANISM: Pseudomonas saccharophila

<400> SEQUENCE: 34

Glu Gly Gly Leu Val Asn Val Asn Phe Arg Cys Asp Asn Gly Val Thr
1               5                   10                  15

Gln Met Gly Asp Ser Val Tyr Ala Val Gly Asn Val Ser Gln Leu Gly
                20                  25                  30

Asn Trp Ser Pro Ala Ser Ala Val Arg Leu Thr Asp Thr Ser Ser Tyr
            35                  40                  45

Pro Thr Trp Lys Gly Ser Ile Ala Leu Pro Asp Gly Gln Asn Val Glu
        50                  55                  60

Trp Lys Cys Leu Ile Arg Asn Glu Ala Asp Ala Thr Leu Val Arg Gln
65                  70                  75                  80

Trp Gln Ser Gly Gly Asn Asn Gln Val Gln Ala Ala Gly Ala Ser
                85                  90                  95

Thr Ser Gly Ser Phe
            100

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgacgaggt ccttgttttt c                                              21

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgctagtcgt ccatgtcg                                                  18

<210> SEQ ID NO 37
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccatggatc aggccggcaa gagcccg                                          27

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggatcctca gaacgagccg ctggt                                            25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaattcagcc gccgtcattc ccgcc                                            25

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agatttacgg catgtttcgc                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tagccgctat ggaagctgat                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgaccttcgt cgacaaccac                                                  20

<210> SEQ ID NO 43
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 43
gatagctgct ggtgacggtc         20

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ctgccggccg gccagcgctt ctggcg         26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cgccagaagc gctggccggc cggcag         26

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gacggtgacc gcttcctggg cggcgagtcg         30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
cgactcgccg cccaggaagc ggtcaccgtc         30

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ggcgagctgt ggaaagcccc ttctgaatat ccg         33

<210> SEQ ID NO 49
<211> LENGTH: 33
<212> TYPE: DNA
<213> ORGANISM: Artificial Sequence
<220> FEATURE:

<223> OTHER INFORMATION: Description of Artificial Sequence: Synthetic
       primer

<400> SEQUENCE: 49
cggatattca gaagggcttt tccacagctc gcc                                    33

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 50
gaacggcggc cagcacctgt gggcgctgca g                                      31

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 51
ctgcagcgcc cacaggtgct ggccgccgtt c                                      31

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 52
gtactggccg cacatgtacg actggggcta cggcgaattc atc                         43

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 53
gatgaattcg ccgtagcccc agtcgtacat gtgcggccag tac                         43

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 54
gcgaagcgcc ctacaactgg tacaac                                            26

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

```
<400> SEQUENCE: 55
ccgacggcgg caggtccggc g                                              21

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caagaacagc cgctacggca gcgac                                          25

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacatgaacc gcgactaccc ggacaag                                        27

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgcaacgact gcgccgaccc ggg                                            23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgcgacgagt ttaccaacct gcg                                            23

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtactggccg cacatgtacg actggggcta cggc                                34

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
```
ccaatcacat gaaccgcttc tacccggaca aggag        35

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gatccgggca acggccccaa cgactgcg        28

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gggcggcgag gcggacctga aca        23

<210> SEQ ID NO 64
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: a, c, t, or g

<400> SEQUENCE: 64
ggcgagctgt ggaaagdncc ttctgaatat ccgag        35

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gccttctgaa tatccgccgt gggactggcg caac        34

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccgactggaa gcagggcctc aatggc        26

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccgggcagaa cgaaggccag cacctgtg                                              28

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcacctgtgg ccgctgcagg acg                                                   23

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctggacggat ggagataaaa gcggaggcgg c                                          31

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cgtcgccgat tggaaacatg gcctgaacgg aaatc                                      35

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccgggacaaa atggaggaca acatctttgg c                                          31

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caaaatgaag gacaacataa atggccgctt caagatggcc                                 40

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggacccggga aatggaccga atgattgcg                                    29

<210> SEQ ID NO 74
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gaaggacaac atcagtggcc gcttcaagat ggcc                              34

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gaaggacaac atgtctggcc gcttcaagat ggcc                              34

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caaaatgaag gacaacattg gtggccgctt caagatggcc                        40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caaaatgaag gacaacatta ttggccgctt caagatggcc                        40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caaaatgaag gacaacattg ctggccgctt caagatggcc                        40

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
caaaatgaag gacaacatga atggccgctt caagatggcc                        40

```
<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaaggacaac atttttggcc gcttcaagat gg                                    32

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gaaggacaac atcattggcc gcttcaagat gg                                    32

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, or g

<400> SEQUENCE: 82
caaaatgaag gacaacatnn stggccgctt caagatggcc                            40
```